United States Patent [19]
Farooq et al.

[11] Patent Number: 5,985,921
[45] Date of Patent: *Nov. 16, 1999

[54] 2-PHENYL-2-METHOXYIMINO ACETIC ACID ESTERS

[75] Inventors: Saleem Farooq, Arisdorf, Switzerland; Stephen Trah, Freiburg, Germany; Hugo Ziegler, Witterswil, Switzerland; René Zurflüh; Alfons Pascual, both of Basel, Switzerland; Henry Szczepanski, Wallbach, Switzerland; Roger Graham Hall, Aesch, Switzerland

[73] Assignee: Novartis Corporation, Summit, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/761,675

[22] Filed: Dec. 6, 1996

[30] Foreign Application Priority Data

| Dec. 7, 1995 | [CH] | Switzerland | 3464/95 |
| Dec. 7, 1995 | [CH] | Switzerland | 3465/95 |
| May 14, 1996 | [CH] | Switzerland | 1226/96 |
| Jul. 5, 1996 | [CH] | Switzerland | 1688/96 |
| Oct. 11, 1996 | [CH] | Switzerland | 2493/96 |

[51] Int. Cl.$^6$ .............. A61K 31/24; A61K 31/16; C07C 229/00; C07C 327/00
[52] U.S. Cl. .............. 514/538; 514/599; 514/620; 514/513; 560/35; 564/74; 564/165; 558/230
[58] Field of Search .............. 560/35; 514/538, 514/599, 620, 513; 564/74.165; 558/230

[56] References Cited

U.S. PATENT DOCUMENTS

| 5,346,902 | 9/1994 | Clough et al. | 514/269 |
| 5,371,084 | 12/1994 | de Fraine et al | 514/241 |
| 5,387,607 | 2/1995 | Brand et al. | 514/513 |
| 5,563,168 | 10/1996 | Brand et al. | 514/357 |

FOREIGN PATENT DOCUMENTS

| 9178167 | 12/1991 | Australia . |
| 9526710 | 5/1996 | Australia . |
| 0370629 | 5/1990 | European Pat. Off. . |
| 0414153 | 2/1991 | European Pat. Off. . |
| 0460575 | 12/1991 | European Pat. Off. . |
| 0463488 | 1/1992 | European Pat. Off. . |
| 0472300 | 2/1992 | European Pat. Off. . |
| 0506149 | 9/1992 | European Pat. Off. . |
| 9007493 | 7/1990 | WIPO . |
| 9213830 | 8/1992 | WIPO . |
| 9218487 | 10/1992 | WIPO . |
| 9218494 | 10/1992 | WIPO . |
| 9518789 | 7/1995 | WIPO . |
| 9521153 | 8/1995 | WIPO . |
| 9521154 | 8/1995 | WIPO . |
| 9521156 | 8/1995 | WIPO . |
| 9534526 | 12/1995 | WIPO . |
| 9611183 | 4/1996 | WIPO . |
| 9616026 | 5/1996 | WIPO . |
| 9635669 | 11/1996 | WIPO . |

OTHER PUBLICATIONS

Derwent Abstract 97–011705, 1997.
Derwent Abstract 95–292864, 1995.
Derwent Abstract 95–292863, 1995.
Derwent Abstract 95–292862, 1995.

Primary Examiner—Deborah C. Lambkin
Attorney, Agent, or Firm—William A. Teoli, Jr.; John D. Peabody, III

[57] ABSTRACT

Compounds of the formula

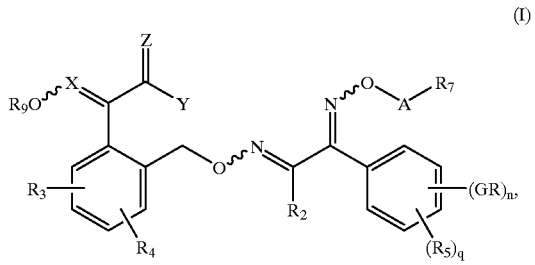

(I)

in which n, q, A, X, G, Y, Z, R, $R_2$, $R_3$, $R_4$, $R_5$, $R_7$ and $R_9$ are as defined in claim 1, and, where appropriate, E/Z isomers, E/Z isomer mixtures and/or tautomers thereof, in each case in the free form or in an agrochemically suitable salt form, can be used as agrochemical active compounds and can be prepared in a manner known per se.

26 Claims, No Drawings

2-PHENYL-2-METHOXYIMINO ACETIC ACID ESTERS

The invention relates to compounds of the formula

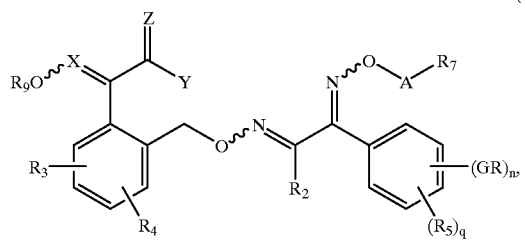

(I)

in which
(A) either
X is CH or N,
Y is $OR_1$ and
Z is O; r
X is N;
Y is $NHR_8$ and
Z is O, S or S(=O);
$R_1$ is $C_1$–$C_4$alkyl;
$R_2$ is H, $C_1$–$C_4$alkyl, halogeno-$C_1$–$C_4$alkyl, $C_3$–$C_6$cycloalkyl, $C_1$–$C_4$alkoxymethyl, $C_1$–$C_4$alkoxy, halogeno-$C_1$–$C_4$alkoxy, $C_1$–$C_4$alkylthio, halogeno-$C_1$–$C_4$alkythio or CN;
$R_3$ and $R_4$ independently of one another are H, $C_{1-C4}$alkyl, $C_1$–$C_4$alkoxy, OH, CN, $NO_2$, a $(C_1$–$C_4$alkyl$)_3$—Si group, where the alkyl groups can be identical or different, halogen, $(C_1$–$C_4$alkyl)S(=O)$_m$, (halogeno-$C_1$–$C_4$alkyl)S(=O)$_m$, halogeno-$C_1$–$C_4$alkyl or halogeno-$C_1$–$C_4$alkoxy;
$R_8$ is H or $C_1$–$C_4$alkyl;
$R_9$ is methyl, fluoromethyl or difluoromethyl;
m is 0, 1 or 2;
G is O or S; and
A is a direct bond, $C_1$–$C_{10}$alkylene, —C(=O)—, —C(=S)— or halogeno-$C_1$–$C_{10}$alkylene and
$R_7$ is a radical $R_{10}$; or
A is $C_1$–$C_{10}$alkylene, —C(=O)—,—C(=S)— or halogeno-$C_1$–$C_{10}$alkylene and
$R_7$ is —CN, $OR_{10}$, $N(R_{10})_2$, where the radicals $R_{10}$ can be identical or different, or —S(=O)$_p R_{10}$;
R is an unsubstituted or mono- or polysubstituted $C_1$–$C_4$alkyl-, $C_2$–$C_4$alkenyl-, $C_2$–$C_4$alkynyl-, $C_3$–$C_6$cycloalkyl-, benzyl-, aryl or heteroaryl-group, where the substituents of the groups independently of one another are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$alkylthio, phenoxy, CN and nitro, or a phenyl radical which is monosubstituted on two adjacent C atoms by an unsubstituted or mono- to tetrasubstituted $C_1$–$C_4$alkylenedioxy group, where the substituents are selected from the group consisting of $C_1$–$C_4$alkyl and halogen; or $CH_2Si(C_1$–$C_4$alkyl)$_3$, where the alkyl groups can be identical or different; and
$R_5$ is $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$alkylthio, $C_1$–$C_6$alkylsulfinyl, halogeno-$C_1$–$C_6$alkylsulfinyl, $C_1$–$C_6$alkylsulfonyl, halogeno-$C_1$–$C_6$alkylsulfonyl, $C_1$–$C_6$alkylsulfonyloxy, halogeno-$C_1$–$C_6$alkylsulfonyloxy, $C_1$–$C_6$alkoxy-$C_1$–$C_6$alkyl, halogeno-$C_1$–$C_6$alkoxy-$C_1$–$C_6$alkyl, $C_1$–$C_6$alkylthio-$C_1$–$C_6$alkyl, halogeno-$C_1$–$C_6$alkylthio-$C_1$–$C_6$alkyl, $C_1$–$C_6$alkylsulfinyl-$C_1$–$C_6$alkyl, halogeno-$C_1$–$C_6$alkylsulfinyl-$C_1$–$C_6$alkyl, $C_1$–$C_6$alkylsulfonyl-$C_1$–$C_6$alkyl, halogeno-$C_1$–$C_6$alkylsulfonyl-$C_1$–$C_6$alkyl, $C_1$–$C_6$alkylcarbonyl, halogeno-$C_1$–$C_6$alkylcarbonyl, $C_1$–$C_6$alkoxycarbonyl, halogeno-$C_1$–$C_6$alkoxycarbonyl, $C_1$–$C_6$alkylaminocarbonyl, $C_1$–$C_4$alkoxyiminomethyl, di($C_1$–$C_6$alkyl)aminocarbonyl, where the alkyl groups can be identical or different; $C_1$–$C_6$alkylaminothiocarbonyl, di($C_1$–$C_6$alkyl)aminothiocarbonyl, where the alkyl groups can be identical or different; $C_1$–$C_6$alkylamino, di($C_1$–$C_6$alkyl)amino, where the alkyl groups can be identical or different; halogen, $NO_2$, CN, $SF_5$, thioamido, thiocyanatomethyl, trimethylsilyl; an unsubstituted or mono- to tetrasubstituted $C_1$–$C_4$alkylenedioxy group, where the substituents are chosen from the group consisting of $C_1$–$C_4$alkyl and halogen; aryl-Q—$C_1$–$C_6$alkyl, aryl-Q—$C_2$–$C_6$alkenyl, heterocyclyl-Q—$C_1$–$C_6$alkyl, heterocyclyl-Q—$C_2$–$C_6$alkenyl, or aryl-Q—$C_1$–$C_6$alkyl, aryl-Q—$C_2$–$C_6$alkenyl or hetercyclyl-Q—$C_2$–$C_6$alkenyl or heterocyclyl-Q—$C_2$–$C_6$alkenyl which are mono- to pentasubstituted in the aryl or heterocyclyl ring, depending on the possibility of substitution, where the substituents independently of one another are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, CN, nitro, OC(=O)—$C_1$–$C_6$alkyl, OH, $NH_2$ and $C_1$–$C_6$alkoxycarbonyl;
where, if q is greater than 1, the radicals $R_5$ can be identical or different;
Q is a direct bond, —CH(OH)—, —C(=O)— or —S(=O)$_v$—;
v is 0, 1 or 2;
$R_{10}$ is H, $C_1$–$C_6$alkyl, $C_2$–$C_8$alkenyl, $C_2$–$C_8$alkynyl, $C_3$–$C_6$cyloalkyl; or $C_1$–$C_6$alkyl, $C_2$–$C_8$alkenyl, $C_2$–$C_8$alkynyl or $C_3$–$C_6$cycloalkyl-, which are mono- or polysubstituted by substituents from the group consisting of halogen; —Si($C_1$–$C_4$alkyl)$_3$, where the alkyl groups can be identical or different; $C_1$–$C_6$alkoxycarbonyl, or an aryl or heteroyclyl group which are unsubstituted or mono- or polysubstituted by substituents from the group consisting of halogen, $C_1$–$C_4$alkyl and halogeno-$C_1$–$C_4$alkyl, and
p is 0, 1 or 2; and
(B) either
(I) n is 1 or 2 and q is 1, 2, 3 or, when n 1 is, 4; and
A, G, X, Y, Z, R, $R_2$, $R_3$, $R_4$, $R_5$, $R^7$ and $R_9$ are as defined above under (A); or
(II) n is 0;
q is 2, 3, 4 or 5; and
A, X, Y, Z, $R_2$, $R_3$, $R^4$, $R_5$, $R_7$ and $R_9$ are as defined above under (A); and the radicals $R_5$ can be identical or different; with the proviso that if q is 2, $(R_5)_2$ is not dichloro or dimethyl, and with the further proviso that $R_2$ is not $CH_3$ if $AR_7$ is $CH_3$ and $(R_5)_2$ is 3-fluoro, 5-$CF_3$ or, together, 3,4-methylenedioxy and $R_3$ and $R_4$ are H; or

3

(III) n is 0;

q is 1;

A, X, Y, Z, $R_2$, $R_3$, $R^4$, $R_7$ and $R_9$ are as defined above under (A); and $R_5$ is tert-butyl, $C_5$ . $C_6$alkyl, halogeno-$C_1$–$C_6$alkyl, with the exception of $CF_3$; $C_3$–$C_6$cycloalkyl, halogeno-$C_3$–$C_6$cycloalkyl, $C_5$–$C_6$alkoxy, halogeno-$C_3$–$C_6$alkoxy, $C_2$–$C_6$alkylthio, halogeno-$C_1$–$C_6$alkylthio, $C_1$–$C_6$alkylsulfinyl, halogeno-$C_1$–$C_6$alkylsulfinyl, $C_2$–$C_6$alkylsulfonyl, halogeno-$C_1$–$C_6$alkylsulfonyl, $C_1$–$C_6$alkylsulfonyloxy, halogeno-$C_1$–$C_6$alkylsulfonyloxy, $C_1$–$C_6$alkoxy-$C_1$–$C_6$alkyl, halogeno-$C_1$–$C_6$alkoxy-$C_1$–$C_6$alkyl, $C_1$–$C_6$alkylthio-$C_1$–$C_6$alkyl, halogeno-$C_1$–$C_6$alkylthio-$C_1$–$C_6$alkyl, $C_1$–$C_6$alkylsulfinyl-$C_1$–$C_6$alkyl, halogeno-$C_1$–$C_6$alkylsulfinyl-$C_1$–$C_6$alkyl, $C_1$–$C_6$alkylsulfonyl-$C_1$–$C_6$alkyl, halogeno-$C_1$–$C_6$alkylsulfonyl-$C_1$–$C_6$alkyl, $C_1$–$C_6$alkylcarbonyl, halogeno-$C_1$–$C_6$alkylcarbonyl, $C_2$–$C_6$alkoxycarbonyl, halogeno-$C_1$–$C_6$alkoxycarbonyl, $C_2$–$C_6$alkylaminocarbonyl, $C_1$–$C_4$alkoxyiminomethyl, di($C_2$–$C_6$alkyl)aminocarbonyl, where the alkyl groups can be identical or different; $C_1$–$C_6$alkylaminothiocarbonyl, di($C_1C_6$alkyl)aminothiocarbonyl, where the alkyl groups can be identical or different; $C_2$–$C_6$alkylamino, di($C_2C_6$alkyl)amino, where the alkyl groups can be identical or different; $SF_5$, thiocyanatomethyl, trimethylsilyl, aryl-Q—$C_1$–$C_6$alkyl, aryl-Q—$C_2$–$C_6$alkenyl, heterocyclyl-Q—$C_1$–$C_6$alkyl, heterocyclyl-Q—$C_2$–$C_6$alkenyl; or aryl-Q—$C_1$–$C_6$alkyl, aryl-Q—$C_2$–$C_6$alkenyl, heterocyclyl-Q—$C_{1-C6}$alkyl or heterocyclyl-Q—$C_2$–$C_6$alkenyl which are mono- to pentasubstituted in the aryl or heterocyclyl ring, depending on the possibility of substitution, where the substituents independently of one another are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, CN, nitro and $C_1$–$C_6$alkoxycarbonyl;

Q is a direct bond, —CH(OH)—, —C(=O)— or —S(=O)$_v$—;

v is 0, 1 or 2; or (IV) n is 1 and q is 0;

A, X, Y, Z, $R_2$, $R_3$, $R_4$, $R_7$ and $R_9$ are as defined above under (A);

G is O; and

R is n-propyl, n-butyl, sec-butyl, isobutyl, $C_3$–$C_6$cycloalkyl, $C_3$–$C_6$cycloalkyl-$C_1$–$C_4$alkyl, halogeno-$C_4$–$C_6$cycloalkyl-$C_1$–$C_4$alkyl, $C_1$–$C_4$alkylenyl-$C_3$–$C_6$cycloalkyl, $C_1$–$C_4$alkylenyl-halogeno-$C_3$–$C_6$cycloalkyl, $CH_2Si(C_1$–$C_4$alkyl)$_3$, where the alkyl groups can be identical or different; a substituted aryl or benzyl, where the substituents of the aryl or benzyl independently of one another are chosen from the group consisting of $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$alkylthio, phenoxy, CN and nitro; or a phenyl radical which is monosubstituted on two adjacent C atoms by an unsubstituted or mono- to tetrasubstituted $C_1$–$C_4$alkylenedioxy group, where the substituents are selected from the group consisting of $C_1$–$C_4$alkyl and halogen; with the proviso that OR is not n-propyloxy or

4

—$OCH_2Si(CH_3)_3$ in the 4-position if X is CH, Y is $OCH_3$, Z is O, $AR_7$ is $CH_3$, $R_2$ is $CH_3$ and $R_3$ and $R_4$ are H; and with the further proviso that R is not phenyl which is substituted by fluorine or chlorine in the 4-position or benzyl which is substituted by methyl or methoxy in the 4-position or monosubstituted by fluorine, chlorine, bromine or $CF_3$ in the 2-, 3- or 4-position if OR is in the p-position, $AR_7$ is $CH_3$, $R_2$ is $CH_3$ and $R_3$ and $R_4$ are H; or (V) n is 1;

q is 0;

A, X, Y, Z, R, $R_2$, $R_3$, $R_4$, $R_7$ and $R_9$ are as defined above under (A); and G is S;

with the proviso that R is not methyl if $R_2$ is methyl; or (VI) n is 1;

q is 0;

A, G, X, Y, Z, $R_2$, $R_3$, $R_4$ and $R_9$ are as defined above under (A);

A is a direct bond, $C_7$–$C_{10}$alkylene, —C(=O)—,—C(=S)— or halogeno-$C_1$–$C_{10}$alkylene and $R_7$ is a radical $R_{10}$; or A is $C_1$–$C_{10}$alkylene, —C(=O)—, —C(=S)— or halogeno-$C_1$–$C_{10}$alkylene; and $R_7$ is CN, O($C_1$–$C_4$alkyl)$_2$, or N($C_1$–$C_4$alkyl)$_2$, in which the two alkyl radicals can be identical or different, $OR_{10}$, $N(R_{10})_2$, where the radicals $R_{10}$ can be identical or different, or —S(=O$_p$)$R_{10}$;

$R_{10}$ is H; or $C_5$–$C_8$alkenyl, $C_4$–$C_8$alkynyl, $C_3$–$C_6$cycloalkyl; or $C_1$–$C_6$alkyl, $C_2$–$C_8$alkenyl, $C_2$–$C_8$alkynyl or $C_3$–$C_6$cycloalkyl which are mono- or polysubstituted by substituents from the group consisting of halogen; —$Si(C_1$–$C_4$alkyl)$_3$, where the alkyl groups can be identical or different; $C_1$–$C_6$alkoxycarbonyl, or an aryl or heterocyclyl group which are unsubstituted or mono- or polysubstituted by substituents from the group consisting of halogen, $C_1$–$C_4$alkyl and halogeno-$C_1$–$C_4$alkyl; and R is methyl, ethyl, t-butyl, or mono- or polysubstituted methyl, ethyl or t-butyl, where the substituents independently of one another are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$phenoxy, CN and nitro; or a phenyl radical which is monosubstituted on two adjacent C atoms by an unsubstituted or mono- to tetrasubstituted $C_1$–$C_4$alkylenedioxy group, where the substituents are selected from the group consisting of $C_1$–$C_4$alkyl and halogen; or $CH_2Si(C_1$–$C_4$alkyl)$_3$, where the alkyl groups can be identical or different; or (VII) n is 1;

q is 0;

A, G, X, Y, Z, $R_2$, $R_3$, $R_4$, $R_7$ and $R_9$ are as defined above under (A); and R is $C_2$–$C_4$alkenyl or $C_2$–$C_4$alkynyl which are substituted or unsubstituted, and where the substituents independently of one another are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$alkylthio, phenoxy, CN and nitro, with the proviso that $AR_7$ is not methyl if $R_2$ is methyl, $R_3$ and $R_4$ are H and G is oxygen;

and, where appropriate, their possible E/Z isomers, E/Z isomer mixtures and/or tautomers, in each case in the free form or in salt form, a process for the preparation and the use of these compounds, E/Z isomers and tautomers, pesticides, the active compound of which is chosen from these compounds, E/Z isomers and tautomers, and a process for the preparation and the use of these agents, intermediate products, and, where appropriate, their possible E/Z isomers, E/Z isomer mixtures and/or tautomers, in the free form or in salt form, for the preparation of these compounds, where appropriate tautomers, in the free form or in salt form, of these intermediate products and a process for the preparation and the use of these intermediate products and their tautomers.

A preferred compound of the formula (I) is that in which either

X is CH or N, Y is $OR_1$ and Z is O, or

X is N, Y is $NHR_8$ and Z is O, S or S(=O);

$R_1$ is $C_1$–$C_4$alkyl;

$R_2$ is H, $C_1$–$C_4$alkyl, halogeno-$C_1$–$C_4$alkyl, $C_3$–$C_6$cycloalkyl, $C_1$–$C_4$alkoxymethyl, $C_1$–$C_4$alkoxy, halogeno-$C_1$–$C_4$alkoxy, $C_1$–$C_4$alkylthio, halogeno-$C_1$–$C_4$alkylthio or CN;

$R_3$ and $R_4$ independently of one another are H, $C_1$–$C_4$alkyl, $C_1$–$C_4$alkoxy, OH, CN, $NO_2$, a $(C_1$–$C_4$alkyl$)_3$—Si group, where the alkyl groups can be identical or different, halogen, $(C_1$–$C_4$alkyl)S(=O)$_m$, (halogen-$C_1$–$C_4$ alkyl)S(=O)$_m$, halogeno-$C_1$–$C_4$alkyl or halogeno-$C_1$–$C_4$alkoxy;

$R_8$ is H or $C_1$–$C_4$alkyl;

$R_9$ is methyl, fluoromethyl or difluoromethyl;

m is 0, 1 or 2; n is 0 or 1; q is 0, 1, 2, 3 or 4 or, if n is 0, 5; either

A is a direct bond, $C_1$–$C_{10}$alkylene, —C(=O)—, —C(=S)— or halogeno-$C_1$–$C_{10}$alkylene and $R_7$ is a radical $R_{10}$ ; or A is $C_1$–$C_{10}$alkylene, —C(=O)—, —C(=S)— or halogeno-$C_1$–$C_{10}$alkylene and $R_7$ is —CN, $OR_{10}$, $N(R_{10})_2$, where the radicals $R_{10}$ can be identical or different, or —S(=$O_p$)$R_{10}$; preferably $OR_{10}$, $N(R_{10})_2$, where the radicals $R_{10}$ can be identical or different, or —S(=$O_p$)$R_{10}$;

R is a substituted or unsubstituted $C_1$–$C_4$alkyl or aryl group, where the substituents are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, CN and nitro;

$R_5$ is $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$alkylthio, $C_1$–$C_6$alkyl-sulfinyl, halogeno-$C_1$–$C_6$alkylsulfinyl, $C_1$–$C_6$alkylsulfonyl, halogeno-$C_1$–$C_6$alkylsulfonyl, $C_1$–$C_6$alkoxy-$C_1$–$C_6$alkyl, halogeno-$C_1$–$C_6$alkoxy-$C_1$–$C_6$alkyl, $C_1$–$C_6$alkylthio -$C_1$–$C_6$alkyl, halogeno-$C_1$–$C_6$alkylthio-$C_1$–$C_6$alkyl, $C_1$–$C_6$alkylsulfinyl-$C_1$–$C_6$alkyl, halogeno-$C_1$–$C_6$alkylsulfinyl-$C_1$–$C_6$alkyl, $C_1$–$C_6$alkylsulfonyl-$C_1$–$C_6$alkyl, halogeno-$C_1$–$C_6$alkylsulfonyl-$C_1$–$C_6$alkyl, $C_1$–$C_6$alkylcarbonyl, halogeno-$C_1$–$C_6$alkylcarbonyl, $C_1$–$C_6$alkoxycarbonyl, halogeno-$C_1$–$C_6$alkoxycarbonyl, $C_1$–$C_6$alkylaminocarbonyl, $C_1$–$C_4$alkoxyiminomethyl, di($C_1$–$C_6$alkyl)aminocarbonyl, where the alkyl groups can be identical or different;

$C_1$–$C_6$alkylaminothiocarbonyl, di($C_1$–$C_6$alkyl)aminothiocarbonyl, where the alkyl groups can be identical or different, $C_1$–$C_6$alkylamino, di($C_1$–$C_6$alkyl)amino, where the alkyl groups can be identical or different, halogen, $N_2$, CN, $SF_5$, thioamido, thiocyanatomethyl, trimethylsilyl or an unsubstituted or mono- to tetrasubstituted $C_1$–$C_4$alkylenedioxy group, where the substituents are chosen from the group consisting of $C_1$–$C_4$alkyl and halogen, and where, if q is greater than 1, the radicals $R_5$ can be identical or different;

$R_{10}$ is H, $C_1$–$C_6$alkyl which is unsubstituted or mono- or polysubstituted by substituents from the group consisting of halogen, $C_3$–$C_6$cycloalkyl which is unsubstituted or mono- or polysubstituted by substituents from the group consisting of halogen, $C_2$–$C_8$alkenyl which is unsubstituted or mono- or polysubstituted by substituents from the group consisting of halogen, $C_2$–$C_8$alkynyl which is unsubstituted or mono- or polysubstituted by substituents from the group consisting of halogen, —Si($C_1$–$C_4$alkyl)$_3$, where the alkyl groups can be identical or different, $C_1$–$C_6$alkoxycarbonyl or an aryl or heterocyclyl group which is unsubstituted or mono- or polysubstituted by substituents from the group consisting of halogen, $C_1$–$C_4$alkyl and halogeno-$C_1$–$C_4$alkyl; and G is O; p is 0, 1 or 2;

with the proviso that $R_7$ is other than H if A is methylene, and with the further proviso that $R_7$ is other than methyl if A is a direct bond;

or A–$R_7$ is $CH_3$ and either $R_5$ is halogen, $C_1$–$C_6$alkyl, halogeno-$C_1$–$C_6$alkyl, $C_3$–$C_6$cycloalkyl, halogeno-$C_3$–$C_6$cycloalkyl, or Si($C_1$–$C_4$alkyl, where the alkyl groups can be identical or different, and where the radicals $R_5$ are different;

q is 2, 3, 4 or 5; and n is 0; or $R_5$ is $C_4$–$C_6$alkyl, $C_3$–$C_6$cycloalkyl, halogeno-$C_3$–$C_6$cycloalkyl or Si($C_1$–$C_4$alkyl)$_3$, where the alkyl groups can be identical or different, q is 1; and n is 0; or R is n-propyl, n-butyl, sec-butyl, isobutyl, $C_1$–$C_4$alkylenyl-$C_3$–$C_6$cycloalkyl, $C_1$–$C_4$alkylenyl-halogeno-$C_3$–$C_6$cycloalkyl, $CH_2$Si($C_1$–$C_4$alkyl)$_3$, where the alkyl groups can be identical or different, or a substituted phenyl or benzyl group, where the substituents are chosen from the group consisting of halogen, $C_1$–$C_4$alkyl and halogeno-$C_1$–$C_4$alkyl;

$R_5$ is halogen;

q is 0, 1, 2, 3 or 4; and n is 1.

A compound of the formula (I) which is furthermore preferred is that in which either X is CH or N; Y is $OR_1$ and Z is O; or X is N; Y is $NHR_8$ and Z is O, S or S(=O);

$R_1$ is $C_1$–$C_4$alkyl;

$R_2$ is H, $C_1$–$C_4$alkyl, halogeno-$C_1$–$C_4$alkyl, $C_3$–$C_6$cycloalkyl, $C_1$–$C_4$alkoxymethyl, $C_1$–$C_4$alkoxy, halogeno-$C_l$–$C_4$alkoxy, $C_1$–$C_4$alkylthio, halogeno-$C_1$–$C_4$alkylthio or CN;

$R^3$ and $R_4$ independently of one another are H, $C_1$–$C_4$alkyl, $C_1$–$C_4$alkoxy, OH, CN, $NO_2$, a $(C_1$–$C_4$alkyl$)_3$—Si group, where the alkyl groups can be identical or different, halogen, $(C_1$–$C_4$alkyl)S(=O)$_m$, (halogeno-$C_1$–$C_4$alkyl)S(=O)$_m$, halogeno-$C_1$–$C_4$alkyl or halogeno-$C_1$–$C_4$alkoxy, $R_8$ is H or $C_1$–$C_4$alkyl;

$R_9$ is methyl, fluoromethyl or difluoromethyl;

m is 0, 1 or 2; n is 0 or 1; q is 0, 1, 2, 3, 4 or, if n is 0, 5;

G is O; and (a) A is a direct bond, $C_1$–$C_1$alkylene, —C(=O)—,—C(=S)— or halogeno-$C_1$–$C_{10}$alkylene and $R_7$ is a radical $R_{10}$; or (b) A is $C_1$–$C_{10}$alkylene, —C(=O)—,—C(=S)— or halogeno-$C_1$–$C_{10}$alkylene and $R_7$ is —CN, $OR_{10}$, $N(R_{10})_2$, where the radicals $R_{10}$ can be identical or different, or —S(=O$_p$)$R_{10}$; and in the groups (I) and (II), R is an unsubstituted or mono- or polysubstituted $C_1$–$C_4$alkyl, $C_2$–$C_4$alkenyl, $C_2$–$C_4$alkynyl, benzyl or aryl group, where the substituents are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$alkylthio, phenoxy, CN and nitro; or $CH_2Si(C_1$–$C_4$alkyl$)_3$, where the alkyl groups can be identical or different; or a phenyl radical which is monosubstituted on two adjacent C atoms by a —O—$CH_2$—O— group; and $R_5$ is $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$alkylthio, $C_1$–$C_6$alkylsulfinyl, halogeno-$C_1$–$C_6$alkylsulfinyl, $C_1$–$C_6$alkylsulfonyl, halogeno-$C_1$–$C_6$alkylsulfonyl, $C_1$–$C_6$alkylsulfonyloxy, halogeno-$C_1$–$C_6$alkylsulfonyloxy, $C_1$–$C_6$alkoxy-$C_1$–$C_6$alkyl, halogeno-$C_1$–$C_6$alkoxy-$C_1$–$C_6$alkyl, $C_1$–$C_6$alkylthio-$C_1$–$C_6$alkyl, halogeno-$C_1$–$C_6$alkylthio-$C_1$–$C_6$alkyl, $C_1$–$C_6$alkylsulfinyl-$C_1$–$C_6$alkyl, halogeno-$C_1$–$C_6$alkylsulfinyl-$C_1$–$C_6$alkyl, $C_1$–$C_6$alkylsulfonyl-$C_1$–$C_6$alkyl, halogeno-$C_1$–$C_6$alkylsulfonyl-$C_1$–$C_6$alkyl, $C_1$–$C_6$alkylcarbonyl, halogeno-$C_1$–$C_6$alkylcarbonyl, $C_1$–$C_6$alkoxycarbonyl, halogeno-$C_1$–$C_6$alkoxycarbonyl, $C_1$–$C_4$alkylaminocarbonyl, $C_1$–$C_4$alkoxyiminomethyl, di($C_1$–$C_6$alkyl)aminocarbonyl, where the alkyl groups can be identical or different, $C_1$–$C_6$alkylaminothiocarbonyl, di($C_1$–$C_6$alkyl)aminothiocarbonyl, where the alkyl groups can be identical or different, $C_1$–$C_6$alkylamino, di($C_1$–$C_6$alkyl)amino, where the alkyl groups can be identical or different, halogen, $NO_2$, CN, $SF_5$, thioamido, thiocyanatomethyl, trimethylsilyl, an unsubstituted or mono- to tetrasubstituted $C_1$–$C_4$alkylenedioxy group, where the substituents are chosen from the group consisting of $C_1$–$C_4$alkyl and halogen; aryl-Q—$C_1$–$C_6$alkyl, aryl-Q—$C_2$–$C_6$alkenyl, heterocyclyl-Q—$C_1$–$C_6$alkyl, heterocyclyl-Q—$C_2$–$C_6$alkenyl, or aryl-Q—$C_1$–$C_6$alkyl, aryl-Q—$C_2$–$C_6$alkenyl, heterocyclyl-Q—$C_1$–$C_6$alkyl or hetercyclyl-Q—$C_2$–$C_6$alkenyl which are mono- to pentasubstituted in the aryl or heterocyclyl ring, depending on the possibility of substitution, where the substituents independently of one another are chosen from the group consisting of halogen, $C_1$–$C_6$alkyl, halogeno-$C_1$–$C_6$alkyl, $C_3$–$C_6$cycloalkyl, halogeno-$C_3$–$C_6$-cycloalkyl, $C_1$–$C_6$alkoxy, halogeno-$C_1$–$C_6$alkoxy, CN, nitro and $C_1$–$C_6$alkoxycarbonyl;

and where, if q is greater than 1, the radicals $R_5$ can be identical or different;

Q is a direct bond, —CH(OH)—; —C(=O)— or —S(=O)$_v$—; preferably a direct bond, —CH(OH)— or —C(=O)—, v is 0, 1 or 2;

$R_{10}$ is H, $C_1$–$C_6$alkyl which is unsubstituted or mono- or polysubstituted by substituents from the group consisting of halogen, $C_3$–$C_6$cycloalkyl which is unsubstituted or mono- or polysubstituted by substituents from the group consisting of halogen, $C_2$–$C_6$alkenyl which is unsubstituted or mono- or polysubstituted by substituents from the group consisting of halogen, $C_2$–$C_8$alkynyl which is unsubstituted or mono- or polysubstituted by substituents from the group consisting of halogen, —Si($C_1$–$C_4$alkyl$)_3$, where the alkyl groups can be identical or different, $C_1$–$C_6$alkoxycarbonyl or an aryl or heterocyclyl group which is unsubstituted or mono- or polysubstituted by substituents from the group consisting of halogen, $C_1$–$C_4$alkyl and halogeno-$C_1$–$C_4$alkyl, and p is 0, 1 or 2;

with the proviso that A–$R_7$ is other than $CH_3$; or

A—$R_7$ in the following groups (c) to (k) is $CH_3$ and X, Y, Z, $R_1$, $R_2$, $R_3$, $R_4$, $R_8$, $R_9$ and m are as defined above under (C), and either, (c) $R_5$ is halogen, $C_1$–$C_6$alkyl, halogeno-$C_1$–$C_6$alkyl, $C_3$–$C_6$cycloalkyl, halogeno-$C_3$–$C_6$cycloalkyl or Si($C_1$–$C_4$alkyl), where the alkyl groups can be identical or different, and where the radicals $R_5$ are different;

q is 2, 3, 4 or 5; and n is 0; or (d) $R_5$ is $C_4$–$C_6$alkyl, $C_3$–$C_6$cycloalkyl, halogeno-$C_3$–$C_6$cycloalkyl or Si($C_1$–$C_4$alkyl$)_3$, where the alkyl groups can be identical or different, q is 1; and n is 0; or (e) R is n-propyl, n-butyl, sec-butyl, isobutyl, $C_3$–$C_6$cycloalkyl, $C_3$–$C_6$cycloalkyl-$C_1$–$C_4$alkyl, halogeno-$C_3$–$C_6$cycloalkyl-$C_1$–$C_4$alkyl, $C_1$–$C_4$alkylenyl-$C_3$–$C_6$cycloalkyl, $C_1$–$C_4$alkylenyl-halogeno-$C_3$–$C_6$cycloalkyl, $CH_2Si(C_1$–$C_4$alkyl$)_3$, where the alkyl groups can be identical or different, or a substituted phenyl or benzyl group, where the substituents are chosen from the group consisting of halogen, $C_1$–$C_4$alkyl and halogeno-$C_1$–$C_4$alkyl;

$R_5$ is halogen;

q is 0, 1, 2, 3 or 4; and n is 1;

with the proviso that OR is not m-$CF_3$-benzyloxy in the p-position if X is CH, Y is $OCH_3$, Z is O, $R_2$ is $CH_3$, $R_3$ and $R_4$ are hydrogen, $R_9$ is $CH_3$, n is 1 and q is 0; or (f) R is an unsubstituted or mono- or polysubstituted $C_1$–$C_4$alkyl, $C_2$–$C_4$alkenyl, $C_2$–$C_4$alkynyl, benzyl or aryl group, where the substituents are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-C $C_1$–$C_6$alkylthio, CN and nitro; or —$CH_2Si(C_1$–$C_4$alkyl$)_3$, where the alkyl groups can be identical or different; or a phenyl radical which is monosubstituted on to two adjacent C atoms by a —O—$CH_2$—O— group;

$R_5$ is aryl-Q—$C_1$–$C_6$alkyl, aryl-Q—$C_1$–$C_6$alkenyl, heterocyclyl-Q—$C_1$–$C_6$alkyl, heterocyclyl-Q—$C_2$–$C_6$alkenyl, or aryl-Q—$C_1$–$C_6$alkyl, aryl-Q—$C_2$–$C_6$alkenyl, heterocyclyl-Q—$C_1$–$C_6$alkyl or heterocyclyl-Q—$C_2$–$C_6$alkenyl which are mono- to pentasubstituted in the aryl or heterocyclyl ring, depending on the possibility of substitution, where the substituents independently of one another are chosen from the group consisting of halogen, $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, CN, nitro and $C_1$–$C_6$alkoxycarbonyl;

where, if q is greater than 1, the radicals $R_5$ can be identical or different;

Q is a direct bond, —CH(OH)—; or —C(=O)—;

q is 1, 2, 3 or 4; and n is 0 or 1, where if q is 2, 3 or 4, one or more of the radicals $R_5$ also independently of one another can be $C_1$–$C_6$alkyl, halogeno-$C_1$–$C_6$alkyl, $C_3$–$C_6$cycloalkyl, halogeno-$C_3$–$C_6$cycloalkyl, $C_1$–$C_6$alkoxy, halogeno-$C_1$–$C_6$alkoxy, $C_1$–$C_6$alkylthio, halogeno-$C_1$–$C_6$alkylthio, $C_1$–$C_6$alkylsulfinyl, halogeno-$C_1$–$C_6$alkylsulfinyl, $C_1$–$C_6$alkylsulfonyl, halogeno-$C_1$–$C_6$alkylsulfonyl, $C_1$–$C_6$alkoxy-$C_1$–$C_6$alkyl, halogeno-$C_1$–$C_6$alkoxy-$C_1$–$C_6$alkyl, $C_1$–$C_6$alkylthio-$C_1$–$C_6$alkyl, halogeno-$C_1$–$C_6$alkylthio-$C_1$–$C_6$alkyl, $C_1$–$C_6$alkylsulfinyl-$C_1$–$C_6$alkyl, halogeno-$C_1$–$C_6$alkylsulfinyl-$C_1$–$C_6$alkyl, $C_1$–$C_6$alkylsulfonyl-$C_1$–$C_6$alkyl, halogeno-$C_1$–$C_6$alkylsulfonyl-$C_1$–$C_6$alkyl, $C_1$–$C_6$alkylcarbonyl, halogeno-$C_1$–$C_6$alkylcarbonyl, $C_1$–$C_6$alkoxycarbonyl, halogeno-$C_1$–$C_6$alkoxycarbonyl, $C_1$–$C_6$alkylaminocarbonyl, $C_1$–$C_4$alkoxyiminomethyl, di($C_1$–$C_6$alkyl)aminocarbonyl, where the alkyl groups can be identical or different, $C_1$–$C_6$alkylaminothiocarbonyl, di($C_1$–$C_6$alkyl)aminothiocarbonyl, where the alkyl groups can be identical or different, $C_1$–$C_6$alkylamino, di($C_1$–$C_6$alkyl)amino, where the alkyl groups can be identical or different, halogen, $NO_2$, CN, $SF_5$, thioamido, thiocyanatomethyl, trimethylsilyl or a $C_1$–$C_4$alkylenedioxy group which is unsubstituted or mono- to tetrasubstituted, where the substituents are chosen from the group consisting of $C_1$–$C_4$alkyl and halogen; or (g) R is $C_3$–$C_6$cycloalkyl, halogeno-$C_3$–$C_6$cycloalkyl or an unsubstituted or mono- or polysubstituted phenyl or benzyl group, where the substituents are chosen from the group consisting of halogen, $C_1$–$C_4$alkyl and halogeno-$C_1$–$C_4$alkyl, $R_5$ is $C_1$–$C_6$alkyl, $C_1$–$C_6$alkoxy, halogeno-$C_1$–$C_6$alkyl or halogeno-$C_1$–$C_6$alkoxy;

q is 1 and n is 1, or (h) R is $C_{3-C6}$cycloalkyl-$C_1$–$C_4$alkyl or halogeno-$C_3$–$C_6$cycloalkyl-$C_1$–$C_4$alkyl, $R_5$ is $C_1$–$C_6$alkyl, $C_1$–$C_6$alkoxy, halogeno-$C_1$–$C_6$alkyl or halogeno-$C_1$–$C_6$alkoxy;

q is 1 and n is 1, or (i) R is methyl, ethyl, isopropyl or tert-butyl;

$R_5$ is $C_1$–$C_6$alkyl, $C_1$–$C_6$alkoxy, halogeno-$C_1$–$C_6$alkyl, halogeno-$C_1$–$C_6$alkoxy or halogen;

q is 1; and n is 1; or (k) R is n-propyl;

$R_5$ is $C_1$–$C_6$alkyl or $C_1$–$C_6$alkoxy;

q is 1; and n is 1;

and, where appropriate, its possible E/Z isomers, E/Z isomer mixtures and/or tautomers, in each case in the free form or in salt form.

Certain methoxyacrylic add derivatives are proposed as active compounds in pesticides in the literature. However, the biological properties of these known compounds are not completely satisfactory in the field of pest control, and for this reason there is the need to provide further compounds having pest control properties, in particular for control of insects and representatives of the order Acarina, and in particular for control of phytopathogenic microorganisms, this object being achieved according to the invention by providing the present compounds of the formula (I).

Some of the compounds of the formula (I) and of the formulae (III), (IV) and (VI) defined below contain asymmetric carbon atoms, which means that the compounds can occur in an optically active form. Because of the presence of the C=X and the oximino double bonds, the compounds can occur in the E and Z isomer forms. Atropisomers of the compounds can furthermore occur. The formulae (I), (III), (IV) and (VI) are intended to include all these possible isomeric forms and mixtures thereof, for example racemates or E/Z isomer mixtures, and, where appropriate, the salts thereof, even though this is not mentioned specifically each time.

Unless defined otherwise, the general terms used above and below are as defined below. Unless defined otherwise, carbon-containing groups and compounds in each case contain 1 up to and including 8, preferably 1 up to and including 6, in particular 1 up to and including 4, especially 1 or 2, carbon atoms.

Alkyl—as a group per se and as a structural element of other groups and compounds, such as of halogenoalkyl, alkoxy, alkylthio, alkylsulfinyl, alkylsulfonyl, alkylcarbonyl, alkoxycarbonyl, alkylamino, alkoxyiminomethyl, alkylaminocarbonyl and alkylaminothiocarbonyl—is, in each case under due consideration of the number, embraced from case to case, of the carbon atoms contained in the corresponding group or compound, either straight-chain, i.e. methyl, ethyl, propyl, butyl, pentyl or hexyl, or branched, for example isopropyl, isobutyl, sec-butyl, tert-butyl, isopentyl, neopentyl or isohexyl.

Alkenyl—as a group per se and as a structural element of other groups and compounds, such as of halogenoalkenyl—is, in each case under due consideration of the number, embraced from case to case, of the carbon atoms contained in the corresponding group or compound, either straight-chain, for example vinyl, 1-methylvinyl, allyl, 1-butenyl or 2-hexenyl, or branched, for example isopropenyl.

Alkynyl—as a group per se and as a structural element of other groups and compounds, such as of halogenoalkynyl—is, in each case under due consideration of the number, embraced from case to case, of the carbon atoms contained in the corresponding group or compound, either straight-chain, for example propargyl, 2-butinyl or 5-hexinyl, or branched, for example 2-ethinylpropyl or 2-propargylisopropyl.

$C_3$–$C_6$cycloalkyl is cyclopropyl, cyclobutyl, cyclopentyl or cyclohexyl.

Alkylene—as a group per se and as a structural element of other groups and compounds, such as of halogenoalkylene—is, in each case under due consideration of the number, embraced from case to case, of carbon atoms contained in the corresponding group or compound, either straight-chain, for example —$CH_2CH_2$—, —$CH_2CH_2CH_2$— or —$CH_2CH_2CH_2CH_2$—, or branched, for example —CH($CH_3$)—, —CH($C_2H_5$)—, —C($CH_3$)$_2$—, —CH($CH_3$)$CH_2$— or —CH($CH_3$)CH($CH_3$)—.

Aryl is phenyl or naphthyl, in particular phenyl.

Heterocyclyl is a 5- to 7-membered aromatic or non-aromatic ring having 1 to 3 heteroatoms, which are chosen from the group consisting of N, O and S. Aromatic 5- and 6-membered rings which contain a nitrogen atom as the heteroatom and if appropriate a further heteroatom, preferably nitrogen or sulfur, in particular nitrogen, are preferred. Preferred heteroaryl radicals in the radical $R_5$ are -pyrazinyl, -pyrid-3'-yl, -pyrid-2'-yl, -pyrid-4'-yl, -pyrimidin-2'-yl, -pyrimidin4'-yl, -pyrimidin-5'-yl, -thiazol-2'-yl, -oxazol-2'-yl, -thien-2'yl, -thien-3'-yl and -thiazol-2'-yl.

Halogen—as a group per se and as a structural element of other groups and compounds, such as of halogenoalkyl, halogenoalkenyl and halogenoalkynyl—is fluorine, chlorine, bromine or iodine, in particular fluorine, chlorine or bromine, especially fluorine or chlorine, and very particularly fluorine.

Halogen—substituted carbon-containing groups and compounds, such as halogenoalkyl, halogenoalkenyl or halogenoalkynyl, can be partly halogenated or perhalogenated, and in the case of polyhalogenation, the halogen substituents can be identical or different. Examples of halogenoalkyl—as a group per se and as a structural element of other groups and compounds, such as of halogenoalkenyl—are methyl which is mono- to trisubstituted by fluorine, chlorine and/or bromine, such as $CHF_2$ or $CF_3$; ethyl which is mono- to penta-substituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; and butyl or one of its isomers which is mono- to nonasubstituted by fluorine, chlorine and/or bromine, such as $CF(CF_3)CHFCF_3$ or $CH_2(CF_2)_2CF_3$. Halogenoalkenyl is, for example, $CH_2CH=CHCl$, $CH_2CH=CCl_2$, $CH_2CF=CF_2$ or $CH_2CH=CHCH_2Br$. Halogenoalkynyl, is for example, $CH_2C\equiv CF$, $CH_2C\equiv CCH_2Cl$ or $CF_2CF_2C\equiv CCH_2F$.

Some compounds of the formula (I) and of the formulae (III), (IV) and (VI) defined below can, as is familiar to the expert, exist as tautomers, in particular if $R_7$ is H. The compounds of the formulae (I), (III), (IV) and (VI) above and below are therefore to be understood as also meaning corresponding tautomers, although the latter are not mentioned specifically in each case.

Compounds of the formula (I) and of the formulae (III), (IV) and (VI) defined below which have at least one basic center can form, for example, acid addition salts. These are formed, for example, with strong inorganic acids, such as mineral acids, for example perchloric acid, sulfuric acid, nitric acid, nitrous acid, a phosphoric acid or a hydrogen halide acid, with strong organic carboxylic acids, such as $C_1$–$C_4$alkanecarboxylic acids which are unsubstituted or substituted, for example by halogen, for example acetic acid, such as saturated or unsaturated dicarboxylic acids, for example oxalic, malonic, succinic, maleic, fumaric or phthalic acid, such as hydroxycarboxylic acids, for example ascorbic, lactic, malic, tartaric or citric acid, or such as benzoic acid, or with organic sulfonic acids, such as $C_1$–$C_4$alkane- or arylsulfonic acids which are unsubstituted or substituted, for example by halogen, for example methane- or p-toluenesulfonic acid. Compounds of the formula (I) with at least one acid group can furthermore form salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethylpropylamine, or a mono-, di- or trihydroxy-lower alkylamine, for example mono-, di- or triethanolamine. Where appropriate, corresponding inner salts can furthermore be formed. Agrochemically advantageous salts are preferred in the context of the invention; However, the invention also relates to salts which have disadvantages for agrochemical uses, for example salts which are toxic to bees or fish, which are employed, for example, for isolation or purification of free compounds of the formula (I) or agrochemically usable salts thereof. As a result of the close relationship between the compounds of the formula (I) in the free form and in the form of their salts, free compounds of the formula (I) or their salts above and below are accordingly and appropriately also to be understood as meaning the corresponding salts or, respectively, free compounds of the formula (I), where appropriate. The same applies to tautomers of compounds of the formulae (I), (III), (IV) and (VI) and salts thereof. In general, in each case the free form is preferred.

Preferred embodiments in the context of the invention—in each case taking into consideration the above provisos—are:

(1) a compound of the formula (I) in which X is CH;
(2) a compound of the formula (I), in which Y is $OR_1$, preferably $C_1$–$C_2$alkoxy, in particular methoxy;
(3) a compound of the formula (I), in which Z is O;
(4) a compound of the formula (I), in which $R_1$ is $C_1$–$C_2$alkyl;
(5) a compound of the formula (I), in which $R_2$ is H, $C_1$–$C_4$alkyl, halogeno-$C_1$–$C_4$alkyl or $C_3$–$C_6$cycloalkyl, preferably $C_1$–$C_4$alkyl or halogeno-$C_1$–$C_4$alkyl, in particular $C_1$–$C_2$alkyl, especially methyl;
(6) a compound of the formula (I), in which $R_3$ is H, $C_1$–$C_4$alkyl, $C_1$–$C_4$alkoxy, OH, CN, $NO_2$, halogen, halogeno-$C_1$–$C_4$alkyl or halogeno-$C_1$–$C_4$alkoxy, preferably H, $C_1$–$C_4$alkyl, $C_1$–$C_4$alkoxy or halogen, in particular H, methyl, methoxy, chlorine or fluorine, especially H;
(7) a compound of the formula (I), in which $R_4$ is H, $C_1$–$C_4$alkyl, $C_1$–$C_4$alkoxy, OH, CN, $NO_2$, halogen, halogeno-$C_1$–$C_4$alkyl or halogeno-$C_1$–$C_4$alkoxy, preferably H, $C_1$–$C_4$alkyl, $C_1$–$C_4$alkoxy or halogen, in particular H, methyl, methoxy, chlorine or fluorine, especially H;
(8) a compound of the formula (I), in which $R_8$ is H or $C_1$–$C_2$alkyl, preferably $C_1$–$C_2$alkyl, in particular methyl;
(9) a compound of the formula (I), in which $R_9$ is methyl or fluoromethyl, preferably methyl;
(10) a compound of the formula (I), in which m is 0 or 2, preferably 2;
(11) a compound of the formula (I), in which n is 1 or 2, preferably 1;
(12) a compound of the formula (I), in which n is 1 and q is 0;
(13) a compound of the formula (I), in which $AR_7$ is ethyl, n is 1 and q is 0;
(14) a compound of the formula (I), in which $AR_7$ is methyl, n is 0 and q is 2.
(15) a compound of the formula (I), in which G is oxygen;
(16) a compound of the formula (I), in which n is 1 and q is 1 or 2; preferably and n is 1 q is 1;
(17) a compound of the formula (I), in which A is a direct bond, $C_1$–$C_{10}$alkylene, or halogeno-$C_1$–$C_{10}$alkylene, preferably a direct bond or $C_1$–$C_4$alkylene, in particular a direct bond or methylene, and $R_7$ is a radical $R_{10}$;
(18) a compound of the formula (I), in which $AR_7$ is $C_1$–$C_4$alkyl, $C_3$alkenyl, which is optionally substituted with chlorine; or $C_3$alkenyl; preferably methyl or ethyl; in particular ethyl; in particular methyl;

(19) n is 1, q is 0, and R is a substituted aryl- or benzyl-group, where the substituents are chosen from the group consisting of halogen, $C_1$–$C_4$alkyl, halogeno-$C_1$–$C_4$alkyl, $C_3$–$C_6$cycloalkyl and halogeno-$C_3$–$C_6$cycloalkyl, or $CH_2Si(CH_3)_3$, preferably a substituted phenyl or benzyl group, where the substituents are chosen from the group consisting of halogen, $C_1$–$C_4$alkyl and halogeno-$C_1$–$C_4$alkoxy, in particular halogen, methyl and halogenomethyl, especially chlorine and trifluoromethyl;

(20) a compound of the formula (I), in which n is 1, q is 0 and OR is in the para-position;

(21) a compound of the formula (I), in which A is a direct bond, $C_1$–$C_{10}$alkylene, or halogeno-$C_1$–$C_{10}$alkylene, preferably a direct bond or $C_1$–$C_4$alkylene, in particular a direct bond or methylene; and $R_7$ is $C_1$–$C_4$alkyl which is unsubstituted or mono- to trisubstituted by substituents from the group consisting of hydrogen, $C_3$–$C_6$cycloalkyl which is unsubstituted or mono- or disubstituted by substituents from the group consisting of halogen, $C_2$–$C_4$alkenyl which is unsubstituted or mono- or trisubstituted by substituents from the group consisting of halogen, $C_2$–$C_4$alkynyl which is unsubstituted or mono- or disubstituted by substituents from the group consisting of halogen, —$Si(CH_3)_3$, $C_1$–$C_4$alkoxycarbonyl, or an aryl group which is unsubstituted or mono- or disubstituted by substituents from the group consisting of halogen, $C_1$–$C_4$alkyl and halogeno-$C_1$–$C_4$alkyl, preferably unsubstituted $C_1$–$C_4$alkyl, cyclopropyl which is disubstituted by substituents from the group consisting of halogen, $C_2$–$C_3$alkenyl which is disubstituted by substituents from the group consisting of halogen, unsubstituted $C_2$–$C_3$alkynyl, —$Si(CH_3)_3$, $C_1$–$C_4$alkoxycarbonyl, or a phenyl group which is monosubstituted by substituents from the group consisting of halogen, $C_1$–$C_2$alkyl and halogeno-$C_1$–$C_4$alkyl, in particular unsubstituted $C_1$–$C_3$alkyl, cyclopropyl which is disubstituted by chlorine, vinyl which is disubstituted by chlorine, acetylenyl, —$Si(CH_3)_3$, ethoxycarbonyl or trifluorophenyl;

(22) a compound of the formula (I), in which A—$R_7$ is $CH_3$, $R_5$ is halogen, $C_1$–$C_4$alkyl, $C_1$–$C_4$alkoxy, halogeno-$C_1$–$C_4$alkyl, $C_3$–$C_6$cycloalkyl or $Si(CH_3)_3$, preferably halogen, $C_1$–$C_2$alkyl or $C_1$–$C_4$alkoxy, in particular chlorine, fluorine, methyl or $C_1$–$C_3$alkoxy; especially fluorine, methyl or $C_1$–$C_2$alkoxy, and where the radicals $R_5$ are in each case identical or different, in particular different; and q is 2 or 3, preferably 2; and n is 0;

(23) a compound of the formula (I), in which A—$R_7$ is $CH_3$, $R_5$ is $C_3$–$C_6$cycloalkyl, halogeno-$C_3$–$C_6$cycloalkyl or $Si(CH_3)_3$, preferably $C_3$–$C_6$cycloalkyl or $Si(CH_3)_3$, in particular cyclopropyl or $Si(CH_3)_3$, and q is 1; and n is 0;

(24) a compound of the formula (I), in which A—$R_7$ is $CH_3$; R is n-propyl, n-butyl, sec-butyl, isobutyl, $C_3$–$C_6$cycloalkyl, $C_1$–$C_2$alkylenyl-halogeno-$C_3$–$C_6$cycloalkyl or $CH_2Si(CH_3)_3$; preferably n-butyl, sec-butyl, isobutyl or cyclopentyl; and n is 1 and q is 0;

(25) a compound of the formula (I), in which X is CH; Y is $C_1$–$C_2$alkoxy; Z is O; A is a direct bond or methylene; $R_2$ and $R_9$ are methyl; $R_3$ and $R_4$ are H; n is 1; q is 1 or 2; $R_7$ is a radical $R_{10}$; R is a substituted aryl group, where the substituents are chosen from the group consisting of halogen, methyl and halogenomethyl; and $R_{10}$ is H, unsubstituted $C_1$–$C_4$alkyl, cyclopropyl which is disubstituted by substituents from the group consisting of halogen, $C_2$–$C_3$alkenyl which is disubstituted by substituents from the group consisting of halogen, unsubstituted $C_2$–$C_3$alkynyl, —$Si(CH_3)_3$, $C_1$–$C_4$alkoxycarbonyl, or a phenyl group which is monosubstituted by substituents from the group consisting of halogen, $C_1$–$C_2$alkyl and halogeno-$C_1$–$C_4$alkyl;

(26) a compound of the formula (I), in which X is CH; Y is $C_1$–$C_2$alkoxy; Z is O; $R_2$ and $R_9$ are methyl; $R_3$ and $R_4$ are H; n is 0; q is 2; A—$R_7$ is $CH_3$; and $R_5$ is chlorine, fluorine, methyl, halogenomethyl or $C_1$–$C_4$alkoxy, especially where the radicals $R_5$ are different;

(27) a compound of the formula (I), in which X is CH; Y is $C_1$–$C_2$alkoxy Z is O; $R_2$ and $R_9$ are methyl; $R_3$ and $R_4$ are H; n is 1; q is 1 or 2; R is a substituted phenyl benzyl group, where the substituents are chosen from the group consisting of fluorine, chlorine, bromine, methyl and halogenomethyl, and $R_5$ is fluorine or chlorine;

(28) a compound of X formula (I), in which n is 0, q is 1, Q is a direct bond and $R_5$ is phenyl-ethyl, phenyl-ethenyl, heteroaryl-ethyl or heteroaryl-ethenyl, or phenyl-ethyl, phenyl-ethenyl, heteroaryl-ethyl or heteroaryl-ethenyl which is mono- to trisubstituted in the phenyl or heteroaryl ring, depending on the possibility of substitution, where the substituents independently of one another are chosen from the group consisting of fluorine, chlorine, bromine, $C_1$–$C_2$alkyl, halogenomethyl, methoxy, halogenomethoxy and $C_1$–$C_2$alkoxycarbonyl;

(29) a compound of the formula (I), in which A—$R_7$ is methyl or ethyl, R is $C_3$–$C_6$cycloalkyl-$CH_2$— or halogeno-$C_3$–$C_6$cycloalkyl-$CH_2$—, $R_5$ is $C_1$–$C_2$alkyl, $C_1$–$C_2$alkoxy or halogen and q is 1 and n is 1;

(30) a compound of the formula (I), in which A—$R_7$ is $CH_3$, R is methyl, ethyl, isopropyl or tert-butyl; $R_5$ is $C_1$–$C_4$alkyl, $C_1$–$C_4$alkoxy, fluorine or chlorine; q is 1; and n is 1;

(31) a compound of the formula (I), in which A—$R_7$ is $CH_3$, R is n-propyl; $R_5$ is $C_1$–$C_4$alkyl or $C_1$–$C_4$alkoxy; q is 1; and n is 1;

(32) X is CH; Y is $C_1$–$C_2$alkoxy,; Z is O; $R_2$ and $R_9$ are methyl; $R_3$ and $R_4$are H; n is 1; q is 1 or 2; R is methylenedichlorocyclopropyl or a substituted phenyl or benzyl group, where the substituents are chosen from the group consisting of fluorine, chlorine, bromine, methyl and halogenomethyl; and $R_5$ is fluorine or chlorine;

(33) $AR_7$ is methyl or ethyl, n is 1, q is 0, and R is $CH_2Si(CH_3)_3$ or a substituted aryl or benzyl group, where the substituents are chosen from the group consisting of halogen, $C_1$–$C_4$alkyl, halogeno-$C_1$–$C_4$alkyl, $C_3$–$C_6$cycloalkyl and halogeno-$C_3$–$C_6$cycloalkyl.

(36) a compound of the formula

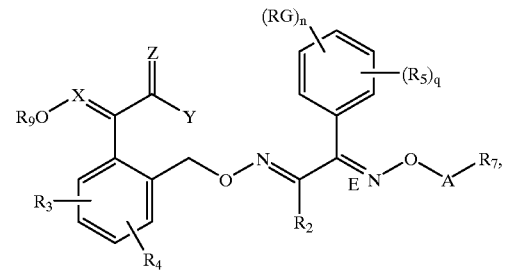

(Ia)

wherein the C=N double bond marked with E has the E configuration;

(37) (2-{2-[4-(2,2-Dichloro-cyclopropylmethoxy)-3-fluoro-phenyl]-2-methoxyimino-1-methyl-ethylideneaminooxymethyl}-phenyl)-3-methoxy-acrylic acid methyl ester (compound 1.3);

(38) Methoxyimino-(2-{2-methoxyimino-1-methyl-2-[4-(3-trifluoromethyl-phenoxy)-phenyl]-

(39) (2-{2-[3,5-Difluoro-4-(3-trifluoromethyl-benzyloxy)-phenyl]-2-methoxyimino-1-methyl-ethylideneaminooxymethyl}-phenyl)-3-methoxy-acrylic acid methyl ester (compound 1.11);

(40) 2-Methoxyimino-2-(2-{2-methoxyimino-1-methyl-2-[4-(3-trifluoromethyl-phenoxy)-phenyl]-ethylideneaminooxymethyl}-phenyl)-N-methyl-acetamide (compound 3.31);

(41) [2-(2-{4-[2-(3,5-Bis-trifluoromethyl-phenyl)-ethyl]-phenyl}-2-methoxyimino-1-methyl-ethylideneaminooxymethyl)-phenyl]-3-methoxy-acrylic acid methyl ester (compound 155.6);

(42) 3-Methoxy-2-[2-(2-methoxyimino-1-methyl-2-{4-[2-(3-trifluoromethyl-phenyl)-ethyl]-phenyl}-ethylideneaminooxymethyl)-phenyl]-acrylic acid methyl ester (compound 155.7);

(43) (2-{2-[4-(2,2-Dichloro cyclopropylmethoxy)-2,5-difluoro-phenyl]-2-methoxyimino-1-methyl-ethylideneaminooxymethyl}-phenyl)-3-methoxy-acrylic acid methyl ester (compound 1.13);

(44) (2-{2-[2,5-Difluoro-4-(3-trifluoromethyl-benzyloxy)-phenyl]-2-methoxyimino-1-methyl-ethylideneaminooxymethyl}-phenyl)-3-methoxy-acrylic acid methyl ester (compound 1.14);

(45) 3-Methoxy-2-[2-(1-{methoxyimino-[4-(3-trifluoromethyl-benzyloxy)-phenyl]-methyl}-propylideneaminooxymethyl)-phenyl]acrylic acid methyl ester (compound 1.25);

(46) [2-(1-{[4-(4-Fluoro-benzyloxy)-phenyl]-methoxyimino-methyl}-propylideneaminooxymethyl)-phenyl]-3-methoxy-acrylic acid methyl ester (compound 1.66)

(47) [2-(2-{4-[2-(2,4-Dichloro-phenyl)-ethyl]-phenyl}-2-methoxyimino-1-methyl-ethylideneaminooxymethyl)-phenyl]-3-methoxy-acrylic acid methyl ester (compound 155.3);

(48) (2-{2-[4-(4-Bromo-phenoxy)-phenyl]-2-methoxyimino-1-methyl-ethylideneaminooxymethyl}-phenyl)-3-methoxy-acrylic acid methyl ester (compound 1.41);

(49) (2-{2-[2-Fluoro-4-(3-trifluoromethyl-benzyloxy)-phenyl]-2-methoxyimino-1-methyl-ethylideneaminooxymethyl}-phenyl)-3-methoxy-acrylic acid methyl ester (compound 1.7);

(50) (2-{2-Allyloxyimino-1-methyl-2-[4-(3-trifluoromethyl-benzyloxy)-phenyl]-ethylideneaminooxymethyl}-phenyl)-3methoxy-acrylic acid methyl ester (compound 4.4);

(51) (2-{2-Ethoxyimino-1-methyl-2-[4-(3-trifluoromethyl-benzyloxy)-phenyl]-ethylideneaminooxymethyl}-phenyl)-3-methoxy-acrylic acid methyl ester (compound 4.5);

(52) 3-Methoxy-2-(2-{1-methyl-2-prop-2-ynyloxyimino-2-[4-(3-trifluoromethyl-benzyloxy)-phenyl]-ethylideneaminooxymethyl}phenyl)-acrylic acid methyl ester (compound 4.6);

(53) (2-{2-[4-(2,2-Dichloro-cyclopropylmethoxy)-2-fluoro-phenyl]-2-methoxyimino-1-methyl-ethylideneaminooxymethyl}-phenyl)-3-methoxy-acrylic acid methyl ester (compound 1.9);

(54) {2-[4-(4-Bromo-phenoxy)-phenyl]-2-methoxyimino-1-methyl-ethylideneaminooxymethyl}-phenyl)-methoxyimino-acetic acid methyl ester (compound 2.28);

(55) (2-{2-[4-(3-Chloro-phenoxy)-phenyl]-2-methoxyimino-1-methyl-ethylideneaminooxymethyl}-phenyl)-3-methoxy-acrylic acid methyl ester (compound 1.36);

(56) (2-{2-[4-(4-.tert.-Butyl-benzyloxy)-phenyl]-2-methoxyimino-1-methyl-ethylideneaminooxymethyl}-phenyl)-3-methoxy-acrylic acid methyl ester (compound 1.28);

(57) (2-{2-[4-(4-Fluoro-benzyloxy)-phenyl]-1-methyl-2-prop-2-ynyloxyimino-ethylideneaminooxymethyl}-phenyl)-3-methoxy-acrylic acid methyl ester (compound 4.21);

(58) (2-{2-Ethoxyimino-2-[4-(4-fluoro-benzyloxy)-phenyl]-1-methyl-ethylideneaminooxymethyl }-phenyl)-3-methoxy-acrylic acid methyl ester (compound 4.24);

(59) Methoxyimino-(2-{1-methyl-2-prop-2-ynyloxyimino-2-[4-(3-trifluoromethyl -benzyloxy)-phenyl]-ethylideneaminooxymethyl}-phenyl)-acetic acid methyl ester (compound 4.18);

(60) (2-{2-Butoxyimino-1-methyl-2-[4-(3-trifluoromethyl-benzyloxy)-phenyl]-ethylideneaminooxymethyl}phenyl)-3-methoxy-acrylic acid methyl ester (compound 4.15);

(61) (2-{2-[4-(4-Chloro-phenoxy)-phenyl]-2-ethoxyimino-1-methyl-ethylideneaminooxymethyl }-phenyl)-3-methoxy-acrylic acid methyl ester (compound 4.20);

(62) {2-[2-(4-Isobutoxy-phenyl)-2-methoxyimino-1-methyl-ethylideneaminooxymethyl]-phenyl}-3-methoxy-acrylic acid methyl ester (compound 1.31);

(63) {2-[2-(2-Fluoro4-propoxy-phenyl)-2-methoxyimino-1-methyl-ethylideneaminooxymethyl]-phenyl}-3-methoxy-acrylic acid methyl ester (compound 1.63);

(64) (2-{2-Ethoxyimino-1-methyl-2-[4-(4-trifluoromethyl-benzyloxy)-phenyl]-ethylideneaminooxymethyl}-phenyl)-3-methoxy-acrylic acid methyl ester (compound 4.25);

(65) {2-Ethoxyimino-1-methyl-2-[4-(4-trifluoromethyl-benzyloxy)-phenyl]-ethylideneaminooxymethyl}-phenyl)-methoxyimino-acetic acid methyl ester (compound 4.26);

(66) (2-{2-Ethoxyimino-1-methyl-2-[4-(4-trifluoromethyl-benzyloxy)-phenyl]-ethylideneaminooxymethyl}-phenyl)-2-methoxyimino-N-methyl-acetamide (compound 4.27);

(67) {2-Ethoxyimino-1-methyl-2-[4-(2-trifluoromethyl-benzyloxy)-phenyl]-ethylideneaminooxymethyl}-phenyl)-methoxyimino-acetic acid methyl ester (compound 4.28);

(68) (2-{2-Ethoxyimino-1-methyl-2-[4-(2-trifluoromethyl-benzyloxy)-phenyl]-ethylideneaminooxymethyl}-phenyl)-2-methoxyimino-N-methyl-acetamide (compound 4.29);

(69) (2-{2-Ethoxyimino-1-methyl-2-[4-(3-trifluoromethyl-phenoxy)-phenyl]-ethylideneaminooxymethyl}-phenyl)-3-methoxy-acrylic acid methyl ester (compound 4.32);

(70) {2-[4-(4-Chloro-phenoxy)-phenyl]-2-ethoxyimino-1-methyl-ethylideneaminooxymethyl}-phenyl)-methoxyimino-acetic acid methyl ester (compound 4.68);

(71) (2-{2-[4-(4-Chloro-phenoxy)-phenyl]-2-ethoxyimino-1-methyl-ethylideneaminooxymethyl}-phenyl)-2-methoxyimino-N-methyl-acetamide (compound 4.70);

(72) {2-[4-(3,4-Dichloro phenoxy)-phenyl]-2-ethoxyimino-1-methyl-ethylideneaminooxymethyl}-phenyl)-methoxyimino-acetic acid methyl ester (compound 4.71);

(73) (2-{2-[4-(3,4-Dichloro-phenoxy)-phenyl]-2-ethoxyimino-1-methyl-ethylideneaminooxymethyl}-phenyl)-3-methoxy-acrylic acid methyl ester (compound 4.72);

(74) (2-{2-[4-(3,4-Dichloro-phenoxy)-phenyl]-2-ethoxyimino-1-methyl-ethylideneaminooxymethyl}- phenyl)-2-methoxyimino-N-methyl-acetamide (compound 4.73);

(75) (2-{2-Ethoxyimino-1-methyl-2-[4-(4-trifluoromethyl-phenoxy)-phenyl]-ethylideneaminooxymethyl}-phenyl)-2-methoxyimino-N-methyl-acetamide (compound 4.146);

(76) (2-{2-Ethoxyimino-1-methyl-2-[4-(4-trifluoromethyl-phenoxy)-phenyl]-ethylideneaminooxymethyl}-phenyl)-2-methoxyimino-N-methyl-acetamide (compound 4.144);

(77) {2-Ethoxyimino-1-methyl-2-[4-(4-trifluoromethyl-phenoxy)-phenyl]-ethylideneaminooxymethyl}-phenyl)-methoxyimino-acetic acid methyl ester (compound 4.141);

(78) (2-{2-[4-(4-Chloro-benzyloxy)-phenyl]-2-ethoxyimino-1-methyl-ethylideneaminooxymethyl}-phenyl)-3-methoxy-acrylic acid methyl ester (compound 4.66);

(79) (2-{2-[4-(4-Bromo-phenoxy)-phenyl]-2-ethoxyimino-1-methyl-ethylideneaminooxymethyl}-phenyl)-3-methoxy-acrylic acid methyl ester (compound 4.39);

(80) (2-{2-[4-(4-.tert.-Butyl-phenoxy)-phenyl]-2-ethoxyimino-1-methyl-ethylideneaminooxymethyl}-phenyl)-3-methoxy-acrylic acid methyl ester (compound 4.55);

(81) [4-isobutoxy-phenyl]-2-methoxyimino-1-methyl-ethylideneaminooxymethyl}-phenyl)-3-methoxy-acrylic acid methyl ester (compound 1.31);

(82) [4-fluoro-2-methyl-phenyl]-2-methoxyimino-1-methyl-ethylideneaminooxymethyl}-phenyl) -3-methoxy-acrylic acid methyl ester (compound 1.51);

(83) [2-fluoro-4-methyl-phenyl]-2-methoxyimino-1-methyl-ethylideneaminooxymethyl}-phenyl) -3-methoxy-acrylic acid methyl ester (compound 1.57);

(84) [4-cyclopentyloxy-phenyl]-2-methoxyimino-1-methyl-ethylideneaminooxymethyl}-phenyl) -3-methoxy-acrylic acid methyl ester (compound 1.62);

(85) [2-fluoro-4-n-propyloxy-phenyl]-2-methoxyimino-1-methyl-ethylideneaminooxymethyl}-phenyl) -3-methoxy-acrylic acid methyl ester (compound 1.63);

(86) [2-methyl-4-n-propoxy-phenyl]-2-methoxyimino-1-methyl-ethylidene-aminooxymethyl}-phenyl) -3-methoxy-acrylic acid methyl ester (compound 1.64);

(87) [2-fluoro-4-ethoxy-phenyl]-2-methoxyimino-1-methyl-ethylideneaminooxymethyl}-phenyl) -3-methoxy-acrylic acid methyl ester (compound 1.70);

(88) [2-fluoro-4-methoxy-phenyl]-2-methoxyimino-1-methyl-ethylideneaminooxymethyl}-phenyl) -3-methoxy-acrylic acid methyl ester (compound 1.72);

(89) [4-ethoxy-2-methyl-phenyl]-2-methoxyimino-1-methyl-ethylideneaminooxymethyl}-phenyl -3-methoxy-acrylic acid methyl ester (compound 1.79);

(90) 2-Methoxyimino-(2-{2-methoxyimino-1-methyl-2-[4-isobutoxy)-phenyl]-ethylideneaminooxymethyl}-phenyl)-acetic acid methyl ester (compound 2.22);

(91) 2-Methoxyimino-(2-{2-methoxyimino-1-methyl-2-[4-n-propoxy-phenyl]-ethylideneaminooxymethyl}-phenyl)-acetic acid methyl ester (compound 2.23);

(92) 2-Methoxyimino-(2-{2-methoxyimino-1-methyl-2-[4-fluoro-2-methyl-phenyl]-ethylideneaminooxymethyl}-phenyl)-acetic acid methyl ester (compound 2.35);

(93) 2-Methoxyimino-(2-{2-methoxyimino-1-methyl-2-[2-fluoro-4-methyl-phenyl]-ethylideneaminooxymethyl}-phenyl)-acetic acid methyl ester (compound 2.39);

(94) 2-Methoxyimino-(2-{2-methoxyimino-1-methyl-2-[4-cyclopentyloxy-phenyl]-ethylideneaminooxymethyl}-phenyl)-acetic acid methyl ester (compound 2.44);

(95) 2-Methoxyimino-(2-{2-methoxyimino-1-methyl-2-[2-fluoro-4-n-propoxy-phenyl]-ethylideneaminooxymethyl}-phenyl)-acetic acid methyl ester (compound 2.45);

(96) 2-Methoxyimino-(2-{2-methoxyimino-1-methyl-2-[2-methyl-4-n-propoxy-phenyl]-ethylideneaminooxymethyl}-phenyl)-acetic acid methyl ester (compound 2.46);

(97) 2-Methoxyimino-(2-{2-methoxyimino-1-methyl-2-[2-fluoro-4-ethoxy-phenyl]-ethylideneaminooxymethyl}-phenyl)-acetic acid methyl ester (compound 2.49);

(98) 2-Methoxyimino-(2-{2-methoxyimino-1-methyl-2-[2-fluoro 4-methoxy-phenyl]-ethylideneaminooxymethyl}-phenyl)-acetic acid methyl ester (compound 2.52);

(99) 2-Methoxyimino-(2-{2-methoxyimino-1-methyl-2-[4-n-ethoxy-2-methyl-phenyl]-ethylideneaminooxymethyl}-phenyl)-acetic acid methyl ester (compound 2.59);

(100) 2-Methoxyimino-2-(2-{2-methoxyimino-1-methyl-2-[4-isobutoxy-phenyl]-ethylideneaminooxymethyl}-phenyl)-N-methyl-acetamide (compound 3.22);

(101) 2-Methoxyimino-2-(2-{2-methoxyimino-1-methyl-2-[4-n-propoxy-phenyl]-ethylideneaminooxymethyl}-phenyl)-N-methyl-acetamide (compound 3.23);

(102) 2-Methoxyimino-2-(2-{2-methoxyimino-1-methyl-2-[4-n-butoxy-phenyl]-ethylideneaminooxymethyl}-phenyl)-N-methyl-acetamide (compound 3.24);

(103) 2-Methoxyimino-2-(2-{2-methoxyimino-1-methyl-2-[4-fluoro-2-methyl-phenyl]-ethylideneaminooxymethyl}phenyl)-N-methyl-acetamide (compound 3.35);

(104) 2-Methoxyimino-2-(2-{2-methoxyimino-1-methyl-2-[2-fluoro-4-methyl-phenyl]-ethylideneaminooxymethyl}phenyl)-N-methyl-acetamide (compound 3.39);

(105) 2-Methoxyimino-2-(2-{2-methoxyimino-1-methyl-2-[4-cyclopentyloxy-phenyl]-ethylideneaminooxymethyl}-phenyl)-N-methyl-acetamide (compound 3.45);

(106) 2-Methoxyimino-2-(2-{2-methoxyimino-1-methyl-2-[2-fluoro-4-n-propoxy -phenyl]-ethylideneaminooxymethyl}-phenyl)-N-methyl-acetamide (compound 3.46);

(107) 2-Methoxyimino-2-(2-{2-methoxyimino-1-methyl-2-[2-methyl-4-n-propoxy -phenyl]-ethylideneaminooxymethyl}phenyl)-N-methyl-acetamide (compound 3.47);

(108) 2-Methoxyimino-2-(2-{2-methoxyimino-1-methyl-2-[2-fluoro-4-ethoxy-phenyl ]-ethylideneaminooxymethyl}phenyl)-N-methyl-acetamide (compound 3.50);

(109) 2-Methoxyimino-2-(2-{2-methoxyimino-1-methyl-2-[2-fluoro-4-methoxy -phenyl]-ethylideneaminooxymethyl}-phenyl)-N-methyl-acetamide (compound 3.53); and (110) 2-Methoxyimino-2-(2-{2-methoxyimino-1-methyl-2-[4-ethoxy-2-methyl-phenyl ]-ethylideneaminooxymethyl}-phenyl)-N-methyl-acetamide (compound 3.60).

The compounds of the formula (I) listed in Tables 1 to 158 and, where appropriate, E/Z isomers and E/Z isomer mixtures thereof are particularly preferred in the context of the invention.

The invention furthermore relates to the process for the preparation of the compounds of the formula (I) and, where appropriate, their E/Z isomers, E/Z isomer mixtures and/or tautomers, in each case in the free form or in salt form, for example which comprises a1) either reacting a compound of the formula

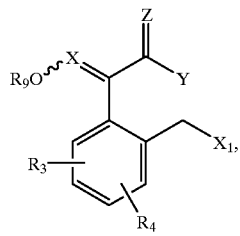

(II)

which is known or can be prepared by methods known per se and in which X, Y, Z, $R_3$, $R_4$ and $R_9$ are as defined for formula (I) and $X_1$ is a leaving group, and in which the provisos mentioned above for the compounds of the formula (I) apply, preferably in the presence of a base, with a compound of the formula

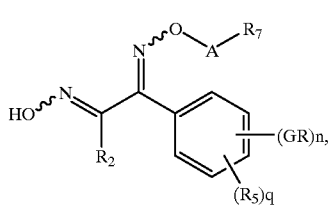

(IV)

in which n, q, A, G, R, $R_2$, $R_5$ and $R_7$ are as defined for formula (I), and in which the provisos mentioned above for the compounds of the formula (I) apply, or a2) reacting a compound of the formula

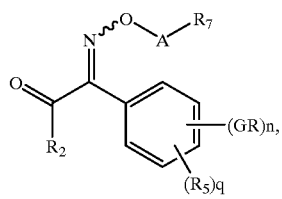

(IV)

in which n, q, R, A, G, $R_2$, $R_5$ and $R_7$ are as defined for formula (I), and in which the provisos mentioned above for the compounds of the formula (I) apply, if appropriate in the presence of a base, with a compound of the formula

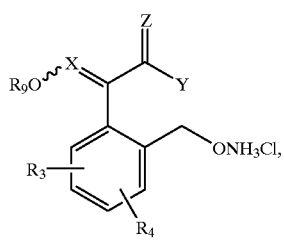

(V)

which is known or can be prepared by methods known per se, and in which X, Y, Z, $R^3$, $R_4$ and $R_9$ are as defined for formula (I), or b) for the preparation of a compound of the formula (I) in which Y is $NHR_8$ and Z is O, reacting a compound of the formula (I) in which Y is $OR_1$ with a compound of the formula $R_8NH_2$, which is known or can be prepared by methods known per se and in which $R_8$ is as defined for formula (I), or c) for the preparation of a compound of the formula (I) in which Y is $NHR_8$ and Z is S, reacting a compound of the formula (I) in which Y is $R_8NH$ and Z is O with $P_4S_{10}$ or Lawesson's reagent, or d) for the preparation of a compound of the formula (I) in which Z is SO, reacting a compound of the formula (I) in which Z is S with an oxidizing agent, or e) for the preparation of a compound of the formula (I) in which $R_5$ is aryl-Q—$C_2$-$C_6$alkyl, aryl-Q—$C_2$-$C_6$alkenyl, heterocyclyl-Q—$C_2$-$C_6$alkyl, heterocyclyl-Q—$C_2$-$C_6$alkenyl, or aryl-Q—$C_2$-$C_6$alkyl or aryl-Q—$C_2$-$C_6$alkenyl, heterocyclyl-Q—$C_2$-$C_6$alkyl or heterocyclyl-Q—$C_2$-$C_6$alkenyl which are mono- to pentasubstituted in the aryl or heterocyclyl ring, depending on the possibility of substitution, and where the substituents independently of one another are selected from the group consisting of halogen, $C_1$-$C_6$alkyl, halogeno-$C_1$-$C_6$alkyl, $C_3$-$C_6$cycloalkyl, halogeno-$C_3$-$C_6$cycloalkyl, $C_1$-$C_6$alkoxy, halogeno-$C_1$-$C_6$alkoxy, CN, nitro, OC(=O)—$C_1$-$C_6$alkyl, OH, $NH_2$ and $C_1$-$C_6$alkoxycarbonyl;

Q is a direct bond, —CH(OH)—; —C(=O)— or —S(=O)$_v$—; and v is 0, 1 or 2, reacting a compound of the formula

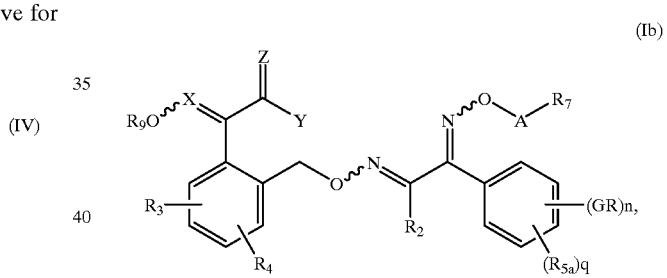

(Ib)

in which

X, Y, Z, $R_3$, $R_4$, $R_9$, n, q, R, A, G, $R_2$ and $R_7$ are as defined for formula (1), $R_{5a}$ is aryl-Q—$C_2$-$C_6$alkynyl or heterocyclyl-Q—$C_2$-$C_6$alkynyl, or aryl-Q—$C_2$—$C_6$alkynyl or heterocyclyl-Q—$C_2$-$C_6$alkynyl which are mono- to pentasubstituted in the aryl or heterocyclyl ring, depending on the possibility of substitution, and where the substituents independently of one another are chosen from the group consisting of halogen, $C_1$-$C_6$alkyl, halogeno-$C_1$-$C_6$alkyl, $C_3$-$C_6$cycloalkyl, halogeno-$C_3$-$C_6$-cycloalkyl, $C_1$-$C_6$alkoxy, halogeno-$C_1$-$C_6$alkoxy, CN, nitro and $C_1$-$C_6$alkoxycarbonyl;

Q is a direct bond, —CH(OH)—, —C(=O)— or —S(=O)$_v$—; and v is 0, 1 or 2;

and in which the provisos mentioned above for the compounds of the formula (I) apply;

which is known or can be prepared by processes known per se, with hydrogen in the presence of a hydrogenation catalyst, and in each case, if desired, converting a compound of the formula (I) obtainable according to the process or in another manner or an E/Z isomer or tautomer thereof, in each case in the free form or in salt form, into another compound of the formula (I) or an E/Z isomer or tautomer thereof, in each case in the free form or in salt form, separating a mixture of E/Z isomers obtainable according to the process and isolating the desired isomer, and/or converting a free compound of the formula (I) obtainable according to the process or in another manner or an E/Z isomer or tautomer thereof into a salt or converting a salt, obtainable according to the process or in another manner, of a compound of the formula (I) or of an E/Z isomer or tautomer thereof into the free compound of the formula (I) or an E/Z isomer or tautomer thereof or into another salt.

The invention furthermore relates to the process for the preparation of compounds of the formula (III), in each case in the free form or in salt form, for example which comprises f) reacting a compound of the formula (IV) in which n, q, A, G, R, $R_2$, $R_5$ and $R_7$ are as defined for formula (I) and in which the provisos mentioned above for the compounds of the formula (I) apply, if appropriate in the presence of a base, with $H_2NOH$ or a salt thereof, or g) reacting a compound of the formula

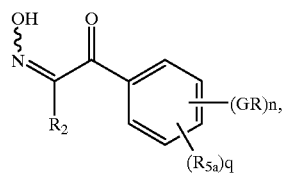

(VI)

in which n, q, G, R, $R_2$ and $R_5$ are as defined for formula (I) and in which the provisos mentioned above for the compounds of the formula (I) apply, if appropriate in the presence of a base, with a compound of the formula $R_7ANH_2$ (VII), which is known or can be prepared by methods known per se and in which A and $R_7$ are as defined for formula (1), and in each case, if desired, converting a compound of the formula (III) obtainable according to the process or in another manner or an E/Z isomer or tautomer thereof, in each case in the free form or in salt form, into another compound of the formula (III) or an E/Z isomer or tautomer thereof, in each case in the free form or in salt form, separating a mixture of E/Z isomers obtainable according to the process and isolating the desired isomers, and/or converting a free compound of the formula (III) obtainable according to the process or in another manner or an E/Z isomer or tautomer thereof into a salt, or converting a salt, obtainable according to the process or in another manner, of a compound of the formula (III) or of an E/Z isomer or tautomer thereof into the free compound of the formula (III) or an E/Z isomer or tautomer thereof or into another salt.

Because of their structure, the compounds of the formulae (III), (IV) and (VI) are particularly suitable for the preparation of the active end products of the formula (I) or other active substances having this part structure. Where they are new, the present invention likewise relates to them.

The statements above for the E/Z isomers and tautomers of compounds of the formulae (I) and (III) apply in an analogous manner to starting materials defined above and below in respect of E/Z isomers and tautomers thereof.

The reactions described above and below are carried out in a manner known per se, for example in the absence or usually in the presence of a suitable solvent or diluent or of a mixture thereof, the reactions being carried out, as required, with cooling, at room temperature or with heating, for example in a temperature range from about 0° C. up to the boiling point of the reaction medium, preferably from about 20° C. to about +120° C., in particular 60° C. to 80° C., and, if necessary, in a closed vessel, under pressure, in an inert gas atmosphere and/or under anhydrous conditions. Particularly advantageous reaction conditions can be seen from the examples.

The starting materials defined above and below which are used for the preparation of the compounds of the formula (I) and, where appropriate, their E/Z isomers and tautomers are known or can be prepared by methods known per se, for example according to the instructions below.

Variants a1/a2)

Suitable leaving groups $X_1$ in the compounds of the formula (II) are, for example, hydroxyl, $C_1$–$C_8$alkoxy, halogeno-$C_1$–$C_8$-alkoxy, $C_1$–$C_8$alkanoyloxy, mercapto, $C_1$–$C_8$alkylthio, halogeno-$C_1$–$C_8$-alkylthio, $C_1$–$C_8$-alkanesulfonyloxy, halogeno-$C_1$–$C_8$alkanesulfonyloxy, benzenesulfonyloxy, toluenesulfonyloxy and halogen, preferably toluenesulfonyloxy, trifluoromethanesulfonyloxy and halogen, in particular halogen.

Suitable bases to facilitate the reaction are, for example, alkali metal or alkaline earth metal hydroxides, hydrides, amides, alkanolates, acetates, carbonates, dialkylamides or alkylsilylamides, alkylamines, alkylenediamines, non-alkylated or N-alkylated, saturated or unsaturated cycloalkylamines, basic heterocyclic compounds, ammoniumhydroxides and carboxylic amines. Examples are sodium hydroxide, hydride, amide, methanolate, acetate, and carbonate, potassium tert-butanolate, hydroxide, carbonate and hydride, lithium diisopropylamide, potassium bis(trimethylsilyl)-amide, calcium hydride, triethylamine, diisopropylethyl-amine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU).

The reaction partners can be reacted with one another as such, i.e. without addition of a solvent or diluent, for example in the melt. Usually, however, the addition of an inert solvent or diluent or of a mixture thereof is advantageous. Examples of such solvents or diluents are: aromatic, aliphatic and alicyclic hydrocarbons and halogenated hydrocarbons, such as benzene, toluene, xylene, mesitylene, tetralin, chlorobenzene, dichlorobenzene, bromo-benzene, petroleum ether, hexane, cyclohexane, methylene chloride, chloroform, carbon tetrachloride, dichloroethane, trichloroethene or tetrachloroethene; esters, such as ethyl acetate, ethers, such as diethyl ether, dipropyl ether, diisopropyl ether, dibutyl ether, tert-butylmethyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methyl-pyrrolidone or hexamethylphosphoric acid triamide; nitriles, such as acetonitrile or propionitrile; and sulfoxides, such as dimethyl sulfoxide. If the reaction is carried out in the presence of a base, bases employed in excess, such as triethylamine, pyridine, N-methylmorpholine or N,N-diethylaniline, can also serve as solvents or diluents.

The reaction is advantageously carried out in a temperature range from about 0° C. to about 180° C., preferably from about 10° C. to about 80° C., in many cases in the range between room temperature and the reflux temperature of the reaction mixture.

The reaction is preferably carried out under normal pressure.

The reaction can be carded out without an inert gas atmosphere; however, it is preferably carried out under an inert gas atmosphere, for example nitrogen or argon, in particular nitrogen.

The reaction time is not critical; a reaction time of about 0.1 to about 24 hours, in particular about 0.5 to about 2 hours, is preferred.

The product is isolated by customary methods, for example by filtration, crystallization, distillation or chromatography or any suitable combination of these processes.

In a preferred embodiment of variants a1/a2), a compound (II) is reacted with a compound (III) at 0° C. to 80° C., preferably 10° C. to 30° C., in an inert solvent, preferably an amide, in particular N,N-dimethylformamide, in the presence of a metal hydride, preferably sodium hydride.

Particularly preferred conditions for the reaction are described in Examples H1d) and H1e).

The compounds of the formula (II) are known or can be prepared analogously to known compounds.

Variant b)

The reaction partners can be reacted with one another as such, i.e. without addition of a solvent or diluent, for example in the melt. Usually, however, the addition of an inert solvent or diluent or of a mixture thereof is advantageous. Examples of such solvents or diluents are those mentioned in variant a1/a2).

The reaction is advantageously carried out in a temperature range from about 0° C. to about 180° C., preferably from about 10° C. to about 80° C., in many cases in the range between room temperature and the reflux temperature of the reaction mixture.

The reaction is preferably carried out under normal pressure.

The reaction can be carried out without an inert gas atmosphere; preferably, however, it is carried out under an inert gas atmosphere, for example nitrogen or argon, in particular nitrogen.

The reaction time is not critical; a reaction time of about 0.1 to about 24 hours, in particular about 0.5 to about 2 hours, is preferred.

The product is isolated by customary methods, for example by filtration, crystallization, distillation or chromatography or any suitable combination of these processes.

Variant c)

The reaction partners can be reacted with one another as such, i.e. without addition of a solvent or diluent, for example in the melt. Usually, however, the addition of an inert solvent or diluent or of a mixture thereof is advantageous. Examples of such solvents or diluents are: aromatic, aliphatic and alicyclic hydrocarbons and halogenated hydrocarbons, such as benzene, toluene, xylene, mesitylene, tetralin, chlorobenzene, dichlorobenzene, bromo-benzene, petroleum ether, hexane, cyclohexane, methylene chloride, chloroform, carbon tetrachloride, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; and sulfoxides, such as dimethyl sulfoxide.

The reaction is advantageously carried out in a temperature range from about 0° C. to about +120° C., preferably from about 80° C. to about +120° C.

The reaction is preferably carried out under normal pressure.

The reaction can be carried out without an inert gas atmosphere; however, it is preferably carried out under an inert gas atmosphere, for example nitrogen or argon, in particular nitrogen.

The reaction time is not critical; a reaction time of about 0.1 to about 24 hours, in particular about 0.5 to about 2 hours, is preferred.

The product is isolated by customary methods, for example by filtration, crystallization, distillation or chromatography or any suitable combination of these processes.

Variant d)

Suitable oxidizing agents are, for example, inorganic peroxides, such as sodium perborate, or hydrogen peroxide, or organic peracids, such as perbenzoic acid or peracetic acid, or mixtures of organic acids and hydrogen peroxide, for example acetic acid/hydrogen peroxide.

The reaction partners can be reacted with one another as such, i.e. without addition of a solvent or diluent, for example in the melt. Usually, however, the addition of an inert solvent or diluent or of a mixture thereof is advantageous. Examples of such solvents or diluents are: aromatic, aliphatic and alicyclic hydrocarbons and halogenated hydrocarbons, such as benzene, toluene, xylene, mesitylene, tetralin, chlorobenzene, dichlorobenzene, bromo-benzene, petroleum ether, hexane, cyclohexane, methylene chloride, chloroform, carbon tetrachloride, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxy diethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethyl-formamide, N,N-dimethylacetamide, N-methylpyrrolidone or hexamethylphosphoric acid triamide; nitrites, such as acetonitrile or propionitrile; and sulfoxides, such as dimethyl sulfoxide. If the reaction is carried out in the presence of an organic acid or peracid, acids employed in excess, for example strong organic carboxylic acids, such as $C_1$–$C_4$alkanecarboxylic acids which are unsubstituted or substituted, for example by halogen, for example formic acid, acetic acid or propionic acid, can also serve as the solvent or diluent.

The reaction is advantageously carried out in a temperature range from about 0° C. to about +120° C., preferably from about 0° C. to about +40° C.

The reaction is preferably carried out under normal pressure.

The reaction can be carried out without an inert gas atmosphere; however, it is preferably carried out under an inert gas atmosphere, for example nitrogen or argon, in particular nitrogen.

The reaction time is not critical; a reaction time of about 0.1 to about 24 hours, in particular about 0.5 to about 2 hours, is preferred.

The product is isolated by customary methods, for example by filtration, crystallization, distillation or chromatography or any suitable combination of these processes.

Variant e)

Suitable hydrogenation catalysts are, in particular, transition metal catalysts, in particular palladium, ruthenium, rhodium, nickel, zinc or platinum catalysts. Raney nickel, palladium-on-active charcoal and Lindlar catalyst (Pd—$CaCO_3$—PbO) are particularly suitable. However, the hydrogenation can also be carried out in a homogeneous solution, for example in the presence of $RhCl(Ph_3)_3$ (Wilkinson's catalyst).

The reaction partners can be reacted with one another as such, i.e. without addition of a solvent or diluent, for example in the melt. Usually, however, the addition of an inert solvent or diluent or of a mixture thereof is advantageous. Examples of such solvents or diluents are those mentioned in variant a1/a2). Ethers, such as tetrahydrofuran or dioxane, and esters, such as ethyl acetate, are particularly suitable.

The reaction is advantageously carried out in a temperature range from about 0° C. to about 80° C., preferably from about 10° C. to about 50° C., and in many cases at room temperature.

The reaction is preferably carried out under normal pressure or slightly increased pressure, preferably under normal pressure.

The reaction time is not critical; a reaction time of about 0.1 to about 24 hours, in particular about 0.5 to about 2 hours, is preferred.

The product is isolated by customary methods, for example by filtration, crystallization, distillation or chromatography or any suitable combination of these processes.

Particularly preferred conditions for the reaction are described in Examples H3a) to c).

Variant f)

Suitable bases for facilitating the reaction are, for example, those mentioned in variant a1/a2).

The reaction partners can be reacted with one another as such, i.e. without addition of a solvent or diluent, for example in the melt. Usually, however, the addition of an inert solvent or diluent or of a mixture thereof is advantageous. Examples of such solvents or diluents are those mentioned in variant a1/a2).

The reaction is advantageously carded out in a temperature range from about 0° C. to about 180° C., preferably from about 10° C. to about 80° C., and in many cases in the range between room temperature and the reflux temperature of the reaction mixture.

The reaction is preferably carried out under normal pressure.

The reaction can be carried out without an inert gas atmosphere; however, it is preferably carried out under an inert gas atmosphere, for example nitrogen or argon, in particular nitrogen.

The reaction time is not critical; a reaction time of about 0.1 to about 24 hours, in particular about 0.5 to about 2 hours, is preferred.

The product is isolated by customary methods, for example by filtration, crystallization, distillation or chromatography or any suitable combination of these processes.

Variant g)

Suitable bases for facilitating the reaction are, for example, those mentioned in variant a1/a2).

The reaction partners can be reacted with one another as such, i.e. without addition of a solvent or diluent, for example in the melt. Usually, however, the addition of an inert solvent or diluent or of a mixture thereof is advantageous. Examples of such solvents or diluents are those mentioned in variant a1/a2).

The reaction is advantageously carried out in a temperature range from about 0° C. to about 180° C., preferably from about 10° C. to about 80° C., in many cases in the range between room temperature and the reflux temperature of the reaction mixture.

The reaction is preferably carried out under normal pressure.

The reaction can be carried out without an inert gas atmosphere; however, it is preferably carried out under an inert gas atmosphere, for example nitrogen or argon, in particular nitrogen.

The reaction time is not critical; a reaction time of about 0.1 to about 24 hours, in particular about 0.5 to about 2 hours, is preferred.

The product is isolated by customary methods, for example by filtration, crystallization, distillation or chromatography or any suitable combination of these processes.

In a preferred embodiment of variant f), a compound (VI) is reacted with a compound (VII) at 0° C. to 120° C., preferably 60° C. to 120° C., in an inert solvent, preferably an amine, in particular pyridine.

The compounds of the formulae (I), (II), (III), (IV), (V) and (VI) can be present in the form of one of the possible isomers or as a mixture thereof, for example depending on the number and the absolute and relative configuration of the asymmetric carbon atoms, as pure isomers, such as antipodes and/or diastereomers, or as isomer mixtures, such as enantiomer mixtures, for example racemates, diastereomer mixtures or racemate mixtures; the invention relates both to the pure isomers and to all the possible isomer mixtures and is in each case to be understood accordingly above and below, although stereochemical details are not mentioned specifically in every case.

Because of the physico-chemical differences of the constituents, diastereomer mixtures and racemate mixtures of compounds of the formulae (I), (II), (III), (IV), (V) and (VI) obtainable according to the process—depending on the choice of starting substances and procedures—or in another manner can be separated into the pure diasteromers or racemates in a known manner, for example by fractional crystallization, distillation and/or chromatography.

Correspondingly obtainable enantiomer mixtures, such as racemates, can be separated into the optical antipodes by known methods, for example by recrystallization from an optically active solvent, by chromatography over chiral adsorbents, for example high pressure liquid chromatography (HPLC) on acetylcellulose, with the aid of suitable microorganisms, by cleavage with specific, immobilized enzymes, or via the formation of inclusion compounds, for example using chiral crown ethers, only one enantiomer being complexed.

As well as by separation of corresponding isomer mixtures, pure diastereomers or enantiomers can also be obtained according to the invention by generally known methods of diastereoselective or enantioselective synthesis, for example by carrying out the process according to the invention with educts with correspondingly suitable stereochemistry.

In each case the more biologically active isomer, for example enantiomer, or isomer mixture, for example enantiomer mixture, is advantageously isolated or synthesized, if the individual components have a different biological activity.

The compounds of the formulae (I), (II), (III), (IV), (V) and (VI) can also be obtained in the form of their hydrates and/or include other solvents, for example solvents which may be used for crystallization of compounds present in solid form.

The invention relates to all those embodiments of the process in which a compound obtainable at any stage of the process is used as a starting substance or intermediate product and all or some of the missing steps are carried out, or a starting substance is used in the form of a derivative or salt and/or its racemates or antipodes or, in particular, is formed under the reaction conditions.

In the process of the present invention, those starting substances and intermediates which lead to the compounds of the formula (I) defined above as particularly valuable or preferably used.

The invention particularly relates to the preparation processes described in Examples H1a) to e).

The invention likewise relates to starting substances and intermediate products used according to the invention for the preparation of compounds of the formula (I) and to their use and processes for their preparation, in particular the compounds of the formulae (III), (IV) and (VI), which are novel. In particular, the compounds of the formulae (III) and (VI) can be prepared analogously to Examples H1c) and H1b) respectively.

The compounds of the formula (I) according to the invention are already preventively and/or curatively valuable active compounds with a very favourable biocidal spectrum even at low rates of concentration in the field of pest control, and at the same time show favourable tolerance by warm-blooded animals, fish and plants. The active compounds according to the invention are active against all or individual stages of development of normally sensitive and also of resistant animal pests, such as insects and representatives of the order Acarina, and phytopathogenic fungi. The insecticidal, ovicidal and/or acaricidal action of the active compounds according to the invention can manifest itself here directly, i.e. in mortality of the pests, which occurs immediately or only after some time, for example during moulting, or of their eggs, or indirectly, for example in reduced ovi position and/or hatching rate, the good action corresponding to a mortality rate of at least 50 to 60%. The animal pests mentioned include, for example: from the order Lepidoptera, for example, Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca*, Cadra cautella, *Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta,* Operophtera spp., *Ostrinia nubilalis,* Pammene spp., Pandemis spp., *Panolis flammea, Pectinophora gossypiella, Phthorimaea operculella, Pieris rapae,* Pieris spp., *Plutella xylostella,* Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.; from the order Coleoptera, for example, Agriotes spp., Anthonomus spp., *Atomaria linearis, Chaetocnema tibialis,* Cosmopolites spp., Curculio spp., Dermestes spp., Diabrotica spp., Epilachna spp., Eremnus spp., *Leptinotarsa decemlineata,* Lissorhoptrus spp., Melolontha spp., Oryceaphilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.; from the order Orthoptera, for example, Blatta spp., Blattella spp., Gryliotalpa spp., *Leucophaea maderae,* Locusta spp., Periplaneta spp. and Schistocerca spp.; from the order Isoptera, for example, Reticulitermes spp.; from the order Psocoptera, for example, Liposcelis spp.; from the order Anoplura, for example, Haematopinus spp., Linognathus spp., Pediculus spp., Pemphigus spp. and Phylloxera spp.; from the order Mallophaga, for example, Damalinea spp. and Trichodectes spp.; from the order Thysanoptera, for example, Franklin-iella spp., Hercinothrips spp., Taeniothrips spp., Thrips palmi, Thrips tabaci and Scirtothrips aurantii; from the order Heteroptera, for example, Cimex spp., Distantiella theobroma, Dysdercus spp., Euchistus spp. Eurygaster spp. Leptocorisa spp., Nezara spp., Piesma spp., Rhodnius spp., Sahlbergella singularis, Scotinophara spp. and Triatoma spp.; from the order Homoptera, for example, *Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica,* Quadraspidiotus spp., Rhopalosiphum spp., Saissetia spp., Scaphoideus spp., Schizaphis spp., Sitobion spp., *Trialeurodes vaporariorum,* Trioza erytreae and Unaspis citri; from the order Hymenoptera, for example, Acromyrmex, Atta spp., Cephus spp., Diprion spp., Diprionidae, Gilpinia polytoma, Hoplocampa spp., Lasius spp., *Monomorium pharaonis,* Neodiprion spp., Solenopsis spp. and Vespa spp.; from the order Diptera, for example, Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami,* Phorbia spp., *Rhagoletis pomonella,* Sciara spp., Stomoxys spp., Tabanus spp., Tannia spp. and Tipula spp.; from the order Siphonaptera, for example, Ceratophyllus spp. and *Xenopsylla cheopis;* from the order Thysanura, for example, *Lepisma saccharina* and from the order Acarina, for example, *Acarus siro, Aceria sheldoni, Aculus schlechtendali,* Amblyomma spp., Argas spp., Boophilus spp., Brevipalpus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Omithodoros spp., Panonychus spp., *Phyliocoptruta oleivora, Polyphagotarsonemus latus,* Psoroptes spp., Rhiplocephalus spp., Rhizoglyphus spp., Sarcoptes spp., Tarsonemus spp. and Tetranychus spp.

The phytopathogenic fungi mentioned include, for example: from the class of Fungi imperfecti, for example, Botrytis spp., Pyricularia spp., Helminthosporium spp., Fusarium spp., Septoria spp., Cercospora spp. and Alternaria spp.; from the class of Basidiomycetes, for example, Rhizoctonia spp., Hemileia spp. and Puccinia spp.; from the class of Ascomycetes, for example, Venturia spp., Erysiphe spp., Podosphaera spp., Monilinia spp. and Uncinula spp.; and from the class of Oomycetes, for example, Phytophthora spp., Pythium spp. and Plasmopara spp.

Using the active compounds according to the invention, in particular, pests of the type mentioned which occur on plants, in particular on useful and ornamental plants in agriculture, in horticulture and in forestry, or on parts, such as fruit, blossom, foliage, stems, tubers or roots, of such plants can be controlled, i.e. checked or destroyed, in some cases parts of plants which grow on later also additionally being protected against these pests.

Target cultures are, in particular, cereals, such as wheat, barley, rye, oats, rice, maize or sorghum; beet, such as sugar-beet or fodder beet; fruit, for example pomaceous fruit, stone fruit and soft fruit, such as apples, pears, plums, peaches, almonds, cherries or berries, for example strawberries, raspberries or blackberries; pulses, such as beans, lentils, peas or soya; oil crops, such as oilseed rape, mustard, poppy, olive, sunflower, coconut, castor, cacao or groundnut; cucumber plants, such as pumpkins, cucumbers or melons; fibre plants, such as cotton, flax, hemp or jute; citrus fruits, such as oranges, lemons, grapefruit or mandarins; vegetables, such as spinach, lettuce, asparagus, cabbage varieties, carrots, onions, tomatoes, potatoes or capsicums; laurel plants, such as avocado, cinnamonium or camphor; and tobacco, nuts, coffee, aubergines, sugar-cane, tea, pepper, vines, hops, banana plants, natural rubber plants and ornamental plants.

The active compounds according to the invention are particularly suitable for controlling insects and representatives of the order Acarina, in particular phytopathogenic feeding insects, such as Anthonomus grandis, Diabrotica balteata, Heliothis virescens larvae, Plutella xylostella and Spodoptera littoralis larvae, and spider mites, such as Tetranychus spp., in cotton, fruit, maize, soya, rape and vegetable crops.

Other fields of use of the active compounds according to the invention are the protection of stores and warehouses and of material and in the hygiene sector, in particular the protection of pets and productive livestock against pests of the type mentioned.

The invention therefore also relates to pesticides such as, to be chosen according to the required aims and given circumstances, emulsifiable concentrates, suspension concentrates, directly sprayable or dilutable solutions, spreadable pastes, dilute emulsions, soluble powders, dispersible powders, wettable powders, dusts, granules or encapsulations in polymeric substances which comprise—at least—one of the active compounds according to the invention.

The active compound is employed in these compositions in the pure form, a solid active compound, for example, in a specific particle size, or, preferably, together with—at least—one of the auxiliaries customary in formulation technology, such as extenders, for example solvents or solid carriers, or such as surface-active compounds (surfactants). The compositions may also contain UV-stabilizers, such as a benzotriazole-, a benzophenone-, a oxalic acid anilide-, a cinnamic acid- or an s-triazine-derivative.

Solvents are, for example: non-hydrogenated or partly hydrogenated aromatic hydrocarbons, preferably fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and ethers and esters thereof, such as propylene glycol, dipropylene glycol ether, ethylene glycol or ethylene glycol monomethyl or -ethyl ether, ketones, such as cyclohexanone, isophorone or diacetone alcohol, strongly polar solvents, such as N-methylpyrrolid-2-one, dimethyl sulfoxide or N,N-dimethylformamide, water, non-epoxidized or epoxidized plant oils, such as non-epoxidized or epoxidized rapeseed, castor, coconut or soya oil, and silicone oils.

The solid carriers used, for example for dusts and dispersible powders, are as a rule natural rock powders, such as calcite, talc, kaolin, montmorillonite or attapulgite. Highly disperse silicic acids or highly disperse absorbent polymers can also be acided to improve the physical properties. Granular adsorptive granule carriers are porous types, such as pumice, crushed brick, sepiolite or bentonite, and non-sorbent carrier materials are calcite or sand. A large number of granular materials of inorganic or organic nature can furthermore be used, in particular dolomite or comminuted plant residues.

Surface-active compounds are, depending on the nature of the active compound to be formulated, nonionic, cationic and/or anionic surfactants or surfactant mixtures with good emulsifying, dispersing and wetting properties. The surfactants listed below are to be regarded only as examples; many other surfactants which are customary in formulation technology and are suitable according to the invention are described in the relevant literature.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Substances which are furthermore suitable are water-soluble polyethylene oxide adducts, containing 20 to 250 ethylene glycol ether and 10 to 100 propylene glycol ether groups, on propylene glycol, ethylene diaminopolypropylene glycol and alkyl polypropylene glycol having 1 to 10 carbon atoms in the alkyl chain. The compounds mentioned usually contain 1 to 5 ethylene glycol units per propylene glycol unit. Examples are nonylphenol-polyethoxyethanols, castor oil polyglycol ethers, polypropylene-polyethylene oxide adducts, tributylphenoxypolyethoxyethanol, polyethylene glycol and octylphenoxypolyethoxyethanol. Other substances are fatty acid esters of polyoxyethylene sorbitan, such as polyoxyethylene sorbitan trioleate.

The cationic surfactants are, in particular, quaternary ammonium salts which contain, as substituents, at least one alkyl radical having 8 to 22 C atoms and, as further substituents, lower, non-halogenated or halogenated alkyl, benzyl or lower hydroxyalkyl radicals. The salts are preferably in the form of halides, methyl-sulfates or ethyl-sulfates. Examples are stearyl-trimethyl-ammonium chloride and benzyl-di-(2-chloroethyl)-ethyl-ammonium bromide.

Suitable anionic surfactants can be both water-soluble soaps and water-soluble synthetic surface-active compounds. Suitable soaps are the alkali metal, alkaline earth metal and substituted or unsubstituted ammonium salts of higher fatty acids ($C_{10}$–$C_{22}$), such as the sodium or potassium salts of oleic or stearic acid, or of naturally occurring fatty acid mixtures, which can be obtained, for example, from coconut oil or tall oil; and furthermore also the fatty acid methyl-taurine salts. However, synthetic surfactants are more frequently used, in particular fatty sulfonates, fatty sulfates, sulfonated benzimidazole derivatives or alkylarylsulfonates. The fatty sulfonates and sulfates are as a rule in the form of alkali metal, alkaline earth metal or substituted or unsubstituted ammonium salts and in general have an alkyl radical of 8 to 22 C atoms, alkyl also including the alkyl moiety of acyl radicals; examples are the sodium or calcium salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having about 8 to 22 C atoms. Alkylarylsulfonates are, for example, the sodium, calcium or triethanolammonium salts of dodecyl-benzenesulfonic acid, of dibutylnaphthalenesulfonic acid or of a naphthalenesulfonic acid-formaldehyde condensation product. Corresponding phosphates, such as salts of the phosphoric acid ester of a p-nonylphenol-(4–14)-ethylene oxide adduct or phospholipids, can further also be used.

The compositions as a rule comprise 0.1 to 99%, in particular 0.1 to 95%, of active compound and 1 to 99.9%, in particular 5 to 99.9%, of—at least—one solid or liquid auxiliary, it being possible as a rule for 0 to 25%, in particular 0.1 to 20%, of the composition to be surfactants (% is in each case per cent by weight). While concentrated compositions are more preferred as commercial goods, the end user as a rule uses dilute compositions which comprise considerably lower concentrations of active compound. Preferred compositions are composed, in particular, as follows (%=per cent by weight):

| Emulsifiable concentrates: | |
| --- | --- |
| Active compound: | 1 to 90%, preferably 5 to 20% |
| Surfactant: | 1 to 30%, preferably 10 to 20% |
| Solvent: | 5 to 98%, preferably 70 to 85% |
| Dusts: | |
| Active compound: | 0.1 to 10%, preferably 0.1 to 1% |
| Solid carrier: | 99.9 to 90%, preferably 99.9 to 99% |
| Suspension concentrates: | |
| Active compound: | 5 to 75%, preferably 10 to 50% |
| Water: | 94 to 24%, preferably 88 to 30% |
| Surfactant: | 1 to 40%, preferably 2 to 30% |
| Wettable powders: | |
| Active compound: | 0.5 to 90%, preferably 1 to 80% |
| Surfactant: | 0.5 to 20%, preferably 1 to 15% |
| Solid carrier: | 5 to 99%, preferably 15 to 98% |
| Granules: | |
| Active compound: | 0.5 to 30%, preferably 3 to 15% |
| Solid carrier: | 99.5 to 70%, preferably 97 to 85% |

The action of the compositions according to the invention can be extended considerably and adapted to given circumstances by addition of other insecticidal, acaricidal and/or fungicidal active compounds. Active compound additions here are, for example, representatives of the following classes of active compounds: organic phosphorus compounds, nitrophenols and derivatives, formamidines, ureas, carbamates, pyrethroids, chlorinated hydrocarbons and Bacillus thuringiensis preparations. The compositions according to the invention can also comprise further solid or liquid auxiliaries, such as stabilizers, for example non-epoxidized or epoxidized vegetable oils (for example epoxidized coconut oil, rapeseed oil or soya oil), defoamers, for example silicone oil, preservatives, viscosity regulators, binders and/or tackifiers, as well as fertilizers or other active compounds for achieving special effects, for example bactericides, nematicides, molluscicides or selective herbicides.

The compositions according to the invention are prepared in a known manner, in the absence of auxiliaries, for example, by grinding and/or sieving a solid active compound or active compound mixture, for example to a particular particle size, and if at least one auxiliary is present, for example, by intimate mixing and/or grinding of the active compound or active compound mixture with the auxiliary or auxiliaries. The invention likewise relates to these processes for the preparation of the compositions according to the invention and the use of the compounds of the formula (I) for the preparation of these compositions.

The invention furthermore relates to the methods of application for the compositions, i.e. the methods for controlling pests of the type mentioned, such as, to be chosen according to the intended aims and given circumstances, spraying, atomizing, dusting, brushing, dressing, scattering or pouring, and to the use of the compositions for controlling pests of the type mentioned. Typical rates of concentration here are between 0.1 and 1000 ppm, preferably between 0.1 and 500 ppm, of active compound. The rates of application per hectare are in general 1 to 2000 g of active compound per hectare, in particular 10 to 1000 g/ha, preferably 20 to 600 g/ha.

A preferred method of application in the field of crop protection is application to the foliage of the plants (foliar application), where the application frequency and rate of application can be determined according to the danger of infestation by the particular pests. However, the active compound can also enter the plants via the root system (systemic action) by soaking the locus of the plants with a liquid composition or incorporating the active compound in solid form into the locus of the plants, for example into the soil, for example in the form of granules (soil application). In paddy rice crops, such granules can be metered into the flooded rice field.

The compositions according to the invention are also suitable for protection of plant propagation material, for example seed, such as fruit, tubers or grain, or plant seedlings, against fungal infections and animal pests. In this case, the propagation material can be treated with the composition before planting out, and seed, for example, can be dressed before sowing. The active compounds according to the invention can also be applied to seed grains (coating) either by soaking the grains in a liquid composition or coating them with a solid composition. The composition can also be applied to the site of planting out during planting out of the propagation material, for example into the seed furrow during sowing. The invention furthermore relates to these treatment methods for plant propagation material and the plant propagation material thus treated.

The following examples serve to illustrate the invention. They do not limit the invention. Temperatures are stated in degrees Celsius.

Preparation Examples

Example H1

Methyl 2-[[[(1-methyl-2-(4-(3-trifluoromethylphenylmethoxy)-phenyl)-2-E-[ethoxyimino]ethylidene)amino]oxy]methyl]-α-(methoxymethylene)-phenylacetate and methyl 2-[[[(1-methyl-2-(4-(3-trifluoromethylphenylmethoxy)-phenyl)-2-Z-[ethoxyimino]ethylidene)amino]oxy]methyl]-α-(methoxymethylene)-phenylacetate (compounds A.1 in Table 7)

a) 1-[4-(3-Trifluromethylphenylmethoxy)-phenyl]-1-propanone 172 g of 1-(chloromethyl)-3-(trifluoromethyl)-benzene are slowly added to a mixture of 120 g of 1-(4-hydroxyphenyl)-1-propanone, 2.21 g of potassium carbonate and 500 ml of N,N-dimethylformamide at room temperature. Thereafter, the reaction mixture is stirred at 60° for 1 hour and then cooled and filtered, and the filtrate is evaporated in vacuo. The residue is dissolved in ethyl acetate and the organic phase is washed twice with water and once with saturated sodium chloride solution, dried with sodium sulfate and evaporated. The crude product is stirred up with 500 ml of hexane and cooled, filtered off and dried in vacuo. Pure 1-[4-(3-trifluoromethylphenylmethoxy)-phenyl]-1-propanone with a melting point of 63–4° is thus obtained.

b) 1-[4-(3-trifluoromethylphenylmethoxy)-phenyl]-1,2-propanedione 2-oxime 107 g of isopentyl nitrite are slowly added dropwise to a solution of 234.3 g of 1-[4-(3-trifluoromethylphenylmethoxy)-phenyl]-1-propanone in 1500 ml of 1,4-dioxane acidified with hydrochloric acid gas. The reaction mixture is then stirred at room temperature for 1.5 hours, subsequently rendered alkaline with triethylamine and evaporated in vacuo. The residue is dissolved in ethyl acetate and the organic phase is washed twice with water and once with saturated sodium chloride solution, dried with sodium sulfate and evaporated. The crude product is suspended in hexane, filtered off and dried in vacuo. 1-[4-(3-trifluoromethylphenylmethoxy)-phenyl]-1,2-propanedione 2-oxime with a melting point of 137–8° is thus obtained.

c) 1-[4-(3-trifluoromethylphenylmethoxy)-phenyl]-1,2-propanedione 1-E-[ethyloxime]-2-oxime and 1-[4-(3-trifluoromethylphenylmethoxy)-phenyl]-1,2-propanedione 1-Z-[ethyloxime]-2-oxime A mixture of 67.4 g of 1-[4-(3-trifluoromethylphenylmethoxy)-phenyl]-1,2-propanedione 2-oxime and 19.5 g of O-ethylhydroxylamine hydrochloride in 300 ml of pyridine is refluxed for 1.5 hours. After cooling, 1000 ml of toluene are added to the reaction mixture and the mixture is evaporated in vacuo. The residue is dissolved in ethyl acetate and the organic phase is washed twice with water and once with saturated sodium chloride solution, dried with sodium sulfate and evaporated. The crude product is purified by means of flash chromatography over silica gel (ethyl acetate/hexane 1:3), the two isomeric compounds 1-[4-(3-trifluoromethylphenylmethoxy)-phenyl]-1,2-propanedione 1-E-[ethyloxime]-2-oxime with a melting point of 125–7° and 1-[4-(3-trifluoromethylphenylmethoxy)-phenyl]-1,2propanedione 1-Z-[ethyloxime]-2-oxime, as a resin, being obtained.

d) Methyl 2-[[[(1-methyl-2-(4-(3-trifluoromethylphenylmethoxy)-phenyl)-2-E-[ethoxyimino] ethylidene)amino]oxy]methyl]-α-(methoxymethylene)-phenylacetate 4.5 g of 1-[4-(3-trifluoromethylphenylmethoxy)-phenyl]-1,2-propanedione 1-E-[ethyloxime]-2-oxime, dissolved in 15 ml of N,N-dimethylformamide, are added dropwise to a suspension of 0.65 g of sodium hydride in 25 ml of N,N-dimethylformamide and the reaction mixture is then stirred at room temperature for 10 minutes. Thereafter, 3.7 g of methyl 2-(bromomethyl)-α-(methoxymethylene)-phenylacetate in 15 ml of N,N-dimethylformamide are added dropwise and the reaction mixture is further stirred at room temperature for 1 hour. Thereafter, the mixture is acidified with acetic acid and evaporated in vacuo. The residue is dissolved in ethyl acetate and the solution is washed three times with water and once with saturated sodium chloride solution, dried with sodium sulfate and evaporated in vacuo. After purification by flash chromatography (silica gel, ethyl acetate/hexane 1:3), the E isomer of the title compound with a melting point of 81–83° C. is obtained.

e) Methyl 2-[[[(1-methyl-2-(4-(3-trifluoromethylphenylmethoxy)-phenyl)-2-Z-[ethoxyimino] ethylidene)-amino]oxy]methyl]-α-(methoxymethylene)-phenylacetate The Z isomer of the title compound is obtained as a viscous oil in a manner analogous to that described in Example H1 d), starting from 1-[4-(3-trifluoromethylphenylmethoxy)-phenyl]-1,2-propanedione 1-Z-[ethyloxime]-2-oxime.

f) Methyl 2-[[[(1-methyl-2-(4-(3-trifluoromethylphenylmethoxy)-phenyl)-2-E-[ethoxyimino] ethylidene)amino]oxy]methyl]-α-(methoxyimino)-phenylacetate The title compound with a melting point of 68–70° C. is obtained in a manner analogous to that described in Example H1 d) from 1-[4-(3-trifluoromethylphenylmethoxy)-phenyl]-1,2-propanedione 1-E-[ethyloxime]-2-oxime and methyl 2-(bromomethyl)-α-(methoxyimino)-phenylacetate.

g) 2-[[[(1-Methyl-2-(4-(3-trifluoromethylphenylmethoxy)-phenyl)-2-E-[ethoxyimino]ethylidene)amino]oxy]methyl]-α-(methoxyimino)-phenylacetic acid methylamide A mixture of 6.8 g of methyl 2-[[[(1-methyl-2-(4-(3-trifluoromethylphenylmethoxy)-phenyl)-2-E-[ethoxyimino] ethylidene)amino]oxy]methyl]-α-(methoxyimino)-phenylacetate and 4.3 ml of an 8 molar solution of methylamine in ethanol is left to stand at room temperature for 4 days. The mixture is then evaporated in vacuo. The residue is taken up in methyl acetate and the solution is washed with water and saturated sodium chloride solution, dried over sodium sulfate and evaporated in vacuo. The residue is recrystallized from methyl acetate/hexane 1:1. The title compound with a melting point of 130–132° C. is obtained.

Example H2

The other compounds listed in Tables 1 to 154 can also be prepared in a manner analogous to that described in Example H1. In the "Physical data" column of Tables 1 to 4, the temperatures stated in each case are the melting point of the compound in question. c.propyl is cyclopropyl.

TABLE 1

Compounds of the general formula $$\text{structure with } CH_3O, COOCH_3, N-OCH_3, R_2, (OR)_n, (R_5)_q$$

| Compd. | n | (OR)$_n$ | R$_2$ | (R$_5$)$_q$ | Isomer | Physical data |
|---|---|---|---|---|---|---|
| 1.1 | 1 | 4-OCH$_2$C$_6$H$_4$-3-CF$_3$ | CH$_3$ | 3-F | A | 112–4° |
| 1.2 | 1 | 4-OCH$_2$C$_6$H$_4$-3-CF$_3$ | CH$_3$ | 3-F | B | Resin |
| 1.3 | 1 | 4-OCH$_2$-c-C$_3$H$_3$-2,2-Cl$_2$ | CH$_3$ | 3-F | A | Resin |
| 1.4 | 1 | 4-OCH$_2$-c-C$_3$H$_3$-2,2-Cl$_2$ | CH$_3$ | 3-F | B | Resin |
| 1.5 | 1 | 4-OCH$_2$C$_6$H$_4$-4-F | CH$_3$ | 3-F | A | 88–90° |
| 1.6 | 1 | 4-OCH$_2$C$_6$H$_4$-2-F | CH$_3$ | 3-F | A | 103–105° |
| 1.7 | 1 | 4-OCH$_2$C$_6$H$_4$-3-CF$_3$ | CH$_3$ | 2-F | A | 100–103° |
| 1.8 | 1 | 4-OCH$_2$C$_6$H$_4$-4-F | CH$_3$ | 2-F | A | 89–95° |
| 1.9 | 1 | 4-OCH$_2$-c-C$_3$H$_3$-2,2-Cl$_2$ | CH$_3$ | 2-F | A | 73–74° |
| 1.10 | 1 | 4-OCH$_2$-c-C$_3$H$_3$-2,2-Cl$_2$ | CH$_3$ | 2-F | B | Resin |
| 1.11 | 1 | 4-OCH$_2$C$_6$H$_4$-3-CF$_3$ | CH$_3$ | 3,5-F$_2$ | A | 114–116° |
| 1.12 | 1 | 4-OCH$_2$-c-C$_3$H$_3$-2,2-Cl$_2$ | CH$_3$ | 3,5-F$_2$ | A | 79–81° |
| 1.13 | 1 | 4-OCH$_2$-c-C$_3$H$_3$-2,2-Cl$_2$ | CH$_3$ | 2,5-F$_2$ | A | Resin |
| 1.14 | 1 | 4-OCH$_2$C$_6$H$_4$-3-CF$_3$ | CH$_3$ | 2,5-F$_2$ | A | Resin |
| 1.15 | 1 | 4-OCH$_2$C$_6$H$_4$-4-F | CH$_3$ | 2,5-F$_2$ | A | 102–105° |
| 1.16 | 1 | 4-OCH$_2$C$_6$H$_4$-3-CF$_3$ | CH$_3$ | 3-Cl | A | 134–135° |
| 1.17 | 1 | 4-OCH$_2$C$_6$H$_4$-3-CF$_3$ | CH$_3$ | 3-Cl | B | Resin |
| 1.18 | 1 | 4-OCH$_2$C$_6$H$_4$-4-F | CH$_3$ | 3-Cl | A | 103–105° |
| 1.19 | 1 | 4-OCH$_2$-c-C$_3$H$_3$-2,2-Cl$_2$ | CH$_3$ | 3-Cl | A | Resin |
| 1.20 | 1 | 4-OCH$_2$-c-C$_3$H$_3$-2,2-Cl$_2$ | CH$_3$ | 3-Cl | B | Resin |
| 1.21 | 1 | 4-OCH$_2$C$_6$H$_4$-3-CF$_3$ | CH$_3$ | 3,5-Cl$_2$ | A | 99–100° |
| 1.22 | 1 | 4-OCH$_2$C$_6$H$_4$-3-CF$_3$ | CH$_3$ | 3,5-Cl$_2$ | B | Resin |
| 1.23 | 1 | 4-OCH$_2$C$_6$H$_4$-4-F | CH$_3$ | 3,5-Cl$_2$ | A | 112–114° |
| 1.24 | 1 | 4-OCH$_2$C$_6$H$_4$-4-F | CH$_3$ | 3,5-Cl$_2$ | B | Resin |
| 1.25 | 1 | 4-OCH$_2$C$_6$H$_4$-3-CF$_3$ | C$_2$H$_5$ | — | A | Resin |
| 1.26 | 1 | 4-OCH$_2$C$_6$H$_4$-3-CF$_3$ | C$_2$H$_5$ | — | B | Resin |
| 1.27 | 1 | 4-OCH$_2$C$_6$H$_4$-3-CF$_3$ | CN | — | A/B | Resin |
| 1.28 | 1 | 4-OCH$_2$C$_6$H$_4$-4-t-butyl | CH$_3$ | — | A | 53–55° |
| 1.29 | 1 | 4-OCH(CH$_3$)C$_2$H$_5$ | CH$_3$ | — | A | Oil |
| 1.30 | 1 | 4-OCH(CH$_3$)C$_2$H$_5$ | CH$_3$ | — | B | Oil |
| 1.31 | 1 | 4-OCH$_2$CH(CH$_3$)$_2$ | CH$_3$ | — | A | Oil |
| 1.32 | 1 | 4-OCH$_2$CH(CH$_3$)$_2$ | CH$_3$ | — | B | Oil |
| 1.33 | 1 | 4-O(CH$_2$)$_3$CH$_3$ | CH$_3$ | — | A/B | Oil |
| 1.34 | 1 | 4-OC$_6$H$_4$-3-Br | CH$_3$ | — | A | 129–131° |
| 1.35 | 1 | 4-OC$_6$H$_4$-3-Br | CH$_3$ | — | B | Oil |
| 1.36 | 1 | 4-OC$_6$H$_4$-3-Cl | CH$_3$ | — | A | 106–108° |
| 1.37 | 1 | 4-OC$_6$H$_4$-3-Cl | CH$_3$ | — | B | Oil |
| 1.38 | 1 | 4-OC$_6$H$_4$-4-CH$_3$ | CH$_3$ | — | A | 135–137° |
| 1.39 | 1 | 4-OC$_6$H$_4$-4-CH$_3$ | CH$_3$ | — | B | Oil |
| 1.40 | 1 | 4-OC$_6$H$_4$-4-Br | CH$_3$ | — | A | 124–126° |
| 1.41 | 1 | 4-OC$_6$H$_4$-4-Br | CH$_3$ | — | B | Resin |
| 1.42 | 1 | 4-OC$_6$H$_4$-2-F | CH$_3$ | — | A | 122–124° |
| 1.43 | 1 | 4-OC$_6$H$_4$-2-F | CH$_3$ | — | B | Resin |
| 1.44 | 1 | 4-OC$_6$H$_4$-3-F | CH$_3$ | — | A | 129–131° |
| 1.45 | 1 | 4-OC$_6$H$_4$-3-F | CH$_3$ | — | B | Oil |
| 1.46 | 1 | 3-OC$_6$H$_4$-3-CF$_3$ | CH$_3$ | — | A | Oil |
| 1.47 | 1 | 3-OC$_6$H$_4$-3-CF$_3$ | CH$_3$ | — | B | Oil |
| 1.48 | 1 | 4-OCH$_2$Si(CH$_3$)$_3$ | CH$_3$ | — | | |
| 1.49 | 0 | | CH$_3$ | 4-Si(CH$_3$)$_3$ | A | Oil |
| 1.50 | 0 | | CH$_3$ | 4-Si(CH$_3$)$_3$ | B | Oil |
| 1.51 | 0 | | CH$_3$ | 2-CH$_3$, 4-F | A | Oil |
| 1.52 | 0 | | CH$_3$ | 2-CH$_3$, 5-F | A | 130–132° |
| 1.53 | 0 | | CH$_3$ | 3-CF$_3$, 4-Cl | A | 140–142° |
| 1.54 | 0 | | CH$_3$ | 3-CF$_3$, 4-Cl | B | Oil |
| 1.55 | 0 | | CH$_3$ | 5-CH$_3$, 2-F | A | 165–167° |
| 1.56 | 0 | | CH$_3$ | 5-CH$_3$, 2-F | B | Resin |
| 1.57 | 0 | | CH$_3$ | 4-CH$_3$, 2-F | A | 111–113° |
| | | | | | B | 80–82° |
| 1.58 | 0 | | CH$_3$ | 4-c-C$_3$H$_5$ | A | Oil |
| 1.59 | 0 | | CH$_3$ | 4-c-C$_3$H$_5$ | B | Oil |
| 1.60 | 1 | 4-OC$_6$H$_4$-4-t-butyl | CH$_3$ | — | A | Oil |
| 1.61 | 1 | 4-OC$_6$H$_4$-4-t-butyl | CH$_3$ | — | B | Resin |
| 1.62 | 1 | 4-O-cyclopentyl | CH$_3$ | — | A | Oil |

TABLE 1-continued

Compounds of the general formula

| Compd. | n | (OR)$_n$ | R$_2$ | (R$_5$)$_q$ | Isomer | Physical data |
|---|---|---|---|---|---|---|
| | | | | | B | Oil |
| 1.63 | 1 | 4-O(CH$_2$)$_2$CH$_3$ | CH$_3$ | 2-F | A | Oil |
| | | | | | B | Resin |
| 1.64 | 1 | 4-O(CH$_2$)$_2$CH$_3$ | CH$_3$ | 2-CH$_3$ | A | Oil |
| 1.65 | 0 | | CH$_3$ | 2,4-F$_2$ | A | 121–123° |
| 1.66 | 1 | 4-OCH$_2$C$_6$H$_4$-4-F | C$_2$H$_5$ | — | A | 105–107 |
| 1.67 | 1 | 4-OCH$_2$C$_6$H$_3$-2,4-Cl$_2$ | CH$_3$ | — | A | 154–156 |
| 1.68 | 1 | 4-OC$_6$H$_3$-2,4-Cl$_2$ | CH$_3$ | — | A | 113–115° |
| 1.69 | 1 | 2-OCH$_3$ | CH$_3$ | 4-O—CH$_3$ | A/B | Oil |
| 1.70 | 1 | 4-OC$_2$H$_5$ | CH$_3$ | 2-F | A | Oil |
| 1.71 | 1 | 4-O-(CH$_2$)$_3$CH$_3$ | CH$_3$ | 2-F | A | Oil |
| | | | | | B | Oil |
| 1.72 | 1 | 4-OCH$_3$ | CH$_3$ | 2-F | A | Oil |
| | | | | | B | Resin |
| 1.73 | 1 | 4-OCH(CH$_3$)$_2$ | CH$_3$ | 2-F | A | Resin |
| | | | | | B | Resin |
| 1.74 | 1 | 2-OCH$_3$ | CH$_3$ | 4-F | A | Oil |
| | | | | | B | Resin |
| 1.75 | 1 | 4-OCH(CH$_3$)C$_2$H$_5$ | CH$_3$ | 2-F | A | Oil |
| | | | | | B | Oil |
| 1.76 | 1 | 2-OCH$_3$ | CH$_3$ | 4-CH$_3$ | A/B | Resin |
| 1.77 | 1 | 4-O-c.pentyl | CH$_3$ | 2-F | A | Resin |
| | | | | | B | Resin |
| 1.78 | 1 | 4-OCH$_3$ | CH$_3$ | 2-CH$_3$ | A | Oil |
| 1.79 | 1 | 4-OC$_2$H$_5$ | CH$_3$ | 2-CH$_3$ | A | Oil |
| | | | | | B | Oil |
| 1.80 | 1 | 4-OCH(CH$_3$)$_2$ | CH$_3$ | 2-CH$_3$ | A | Resin |
| 1.81 | 1 | 4-O-c.pentyl | CH$_3$ | 2-CH$_3$ | A | Resin |
| 1.82 | 1 | 4-O—CH$_2$-c-C$_3$H$_3$-2,2-Cl$_2$ | CH$_3$ | 2-CH$_3$ | A | Resin |
| 1.83 | 1 | 4-OCH$_2$C$_6$H$_4$-3-CF$_3$ | CH$_3$ | 2-CH$_3$ | | |
| 1.84 | 1 | 4-OC$_6$H$_4$-4-Cl | CH$_3$ | 2-CH$_3$ | | |
| 1.85 | 1 | 4-OC$_6$H$_4$-3-CF$_3$ | CH$_3$ | 2-CH$_3$ | | |
| 1.86 | 1 | 2-O(CH$_2$)$_2$CH$_3$ | CH$_3$ | — | A | Oil |
| | | | | | B | Oil |
| 1.87 | 1 | 3-OCH$_3$ | CH$_3$ | 4-OCH$_3$ | A/B | Resin |
| 1.88 | 1 | 4-OCH$_2$C$_6$H$_4$-4-Cl | CH$_3$ | — | A | 113–115 |
| 1.89 | 1 | 4-OC$_6$H$_3$-3,4-Cl$_2$ | CH$_3$ | — | A | 130–132 |
| 1.90 | 1 | 4-OCH$_2$C$_6$H$_3$-3,4-Cl$_2$ | CH$_3$ | — | A | 93–96 |
| 1.91 | 1 | 4-OCH$_2$C$_6$H$_3$-3-Cl,4-Br | CH$_3$ | — | A | 109–11 |
| 1.92 | 1 | 4-OC$_6$H$_4$-2-Cl | CH$_3$ | — | A | 128–130 |
| 1.93 | 1 | 4-OC$_6$H$_4$-4-SCH$_3$ | CH$_3$ | — | A | 109–111 |
| 1.94 | 1 | 4-OC$_6$H$_4$-2,4-F$_2$ | CH$_3$ | — | A | 110–112 |
| 1.95 | 1 | 4-OC$_6$H$_4$-4-OCF$_3$ | CH$_3$ | — | A | 108–110 |
| 1.96 | 1 | 4-OC$_6$H$_4$-4-OC$_6$H$_5$ | CH$_3$ | — | A | 108–110 |
| 1.97 | 1 | 4-OC$_6$H$_4$-4-OCH$_3$ | CH$_3$ | — | A | 122–125 |
| 1.98 | 1 | 4-OC$_6$H$_4$-4-F | C$_2$H$_5$ | — | A | 105–107 |
| 1.99 | 1 | 4-OCH$_2$C$_6$H$_4$-4-CF$_3$ | CH$_3$ | 2-C$_2$H$_5$ | A | Resin |
| 1.100 | 1 | 4-OC$_6$H$_4$-4-CF$_3$ | CH$_3$ | — | A | 114–116 |
| 1.101 | 1 | 4-O-(2-Naphtyl) | CH$_3$ | — | A | 114–117 |
| 1.102 | 1 | 4-OC$_6$H$_4$-4-CN | CH$_3$ | — | A | 142–144 |
| 1.103 | 0 | | CH$_3$ | 2-Cl, 4-F | | |
| 1.104 | 0 | | CH$_3$ | 2-F, 4-Cl | | |
| 1.105 | 0 | | CH$_3$ | 2-F, 4-CF$_3$ | | |
| 1.106 | 0 | | CH$_3$ | 2,5-F$_2$ | | 158–160 |
| 1.107 | 1 | 4-OCH$_2$C$_6$H$_4$-4-CF$_3$ | CH$_3$ | 2-CH$_3$ | | |

In the "Physical data" column, the values stated in the Tables above and below are in each case the melting point of the compound in question in ° C.

TABLE 2

Compounds of the general formula

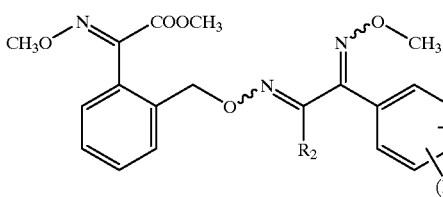

| Compound | n | (OR)$_n$ | R$_2$ | (R$_5$)$_q$ | Physical data |
|---|---|---|---|---|---|
| 2.1 | 1 | 4-OCH$_2$C$_6$H$_4$-3-CF$_3$ | CH$_3$ | 3-F | |
| 2.2 | 1 | 4-OCH$_2$-c-C$_3$H$_3$-2,2-Cl$_2$ | CH$_3$ | 3-F | |
| 2.3 | 1 | 4-OCH$_2$C$_6$H$_4$-4-F | CH$_3$ | 3-F | |
| 2.4 | 1 | 4-OCH$_2$C$_6$H$_4$-2-F | CH$_3$ | 3-F | |
| 2.5 | 1 | 4-OCH$_2$C$_6$H$_4$-3-CF$_3$ | CH$_3$ | 2-F | |
| 2.6 | 1 | 4-OCH$_2$C$_6$H$_4$-4-F | CH$_3$ | 2-F | |
| 2.7 | 1 | 4-OCH$_2$-c-C$_3$H$_3$-2,2-Cl$_2$ | CH$_3$ | 2-F | |
| 2.8 | 1 | 4-OCH$_2$C$_6$H$_4$-3-CF$_3$ | CH$_3$ | 3,5-F$_2$ | |
| 2.9 | 1 | 4-OCH$_2$-c-C$_3$H$_3$-2,2-Cl$_2$ | CH$_3$ | 3,5-F$_2$ | |
| 2.10 | 1 | 4-OCH$_2$-c-C$_3$H$_3$-2,2-Cl$_2$ | CH$_3$ | 2,5-F$_2$ | |
| 2.11 | 1 | 4-OCH$_2$C$_6$H$_4$-3-CF$_3$ | CH$_3$ | 2,5-F$_2$ | |
| 2.12 | 1 | 4-OCH$_2$C$_6$H$_4$-4-F | CH$_3$ | 2,5-F$_2$ | |
| 2.13 | 1 | 4-OCH$_2$C$_6$H$_4$-3-CF$_3$ | CH$_3$ | 3-Cl | |
| 2.14 | 1 | 4-OCH$_2$C$_6$H$_4$-4-F | CH$_3$ | 3-Cl | |
| 2.15 | 1 | 4-OCH$_2$-c-C$_3$H$_3$-2,2-Cl$_2$ | CH$_3$ | 3-Cl | |
| 2.16 | 1 | 4-OCH$_2$C$_6$H$_4$-3-CF$_3$ | CH$_3$ | 3,5-Cl$_2$ | |
| 2.17 | 1 | 4-OCH$_2$C$_6$H$_4$-4-F | CH$_3$ | 3,5-Cl$_2$ | |
| 2.18 | 1 | 4-OCH$_2$C$_6$H$_4$-3-CF$_3$ | C$_2$H$_5$ | — | |
| 2.19 | 1 | 4-OCH$_2$C$_6$H$_4$-3-CF$_3$ | CN | — | |
| 2.20 | 1 | 4-OCH$_2$C$_6$H$_4$-4-t-butyl | CH$_3$ | — | |
| 2.21 | 1 | 4-OCH(CH$_3$)C$_2$H$_5$ | CH$_3$ | — | 84–86° |
| 2.22 | 1 | 4-OCH(CH$_3$)$_2$ | CH$_3$ | — | Oil |
| 2.23 | 1 | 4-O(CH$_2$)$_2$CH$_3$ | CH$_3$ | — | Oil |
| 2.24 | 1 | 4-O(CH$_2$)$_3$CH$_3$ | CH$_3$ | — | Oil |
| 2.25 | 1 | 4-OC$_6$H$_4$-3-Br | CH$_3$ | — | 127–129° |
| 2.26 | 1 | 4-OC$_6$H$_4$-3-Cl | CH$_3$ | — | 118–120° |
| 2.27 | 1 | 4-OC$_6$H$_4$-4-CH$_3$ | CH$_3$ | — | 107–109° |
| 2.28 | 1 | 4-OC$_6$H$_4$-4-Br | CH$_3$ | — | 109–111 |
| 2.29 | 1 | 4-OC$_6$H$_4$-2-F | CH$_3$ | — | |
| 2.30 | 1 | 4-OC$_6$H$_4$-3-F | CH$_3$ | — | |
| 2.31 | 1 | 4-OC$_6$H$_4$-3-CF$_3$ | CH$_3$ | — | 106–108° |
| 2.32 | 1 | 3-OC$_6$H$_4$-3-F | CH$_3$ | — | |
| 2.33 | 1 | 4-OCH$_2$Si(CH$_3$)$_3$ | CH$_3$ | — | Oil |
| 2.34 | 0 | | CH$_3$ | 4-Si(CH$_3$)$_3$ | Oil |
| 2.35 | 0 | | CH$_3$ | 2-CH$_3$, 4-F | 116–119° |
| 2.36 | 0 | | CH$_3$ | 2-CH$_3$, 5-F | 112–114° |
| 2.37 | 0 | | CH$_3$ | 3-CF$_3$, 4-Cl | 97–99° |
| 2.38 | 0 | | CH$_3$ | 5-CH$_3$, 2-F | 158–160° |
| 2.39 | 0 | | CH$_3$ | 4-CH$_3$, 2-F | 116–118° |
| 2.40 | 0 | | CH$_3$ | 4-t-butyl | 120–122° |
| 2.41 | 0 | | CH$_3$ | 4-c-C$_3$H$_5$ | |
| 2.42 | 1 | 4-OCH$_2$CF$_3$ | CH$_3$ | — | 101–103° |
| 2.43 | 1 | 4-OC$_6$H$_4$-4-t-butyl | CH$_3$ | — | 129–131° |
| 2.44 | 1 | 4-O-cyclopentyl | CH$_3$ | — | Oil |
| 2.45 | 1 | 4-O(CH$_2$)$_2$CH$_3$ | CH$_3$ | 2-F | Oil |
| 2.46 | 1 | 4-O(CH$_2$)$_2$CH$_3$ | CH$_3$ | 2-CH$_3$ | |
| 2.47 | 1 | 4-OCH$_2$C$_6$H$_3$-2,4-Cl$_2$ | CH$_3$ | — | 149–151° |
| 2.48 | 1 | 4-OC$_6$H$_3$-2,4-Cl$_2$ | CH$_3$ | — | 112–114° |
| 2.49 | 1 | 4-OC$_2$H$_5$ | CH$_3$ | 2-F | 104–106° |
| 2.50 | 1 | 2-OCH$_3$ | CH$_3$ | 4-OCH$_3$ | Oil |
| 2.51 | 1 | 4-O-(CH$_2$)$_3$CH$_3$ | CH$_3$ | 2-F | Oil |
| 2.52 | 1 | 4-OCH$_3$ | CH$_3$ | 2-F | 99–101° |
| 2.53 | 1 | 4-OCH(CH$_3$)$_2$ | CH$_3$ | 2-F | Oil |
| 2.54 | 1 | 2-OCH$_3$ | CH$_3$ | 4-F | Resin |
| 2.55 | 1 | 4-OCH(CH$_3$)C$_2$H$_5$ | CH$_3$ | 2-F | Oil |
| 2.56 | 1 | 2-OCH$_3$ | CH$_3$ | 4-CH$_3$ | Resin |
| 2.57 | 1 | 4-O-c.pentyl | CH$_3$ | 2-F | Oil |
| 2.58 | 1 | 4-OCH$_3$ | CH$_3$ | 2-CH$_3$ | 127–130° |
| 2.59 | 1 | 4-OC$_2$H$_5$ | CH$_3$ | 2-CH$_3$ | 101–103 |
| 2.60 | 1 | 4-OCH(CH$_3$)$_2$ | CH$_3$ | 2-CH$_3$ | Resin |
| 2.61 | 1 | 4-O-c.pentyl | CH$_3$ | 2-CH$_3$ | Oil |
| 2.62 | 1 | 4-O—CH$_2$-c-C$_3$H$_3$-2,2-Cl$_2$ | CH$_3$ | 2-CH$_3$ | Resin |
| 2.63 | 1 | 4-OCH$_2$C$_6$H$_4$-3-CF$_3$ | CH$_3$ | 2-CH$_3$ | |
| 2.64 | 1 | 4-OC$_6$H$_4$-4-Cl | CH$_3$ | 2-CH$_3$ | |
| 2.65 | 1 | 4-OC$_6$H$_4$-3-CF$_3$ | CH$_3$ | 2-CH$_3$ | |
| 2.66 | 1 | 2-O(CH$_2$)$_2$CH$_3$ | CH$_3$ | — | Oil |
| 2.67 | 1 | 3-OCH$_3$ | CH$_3$ | 4-OCH$_3$ | Resin |
| 2.68 | 1 | 4-OCH$_2$C$_6$H$_4$-4-Cl | CH$_3$ | — | 108–109 |
| 2.69 | 1 | 4-OC$_6$H$_3$-3,4-Cl$_2$ | CH$_3$ | — | 104–106 |
| 2.70 | 1 | 4-OCH$_2$C$_6$H$_3$-3,4-Cl$_2$ | CH$_3$ | — | 104–106 |
| 2.71 | 1 | 4-OCH$_2$C$_6$H$_3$-3-Cl,4-Br | CH$_3$ | — | 114–116 |
| 2.72 | 1 | 4-OC$_6$H$_4$-2-Cl | CH$_3$ | — | 112–114 |
| 2.73 | 1 | 4-OC$_6$H$_4$-4-SCH$_3$ | CH$_3$ | — | 114–116 |
| 2.74 | 1 | 4-OC$_6$H$_4$-2,4-F$_2$ | CH$_3$ | — | 114–116 |
| 2.75 | 1 | 4-OC$_6$H$_4$-4-OCF$_3$ | CH$_3$ | — | 139–141 |
| 2.76 | 1 | 4-OC$_6$H$_4$-4-OC$_6$H$_5$ | CH$_3$ | — | 128–180 |
| 2.77 | 1 | 4-OC$_6$H$_4$-4-OCH$_3$ | CH$_3$ | — | 97–100 |
| 2.78 | 1 | 4-OCH$_2$C$_6$H$_4$-4-CF$_3$ | CH$_3$ | 2-C$_2$H$_5$ | 101–107 |
| 2.79 | 1 | 4-C$_6$H$_4$-4-CF$_3$ | CH$_3$ | — | 143–145 |
| 2.80 | 1 | 4-O-(2-Naphtyl) | CH$_3$ | — | 103–106 |
| 2.81 | 1 | 4-C$_6$H$_4$-4-CN | CH$_3$ | — | 158–160 |
| 2.82 | 0 | | CH$_3$ | 2,4-F$_2$ | 110–111 |
| 2.83 | 0 | | CH$_3$ | 2-Cl, 4-F | |
| 2.84 | 0 | | CH$_3$ | 2-F, 4-Cl | |
| 2.85 | 0 | | CH$_3$ | 2-F, 4-CF$_3$ | |
| 2.86 | 0 | | CH$_3$ | 2,5-F$_2$ | 139–142 |
| 2.87 | 1 | 4-OCH$_2$C$_6$H$_4$-4-CF$_3$ | CH$_3$ | 2-CH$_3$ | |

TABLE 3

Compounds of the general formula

| Compd. | n | (OR)$_n$ | R$_2$ | (R$_5$)$_q$ | Physical data |
|---|---|---|---|---|---|
| 3.1 | 1 | 4-OCH$_2$C$_6$H$_4$-3-CF$_3$ | CH$_3$ | 3-F | |
| 3.2 | 1 | 4-OCH$_2$-c-C$_3$H$_3$-2,2-Cl$_2$ | CH$_3$ | 3-F | |
| 3.3 | 1 | 4-OCH$_2$C$_6$H$_4$-4-F | CH$_3$ | 3-F | |
| 3.4 | 1 | 4-OCH$_2$C$_6$H$_4$-2-F | CH$_3$ | 3-F | |
| 3.5 | 1 | 4-OCH$_2$C$_6$H$_4$-3-CF$_3$ | CH$_3$ | 2-F | |
| 3.6 | 1 | 4-OCH$_2$C$_6$H$_4$-4-F | CH$_3$ | 2-F | |
| 3.7 | 1 | 4-OCH$_2$-c-C$_3$H$_3$-2,2-Cl$_2$ | CH$_3$ | 2-F | |
| 3.8 | 1 | 4-OCH$_2$C$_6$H$_4$-3-CF$_3$ | CH$_3$ | 3,5-F$_2$ | |
| 3.9 | 1 | 4-OCH$_2$-c-C$_3$H$_3$-2,2-Cl$_2$ | CH$_3$ | 3,5-F$_2$ | |
| 3.10 | 1 | 4-OCH$_2$-c-C$_3$H$_3$-2,2-Cl$_2$ | CH$_3$ | 2,5-F$_2$ | |
| 3.11 | 1 | 4-OCH$_2$C$_6$H$_4$-3-CF$_3$ | CH$_3$ | 2,5-F$_2$ | |
| 3.12 | 1 | 4-OCH$_2$C$_6$H$_4$-4-F | CH$_3$ | 2,5-F$_2$ | |
| 3.13 | 1 | 4-OCH$_2$C$_6$H$_4$-3-CF$_3$ | CH$_3$ | 3-Cl | |
| 3.14 | 1 | 4-OCH$_2$C$_6$H$_4$-4-F | CH$_3$ | 3-Cl | |
| 3.15 | 1 | 4-OCH$_2$-c-C$_3$H$_3$-2,2-Cl$_2$ | CH$_3$ | 3-Cl | |
| 3.16 | 1 | 4-OCH$_2$C$_6$H$_4$-3-CF$_3$ | CH$_3$ | 3,5-Cl$_2$ | |
| 3.17 | 1 | 4-OCH$_2$C$_6$H$_4$-4-F | CH$_3$ | 3,5-Cl$_2$ | |
| 3.18 | 1 | 4-OCH$_2$C$_6$H$_4$-3-CF$_3$ | C$_2$H$_5$ | — | |
| 3.19 | 1 | 4-OCH$_2$C$_6$H$_4$-3-CF$_3$ | CN | — | |
| 3.20 | 1 | 4-OCH$_2$C$_6$H$_4$-4-t-butyl | CH$_3$ | — | |
| 3.21 | 1 | 4-OCH(CH$_3$)C$_2$H$_5$ | CH$_3$ | — | 100–102° |
| 3.22 | 1 | 4-OCH$_2$CH(CH$_3$)$_2$ | CH$_3$ | — | 124–106° |
| 3.23 | 1 | 4-O(CH$_2$)$_2$CH$_3$ | CH$_3$ | — | Oil |
| 3.24 | 1 | 4-O(CH$_2$)$_3$CH$_3$ | CH$_3$ | — | Oil |
| 3.25 | 1 | 4-OC$_6$H$_4$-3-Br | CH$_3$ | — | 119–122° |
| 3.26 | 1 | 4-OC$_6$H$_4$-3-Cl | CH$_3$ | — | |
| 3.27 | 1 | 4-OC$_6$H$_4$-4-CH$_3$ | CH$_3$ | — | 119–121° |
| 3.28 | 1 | 4-OC$_6$H$_4$-4-Br | CH$_3$ | — | 138–140° |
| 3.29 | 1 | 4-OC$_6$H$_4$-2-F | CH$_3$ | — | |
| 3.30 | 1 | 4-OC$_6$H$_4$-3-F | CH$_3$ | — | |
| 3.31 | 1 | 4-OC$_6$H$_4$-3-CF$_3$ | CH$_3$ | — | 89–91° |
| 3.32 | 1 | 3-OC$_6$H$_4$-3-F | CH$_3$ | — | |
| 3.33 | 1 | 4-OCH$_2$Si(CH$_3$)$_3$ | CH$_3$ | — | |
| 3.34 | 0 | | CH$_3$ | 4-Si(CH$_3$)$_3$ | Oil |
| 3.35 | 0 | | CH$_3$ | 2-CH$_3$, 4-F | Oil |
| 3.36 | 0 | | CH$_3$ | 2-CH$_3$, 5-F | 139–140° |
| 3.37 | 0 | | CH$_3$ | 3-CF$_3$, 4-Cl | Foam |
| 3.38 | 0 | | CH$_3$ | 5-CH$_3$, 2-F | 125–128° |
| 3.39 | 0 | | CH$_3$ | 4-CH$_3$, 2-F | 130–134° |
| 3.40 | 0 | | CH$_3$ | 4-t-butyl | Foam |
| 3.41 | 0 | | CH$_3$ | 4-c-C$_3$H$_5$ | |
| 3.42 | 1 | 4-OC$_6$H$_4$-4-F | CH$_3$ | — | Oil |
| 3.43 | 1 | 4-OCH$_2$CF$_3$ | CH$_3$ | — | 159–161° |
| 3.44 | 1 | 4-OC$_6$H$_4$-4-t-butyl | CH$_3$ | — | Resin |
| 3.45 | 1 | 4-O-cyclopentyl | CH$_3$ | — | 133–135° |
| 3.46 | 1 | 4-O(CH$_2$)$_2$CH$_3$ | CH$_3$ | 2-F | Oil |
| 3.47 | 1 | 4-O(CH$_2$)$_2$CH$_3$ | CH$_3$ | 2-CH$_3$ | 99–101° |
| 3.48 | 1 | 4-OCH$_2$C$_6$H$_3$-2,4-Cl$_2$ | CH$_3$ | — | 87–88° |
| 3.49 | 1 | 4-OC$_6$H$_3$-2,4-Cl$_2$ | CH$_3$ | — | 118–120° |
| 3.50 | 1 | 4-OC$_2$H$_5$ | CH$_3$ | 2-F | 97–99° |
| 3.51 | 1 | 2-OCH$_3$ | CH$_3$ | 4-OCH$_3$ | Resin |
| 3.52 | 1 | 4-O-(CH$_2$)$_3$CH$_3$ | CH$_3$ | 2-F | Resin |
| 3.53 | 1 | 4-OCH$_3$ | CH$_3$ | 2-F | 132–134° |
| 3.54 | 1 | 4-OCH(CH$_3$)$_2$ | CH$_3$ | 2-F | Oil |
| 3.55 | 1 | 2-OCH$_3$ | CH$_3$ | 4-F | 186–189° |
| 3.56 | 1 | 4-OCH(CH$_3$)C$_2$H$_5$ | CH$_3$ | 2-F | Resin |
| 3.57 | 1 | 2-OCH$_3$ | CH$_3$ | 4-CH$_3$ | Resin |
| 3.58 | 1 | 4-O-c.pentyl | CH$_3$ | 2-F | 131–133° |
| 3.59 | 1 | 4-OCH$_3$ | CH$_3$ | 2-CH$_3$ | Oil |
| 3.60 | 1 | 4-OC$_2$H$_5$ | CH$_3$ | 2-CH$_3$ | Oil |
| 3.61 | 1 | 4-OCH(CH$_3$)$_2$ | CH$_3$ | 2-CH$_3$ | Oil |
| 3.62 | 1 | 4-O-c.pentyl | CH$_3$ | 2-CH$_3$ | 112–113 |
| 3.63 | 1 | 4-O—CH$_2$-c-C$_3$H$_3$-2,2-Cl$_2$ | CH$_3$ | 2-CH$_3$ | Resin |

TABLE 3-continued

Compounds of the general formula

| Compd. | n | (OR)$_n$ | R$_2$ | (R$_5$)$_q$ | Physical data |
|---|---|---|---|---|---|
| 3.64 | 1 | 4-OCH$_2$C$_6$H$_4$-3-CF$_3$ | CH$_3$ | 2-CH$_3$ | |
| 3.65 | 1 | 4-OC$_6$H$_4$-4-Cl | CH$_3$ | 2-CH$_3$ | |
| 3.66 | 1 | 4-OC$_6$H$_4$-3-CF$_3$ | CH$_3$ | 2-CH$_3$ | |
| 3.67 | 1 | 2-O(CH$_2$)$_2$CH$_3$ | CH$_3$ | — | Oil |
| 3.68 | 1 | 3-OCH$_3$ | CH$_3$ | 4-OCH$_3$ | Resin |
| 3.69 | 1 | 4-OCH$_2$C$_6$H$_4$-4-Cl | CH$_3$ | — | 121–124 |
| 3.70 | 1 | 4-OC$_6$H$_3$-3,4-Cl$_2$ | CH$_3$ | — | 135–137 |
| 3.71 | 1 | 4-OCH$_2$C$_6$H$_3$-3,4-Cl$_2$ | CH$_3$ | — | 146–148 |
| 3.72 | 1 | 4-OCH$_2$C$_6$H$_3$-2-Cl,4-Br | CH$_3$ | — | 128–130 |
| 3.73 | 1 | 4-OC$_6$H$_4$-2-Cl | CH$_3$ | — | 160–162 |
| 3.74 | 1 | 4-OC$_6$H$_4$-4-SCH$_3$ | CH$_3$ | — | 117–119 |
| 3.75 | 1 | 4-OC$_6$H$_4$-2-OCF$_3$ | CH$_3$ | — | 129–131 |
| 3.76 | 1 | 4-OC$_6$H$_4$-4-OC$_6$H$_5$ | CH$_3$ | — | 94–96 |
| 3.77 | 1 | 4-OC$_6$H$_4$-2,4-F$_2$ | CH$_3$ | — | 112–114 |
| 3.78 | 1 | 4-OC$_6$H$_4$-4-OCH$_3$ | CH$_3$ | — | 106–109 |
| 3.79 | 1 | 4-OCH$_2$C$_6$H$_4$-4-CF$_3$ | CH$_3$ | 2-C$_2$H$_5$ | 119–122 |
| 3.80 | 1 | 4-OC$_6$H$_4$-4-CF$_3$ | CH$_3$ | — | 128–131 |
| 3.81 | 1 | 4-O-(2-Naphtyl) | CH$_3$ | — | 155–157 |
| 3.82 | 1 | 4-OC$_6$H$_4$-4-CN | CH$_3$ | — | 126–128 |
| 3.83 | 0 | | CH$_3$ | 2,4-F$_2$ | 145 |
| 3.84 | 0 | | CH$_3$ | 2-Cl, 4-F | |
| 3.85 | 0 | | CH$_3$ | 2-F, 4-Cl | |
| 3.86 | 0 | | CH$_3$ | 2-F-, 4-CF$_3$ | |
| 3.87 | 0 | | CH$_3$ | 2,5-F$_2$ | 154–156 |
| 3.88 | 1 | 4-OCH$_2$C$_6$H$_4$-4-CF$_3$ | CH$_3$ | 2-CH$_3$ | |

TABLE 4

Compounds of the general formula

| Compd. | X | Y | R | AR$_7$ | Physical data |
|---|---|---|---|---|---|
| 4.1 | CH | OCH$_3$ | CH$_3$ | CH$_2$C$_6$H$_4$-3-CF$_3$ | Resin |
| 4.2 | CH | OCH$_3$ | CH$_3$ | CH$_2$C≡CH | Resin |
| 4.3 | CH | OCH$_3$ | CH$_3$ | CH$_2$CH=CCl$_2$ | Resin |
| 4.4 | CH | OCH$_3$ | CH$_2$C$_6$H$_4$-3-CF$_3$ | CH$_2$CH=CH$_2$ | 73–75° |
| 4.5 | CH | OCH$_3$ | CH$_2$C$_6$H$_4$-3-CF$_3$ | C$_2$H$_5$ | 81–83° |
| 4.6 | CH | OCH$_3$ | CH$_2$C$_6$H$_4$-3-CF$_3$ | CH$_2$C≡CH | Resin |
| 4.7 | CH | OCH$_3$ | CH$_2$C$_6$H$_4$-3-CF$_3$ | CH$_2$CH=CCl$_2$ | Resin |
| 4.8 | CH | OCH$_3$ | CH$_2$C$_6$H$_4$-3-CF$_3$ | CH$_2$Si(CH$_3$)$_3$ | Resin |
| 4.9 | CH | OCH$_3$ | CH$_2$C$_6$H$_4$-3-CF$_3$ | CH$_2$-c-C$_3$H$_3$-2,2-Cl$_2$ | Resin |
| 4.10 | CH | OCH$_3$ | CH$_2$C$_6$H$_4$-3-CF$_3$ | CH$_2$COOC$_2$H$_5$ | Resin |
| 4.11 | CH | OCH$_3$ | CH$_2$C$_6$H$_4$-3-CF$_3$ | CH(CH$_3$)COOC$_2$H$_5$ | Resin |
| 4.12 | CH | OCH$_3$ | CH$_2$C$_6$H$_4$-3-CF$_3$ | CH$_2$CF$_3$ | Resin |
| 4.13 | CH | OCH$_3$ | CH$_2$C$_6$H$_4$-3-CF$_3$ | n-C$_3$H$_7$ | Resin |
| 4.14 | CH | OCH$_3$ | CH$_2$C$_6$H$_4$-3-CF$_3$ | i-C$_3$H$_7$ | Resin |
| 4.15 | CH | OCH$_3$ | CH$_2$C$_6$H$_4$-3-CF$_3$ | n-C$_4$H$_9$ | Resin |
| 4.16 | N | OCH$_3$ | CH$_2$C$_6$H$_4$-3-CF$_3$ | C$_2$H$_5$ | 68–70° |
| 4.17 | N | NHCH$_3$ | CH$_2$C$_6$H$_4$-3-CF$_3$ | C$_2$H$_5$ | 130–132° |
| 4.18 | N | OCH$_3$ | CH$_2$C$_6$H$_4$-3-CF$_3$ | CH$_2$C≡H | Resin |

TABLE 4-continued

Compounds of the general formula

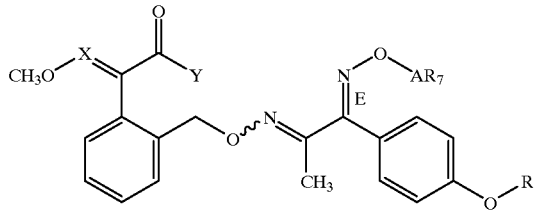

| Compd. | X | Y | R | AR$_7$ | Physical data |
|---|---|---|---|---|---|
| 4.19 | N | NHCH$_3$ | CH$_2$C$_6$H$_4$-3-CF$_3$ | CH$_2$C≡CH | 89–91° |
| 4.20 | CH | OCH$_3$ | C$_6$H$_4$-4-Cl | C$_2$H$_5$ | 87–89° |
| 4.21 | CH | OCH$_3$ | CH$_2$C$_6$H$_4$-4-F | CH$_2$C≡CH | 112–114° |
| 4.22 | CH | OCH$_3$ | CH$_2$C$_6$H$_4$-4-F | CH$_2$CH=CCl$_2$ | Resin |
| 4.23 | CH | OCH$_3$ | CH$_2$C$_6$H$_4$-4-F | CH$_2$C$_6$H$_4$-3-CF$_3$ | Resin |
| 4.24 | CH | OCH$_3$ | CH$_2$C$_6$H$_4$-4-F | C$_2$H$_5$ | Resin |
| 4.25 | CH | OCH$_3$ | CH$_2$C$_6$H$_4$-4-CF$_3$ | C$_2$H$_5$ | Resin |
| 4.26 | N | OCH$_3$ | CH$_2$C$_6$H$_4$-4-CF$_3$ | C$_2$H$_5$ | 75–77° |
| 4.27 | N | NHCH$_3$ | CH$_2$C$_6$H$_4$-4-CF$_3$ | C$_2$H$_5$ | 131–133° |
| 4.28 | N | OCH$_3$ | CH$_2$C$_6$H$_4$-2-CF$_3$ | C$_2$H$_5$ | 80–82° |
| 4.29 | N | NHCH$_3$ | CH$_2$C$_6$H$_4$-2-CF$_3$ | C$_2$H$_5$ | 112–114° |
| 4.30 | N | OCH$_3$ | —C$_6$H$_4$-3-CF$_3$ | C$_2$H$_5$ | 102–104° |
| 4.31 | N | NHCH$_3$ | —C$_6$H$_4$-3-CF$_3$ | C$_2$H$_5$ | 88–90° |
| 4.32 | CH | OCH$_3$ | —C$_6$H$_4$-3-CF$_3$ | C$_2$H$_5$ | 72–74° |
| 4.33 | CH | OCH$_3$ | CH$_2$C$_6$H$_4$-2-CF$_3$ | C$_2$H$_5$ | 93–95° |
| 4.34 | CH | OCH$_3$ | CH$_2$C$_6$H$_4$-2-F | C$_2$H$_5$ | 90–92 |
| 4.35 | CH | OCH$_3$ | CH$_2$C$_6$H$_4$-3-CF$_3$ | CH$_2$—CN | Resin |
| 4.36 | N | OCH$_3$ | CH$_2$C$_6$H$_4$-2-F | C$_2$H$_5$ | Resin |
| 4.37 | CH | OCH$_3$ | CH$_2$C$_6$H$_4$-3-CF$_3$ | t-C$_4$H$_9$ | 89–91° |
| 4.38 | N | NHCH$_3$ | CH$_2$C$_6$H$_4$-2-F | C$_2$H$_5$ | 135–137° |
| 4.39 | CH | OCH$_3$ | —C$_6$H$_4$-4-Br | C$_2$H$_5$ | 93–95° |
| 4.40 | N | OCH$_3$ | —C$_6$H$_4$-4-Br | C$_2$H$_5$ | 94–97° |
| 4.41 | N | NHCH$_3$ | —C$_6$H$_4$-4-Br | C$_2$H$_5$ | 137–139° |
| 4.42 | CH | OCH$_3$ | CH$_2$C$_6$H$_4$-4-t-But | C$_2$H$_5$ | Resin |
| 4.43 | N | OCH$_3$ | CH$_2$C$_6$H$_4$-4-t-But | C$_2$H$_5$ | 101–103° |
| 4.44 | N | NHCH$_3$ | CH$_2$C$_6$H$_4$-4-t-But | C$_2$H$_5$ | 133–135° |
| 4.45 | CH | OCH$_3$ | CH$_2$C$_6$H$_3$-2,4-Cl$_2$ | C$_2$H$_5$ | 107–109° |
| 4.46 | N | OCH$_3$ | CH$_2$C$_6$H$_3$-2,4-Cl$_2$ | C$_2$H$_5$ | 103–105° |
| 4.47 | N | NHCH$_3$ | CH$_2$C$_6$H$_3$-2,4-Cl$_2$ | C$_2$H$_5$ | 98–100° |
| 4.48 | N | OCH$_3$ | —C$_6$H$_3$-2,4-Cl$_2$ | C$_2$H$_5$ | 141–143° |
| 4.49 | N | OCH$_3$ | C$_6$H$_4$-4-t-But | C$_2$H$_5$ | 92–94° |
| 4.50 | N | OCH$_3$ | C$_6$H$_4$-3-Cl | C$_2$H$_5$ | 93–95° |
| 4.51 | CH | OCH$_3$ | C$_6$H$_3$-2,4-Cl$_2$ | C$_2$H$_5$ | 116–118° |
| 4.52 | N | NHCH$_3$ | C$_6$H$_3$-2,4-Cl$_2$ | C$_2$H$_5$ | 147–148° |
| 4.53 | N | NHCH$_3$ | C$_6$H$_4$-4-t-But | C$_2$H$_5$ | 68–69° |
| 4.54 | N | NHCH$_3$ | C$_6$H$_4$-3-Cl | C$_2$H$_5$ | 90–92° |
| 4.55 | CH | OCH$_3$ | C$_6$H$_4$-4-t-But | C$_2$H$_5$ | 106–107° |
| 4.56 | CH | OCH$_3$ | C$_6$H$_4$-3-Cl | C$_2$H$_5$ | 85–87° |
| 4.57 | CH | OCH$_3$ | n-C$_3$H$_7$ | C$_2$H$_5$ | Oil |
| 4.58 | N | OCH$_3$ | n-C$_3$H$_7$ | C$_2$H$_5$ | 86–89° |
| 4.59 | N | NHCH$_3$ | n-C$_3$H$_7$ | C$_2$H$_5$ | 139–141° |
| 4.60 | CH | OCH$_3$ | n-C$_3$H$_7$ | n-C$_3$H$_7$ | Oil |
| 4.61 | N | OCH$_3$ | n-C$_3$H$_7$ | n-C$_3$H$_7$ | Oil |
| 4.62 | N | NHCH$_3$ | n-C$_3$H$_7$ | n-C$_3$H$_7$ | 128–131° |
| 4.63 | CH | OCH$_3$ | n-C$_3$H$_7$ | CH$_2$C≡CH | Resin |
| 4.64 | N | OCH$_3$ | n-C$_3$H$_7$ | CH$_2$C≡CH | 86–89° |
| 4.65 | N | NHCH$_3$ | n-C$_3$H$_7$ | CH$_2$C≡CH | Resin |
| 4.66 | CH | OCH$_3$ | CH$_2$C$_6$H$_4$-4-Cl | C$_2$H$_5$ | 77–79 |
| 4.67 | N | OCH$_3$ | CH$_2$C$_6$H$_4$-4-Cl | C$_2$H$_5$ | 111–112 |
| 4.68 | N | OCH$_3$ | C$_6$H$_4$-4-Cl | C$_2$H$_5$ | 90–93 |
| 4.69 | N | NHCH$_3$ | CH$_2$C$_6$H$_4$-4-Cl | C$_2$H$_5$ | 142–145 |
| 4.70 | N | NHCH$_3$ | C$_6$H$_4$-4-Cl | C$_2$H$_5$ | 126–129 |
| 4.71 | N | OCH$_3$ | C$_6$H$_3$-3,4-Cl$_2$ | C$_2$H$_5$ | 102–103 |
| 4.72 | CH | OCH$_3$ | C$_6$H$_3$-3,4-Cl$_2$ | C$_2$H$_5$ | 85–87 |
| 4.73 | N | NHCH$_3$ | C$_6$H$_3$-3,4-Cl$_2$ | C$_2$H$_5$ | 118–120 |
| 4.74 | N | OCH$_3$ | C$_6$H$_3$-2-Cl,4-Br | C$_2$H$_5$ | 127–129 |
| 4.75 | CH | OCH$_3$ | C$_6$H$_3$-2-Cl,4-Br | C$_2$H$_5$ | 104–106 |
| 4.76 | CH | OCH$_3$ | CH$_2$C$_6$H$_3$-3,4-Cl$_2$ | C$_2$H$_5$ | 94–96 |
| 4.77 | N | OCH$_3$ | CH$_2$C$_6$H$_3$-3,4-Cl$_2$ | C$_2$H$_5$ | 84–86 |
| 4.78 | N | NHCH$_3$ | CH$_2$C$_6$H$_3$-3,4-Cl$_2$ | C$_2$H$_5$ | 142–145 |

TABLE 4-continued

Compounds of the general formula

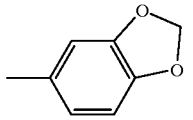

| Compd. | X | Y | R | AR₇ | Physical data |
|---|---|---|---|---|---|
| 4.79 | N | OCH₃ | 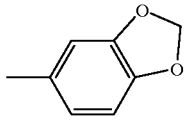 | C₂H₅ | 84–86 |
| 4.80 | CH | OCH₃ | 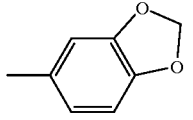 | C₂H₅ | Resin |
| 4.81 | N | OCH₃ | C₆H₄-4-Cl | CH₂C≡CH | 93–95 |
| 4.82 | N | OCH₃ | C₆H₄-4-Cl | (CH₂)₂CH₃ | 95–96 |
| 4.83 | N | OCH₃ | C₆H₄-2-Cl | C₂H₅ | 107–109 |
| 4.84 | CH | OCH₃ | C₆H₄-2-Cl | C₂H₅ | 119–121 |
| 4.85 | N | NHCH₃ | C₆H₃-2-Cl, 4-Br | C₂H₅ | 138–140 |
| 4.86 | N | NHCH₃ | (benzodioxole) | C₂H₅ | 142–144 |
| 4.87 | CH | OCH₃ | C₆H₄-4-Cl | CH₂C≡CH | 103–105 |
| 4.88 | CH | OCH₃ | C₆H₄-4-Cl | (CH₂)₂CH₃ | 90–92 |
| 4.89 | N | NHCH₃ | C₆H₄-4-Cl | CH₂C≡CH | 130–132 |
| 4.90 | N | NHCH₃ | C₆H₄-4-Cl | (CH₂)₂CH₃ | 96–98 |
| 4.91 | N | NHCH₃ | C₆H₄-2-Cl | C₂H₅ | 128–130 |
| 4.92 | N | OCH₃ | C₆H₅-4-SCH₃ | C₂H₅ | Resin |
| 4.93 | CH | OCH₃ | C₆H₅-4-SCH₃ | C₂H₅ | 97–99 |
| 4.94 | N | NHCH₃ | C₆H₅-4-SCH₃ | C₂H₅ | 118–120 |
| 4.95 | N | OCH₃ | C₆H₄-4-Cl | CH₂CH=CH₂ | 74–76 |
| 4.96 | N | OCH₃ | C₆H₄-4-Cl | i-C₃H₇ | 75–77 |
| 4.97 | CH | OCH₃ | C₆H₄-4-Cl | CH₂CH=CH₂ | 73–75 |
| 4.98 | CH | OCH₃ | C₆H₄-4-Cl | i-C₃H₇ | Resin |
| 4.99 | N | NHCH₃ | C₆H₄-4-Cl | CH₂CH=CH₂ | 101–103 |
| 4.100 | N | NHCH₃ | C₆H₄-4-Cl | i-C₃H₇ | 104–105 |
| 4.101 | CH | OCH₃ | C₆H₄-3-CF₃ | CH₂C≡CH | Resin |
| 4.102 | N | OCH₃ | CH₂C₆H₄-4-CF₃ | CH₂C≡CH | 104–106 |
| 4.103 | N | OCH₃ | CH₂C₆H₄-4-CF₃ | CH₂CH=CH₂ | 93–95 |
| 4.104 | N | OCH₃ | CH₂C₆H₄-4-CF₃ | n-C₃H₇ | 87–88 |
| 4.105 | CH | OCH₃ | CH₂C₆H₄-4-CF₃ | n-C₃H₇ | 88–89 |
| 4.106 | N | NHCH₃ | CH₂C₆H₄-4-CF₃ | CH₂C≡CH | 114–116 |
| 4.107 | N | NHCH₃ | CH₂C₆H₄-4-CF₃ | CH₂CH=CH₂ | 115–117 |
| 4.108 | H | OCH₃ | CH₂C₆H₄-4-CF₃ | CH₂C≡CH | 121–123 |
| 4.109 | CH | OCH₃ | CH₂C₆H₄-4-CF₃ | CH₂CH=CH₂ | 82–84 |
| 4.110 | N | NHCH₃ | CH₂C₆H₄-4-CF₃ | n-C₃H₇ | 132–134 |
| 4.111 | N | OCH₃ | C₆H₃-2,4-F₂ | C₂H₅ | 90–92 |
| 4.112 | CH | OCH₃ | C₆H₃-2,4-F₂ | C₂H₅ | 90–92 |
| 4.113 | CH | OCH₃ | C₆H₄-4-OCF₃ | C₂H₅ | 102–104 |
| 4.114 | N | OCH₃ | C₆H₄-4-OCF₃ | C₂H₅ | 70–72 |
| 4.115 | N | NHCH₃ | C₆H₃-2,4-F₂ | C₂H₅ | 125–127 |
| 4.116 | N | OCH₃ | C₆H₄-4-F | C₂H₅ | 91–93 |
| 4.117 | N | NHCH₃ | C₆H₄-4-OCF₃ | C₂H₅ | 119–121 |
| 4.118 | CH | OCH₃ | C₆H₄-4-F | C₂H₅ | 88–90 |
| 4.119 | N | OCH₃ | C₆H₄-4-CH₃ | C₂H₅ | 75–77 |
| 4.120 | N | NHCH₃ | C₆H₄-4-F | C₂H₅ | 118–120 |

TABLE 4-continued

Compounds of the general formula

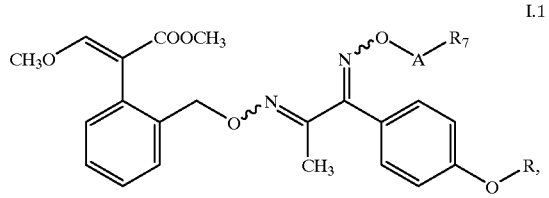

| Compd. | X | Y | R | AR₇ | Physical data |
|---|---|---|---|---|---|
| 4.121 | N | OCH₃ | C₆H₄-4-Cl | n-C₄H₉ | 102–104 |
| 4.122 | N | OCH₃ | C₆H₄-4-OC₆H₅ | C₂H₅ | 95–97 |
| 4.123 | CH | OCH₃ | C₆H₄-4-Cl | CH₂OC₂H₅ | Resin |
| 4.124 | N | NHCH₃ | C₆H₄-4-Cl | n-C₄H₉ | Resin |
| 4.125 | CH | OCH₃ | C₆H₄-4-OC₆H₅ | C₂H₅ | 101–103 |
| 4.126 | N | NHCH₃ | C₆H₄-4-OC₆H₅ | C₂H₅ | 82–84 |
| 4.127 | N | OCH₃ | C₆H₄-4-Cl | CH₂OC₂H₅ | 104–106 |
| 4.128 | CH | OCH₃ | C₆H₄-4-Cl | n-C₄H₉ | Resin |
| 4.129 | N | NHCH₃ | C₆H₄-4-Cl | CH₂OC₂H₅ | Resin |
| 4.130 | CH | OCH₃ | C₆H₄-4-CH₃ | C₂H₅ | 102–104 |
| 4.131 | N | NHCH₃ | C₆H₄-4-CH₃ | C₂H₅ | 116–118 |
| 4.132 | N | OCH₃ | C₆H₄-4-OCH₃ | C₂H₅ | 76–79 |
| 4.133 | CH | OCH₃ | C₆H₄-4-OCH₃ | C₂H₅ | 98–100 |
| 4.134 | N | NHCH₃ | C₆H₄-4-OCH₃ | C₂H₅ | 125–127 |
| 4.135 | N | OCH₃ | 2-Naphtyl | C₂H₅ | 103–106 |
| 4.136 | CH | OCH₃ | 2-Naphtyl | C₂H₅ | 93–96 |
| 4.137 | N | OCH₃ | C₆H₄-4-CN | C₂H₅ | 113–116 |
| 4.138 | CH | OCH₃ | C₆H₄-4-CN | C₂H₅ | 105–107 |
| 4.139 | N | NHCH₃ | 2-Naphtyl | C₂H₅ | 148–150 |
| 4.140 | N | NHCH₃ | C₆H₄-4-CN | C₂H₅ | 146–148 |
| 4.141 | N | OCH₃ | C₆H₄-4-CF₃ | C₂H₅ | 111–113 |
| 4.142 | N | OCH₃ | C₆H₄-4-CF₃ | CH₂C≡CH | 98–100 |
| 4.143 | N | NHCH₃ | C₆H₄-4-CF₃ | CH₂C≡CH | 117–118 |
| 4.144 | CH | OCH₃ | C₆H₄-4-CF₃ | C₂H₅ | 109–111 |
| 4.145 | CH | OCH₃ | C₆H₄-4-CF₃ | CH₂C≡CH | 102–104 |
| 4.146 | N | NHCH₃ | C₆H₄-4-CF₃ | C₂H₅ | 143–145 |
| 4.147 | CH | OCH₃ | CH₂-2-Naphtyl | C₂H₅ | 107–109 |
| 4.148 | N | OCH₃ | CH₂-2-Naphtyl | C₂H₅ | 86–89 |
| 4.149 | N | NHCH₃ | CH₂-2-Naphtyl | C₂H₅ | 148–150 |
| 4.150 | CH | OCH₃ | CH₂C₆H₄-4-CN | C₂H₅ | 80–84 |
| 4.151 | N | OCH₃ | CH₂C₆H₄-4-CN | C₂H₅ | 113–116 |
| 4.152 | N | NHCH₃ | CH₂C₆H₄-4-CN | C₂H₅ | 126–129 |

Table 5: Compounds of the general formula

I.1 in which R is CH₂Si(CH₃)₃ and the substituent A—R₇ for a compound in each case corresponds to a line of Table A.

Table 6: Compounds of the general formula I.1, in which R is CH₂C₆H₄-2-CF₃ and the substituent A—R₇ for a compound in each case corresponds to a line in Table A.

Table 7: Compounds of the general formula I.1, in which R is CH₂C₆H₄-3-CF₃ and the substituent A—R₇ for a compound in each case corresponds to a line in Table A.

Table 8: Compounds of the general formula I.1, in which R is CH₂C₆H₄-4-CF₃ and the substituent A—R₇ for a compound in each case corresponds to a line in Table A.

Table 9: Compounds of the general formula I.1, in which R is CH₂C₆H₄-2-F and the substituent A—R₇ for a compound in each case corresponds to a line in Table A.

Table 10: Compounds of the general formula I.1, in which R is CH₂C₆H₄-3-F and the substituent A—R₇ for a compound in each case corresponds to a line in Table A.

Table 11: Compounds of the general formula I.1, in which R is CH₂C₆H₄-4-F and the substituent A—R₇ for a compound in each case corresponds to a line in Table A.

Table 12: Compounds of the general formula I.1, in which R is CH₂C₆H₄-2-Cl and the substituent A—R₇ for a compound in each case corresponds to a line in Table A.

Table 13: Compounds of the general formula I.1, in which R is CH₂C₆H₄-3-Cl and the substituent A—R₇ for a compound in each case corresponds to a line in Table A.

Table 14: Compounds of the general formula I.1, in which R is CH₂C₆H₄-4-Cl and the substituent A—R₇ for a compound in each case corresponds to a line in Table A.

Table 15: Compounds of the general formula I.1, in which R is CH₂C₆H₄-2-Br and the substituent A—R₇ for a compound in each case corresponds to a line in Table A.

Table 16: Compounds of the general formula I.1, in which R is CH₂C₆H₄-3-Br and the substituent A—R₇ for a compound in each case corresponds to a line in Table A.

Table 17: Compounds of the general formula I.1, in which R is CH₂C₆H₄-4-Br and the substituent A—R₇ for a compound in each case corresponds to a line in Table A.

Table 18: Compounds of the general formula I.1, in which R is $C_6H_4$-2-F and the substituent A—$R_7$ for a compound in each case corresponds to a line in Table A.

Table 19: Compounds of the general formula I.1, in which R is $C_6H_4$-3-F and the substituent A—$R_7$ for a compound in each case corresponds to a line in Table A.

Table 20: Compounds of the general formula I.1, in which R is —$C_6H_4$-4-F and the substituent A—$R_7$ for a compound in each case corresponds to a line in Table A.

Table 21: Compounds of the general formula I.1, in which R is —$C_6H_4$-2-Cl and the substituent A—$R_7$ for a compound in each case corresponds to a line in Table A.

Table 22: Compounds of the general formula I.1, in which R is —$C_6H_4$-3-Cl and the substituent A—$R_7$ for a compound in each case corresponds to a line in Table A.

Table 23: Compounds of the general formula I.1, in which R is —$C_6H_4$-4-Cl and the substituent A—$R_7$ for a compound in each case corresponds to a line in Table A.

Table 24: Compounds of the general formula I.1, in which R is —$C_6H_4$-2-$CF_3$ and the substituent A—$R_7$ for a compound in each case corresponds to a line in Table A.

Table 25: Compounds of the general formula I.1, in which R is —$C_6H_4$-3-$CF_3$ and the substituent A—$R_7$ for a compound in each case corresponds to a line in Table A.

Table 26: Compounds of the general formula I.1, in which R is —$C_6H_4$-4-$CF_3$ and the substituent A—$R_7$ for a compound in each case corresponds to a line in Table A.

Table 27: Compounds of the general formula I.1, in which R is —$CH_2$-2,2-dichloro-1-cyclopropyl and the substituent A—$R_7$ for a compound in each case corresponds to a line in Table A.

Table 28: Compounds of the general formula I.1, in which R is —$CH_2$-2,2-dibromo-1-cyclopropyl and the substituent A—$R_7$ for a compound in each case corresponds to a line in Table A.

Table 29: Compounds of the general formula I.1, in which R is —$CH_2$-2,2-difluoro-1-cyclopropyl and the substituent A—$R_7$ for a compound in each case corresponds to a line in Table A.

Table 30: Compounds of the general formula I.1, in which R is —$CH_2C{\equiv}CH$ and the substituent A—$R_7$ for a compound in each case corresponds to a line in Table A.

Table 31: Compounds of the general formula I.1, in which R is —$CH_2CH{=}CH_2$ and the substituent A—$R_7$ for a compound in each case corresponds to a line in Table A.

Table 32: Compounds of the general formula I.1, in which R is —$CH_2CH{=}CHCH_3$ and the substituent A—$R_7$ for a compound in each case corresponds to a line in Table A.

Table 33: Compounds of the general formula I.1, in which R is —$CH_2CH{=}C(CH_3)_2$ and the substituent A—$R_7$ for a compound in each case corresponds to a line in Table A.

Table 34: Compounds of the general formula I.1, in which R is —$CH_2CH{=}CCl_2$ and the substituent A—$R_7$ for a compound in each case corresponds to a line in Table A.

Table 35: Compounds of the general formula I.1, in which R is —$CH(CH_3)CH{=}CH_2$ and the substituent A—$R_7$ for a compound in each case corresponds to a line in Table A.

Table 36: Compounds of the general formula I.1, in which R is —$C_6H_4$-2-Br and the substituent A—$R_7$ for a compound in each case corresponds to a line in Table A.

Table 37: Compounds of the general formula I.1, in which R is —$C_6H_4$-3-Br and the substituent A—$R_7$ for a compound in each case corresponds to a line in Table A.

Table 38: Compounds of the general formula I.1, in which R is —$C_6H_4$-4-Br and the substituent A—$R_7$ for a compound in each case corresponds to a line in Table A.

Table 39: Compounds of the general formula I.1, in which R is —$CH(CH_3)C_2H_5$ and the substituent A—$R_7$ for a compound in each case corresponds to a line in Table A.

Table 40: Compounds of the general formula I.1, in which R is —$CH_2CH(CH_3)_2$ and the substituent A—$R_7$ for a compound in each case corresponds to a line in Table A.

Table 41.1: Compounds of the general formula I.1, in which R is n-$C_4H_9$ and the substituent A—$R_7$ for a compound in each case corresponds to a line in Table A.

Table 41.2: Compounds of the general formula I.1, in which R is —$CH_2$-$C_6H_4$-4-t-butyl and the substituent A—$R_7$ for a compound in each case corresponds to a line in Table A.

Table 41.3: Compounds of the general formula I.1, in which R is —$CH_2$-$C_6H_3$-3,4-$Cl_2$ and the substituent A—$R_7$ for a compound in each case corresponds to a line in Table A.

Table 41.4: Compounds of the general formula I.1, in which R is —$CH_2$-$C_6H_3$-2,4-$Cl_2$ and the substituent A—$R_7$ for a compound in each case corresponds to a line in Table A.

Table 41.5: Compounds of the general formula I.1, in which R is —$C_6H_3$-2,4-$Cl_2$ and the substituent A—$R_7$ for a compound in each case corresponds to a line in Table A.

Table 41.6: Compounds of the general formula I.1, in which R is —$C_6H_3$-3,4-$Cl_2$ and the substituent A—$R_7$ for a compound in each case corresponds to a line in Table A.

Table 41.7: Compounds of the general formula I.1, in which R is —$C_6H_3$-2-Cl,4-Br and the substituent A—$R_7$ for a compound in each case corresponds to a line in Table A.

Table 41.8: Compounds of the general formula I.1, in which R is —$C_6H_3$-3,4-(—O—$CH_2$—O—) and the substituent A—$R_7$ for a compound in each case corresponds to a line in Table A.

Table 41.9: Compounds of the general formula I.1, in which R is —$C_6H_4$-4-$SCH_3$ and the substituent A—$R_7$ for a compound in each case corresponds to a line in Table A.

Table 41.10: Compounds of the general formula I.1, in which R is —$C_6H_4$-4-$OCF3$ and the substituent A—$R_7$ for a compound in each case corresponds to a line in Table A.

Table 41.11: Compounds of the general formula I.1, in which R is —$C_6H_4$-4-t-butyl and the substituent A—$R_7$ for a compound in each case corresponds to a line in Table A.

Table 41.12: Compounds of the general formula I.1, in which R is —$C_6H_4$-4-$OCH_3$ and the substituent A—$R_7$ for a compound in each case corresponds to a line in Table A.

Table 41.13: Compounds of the general formula I.1, in which R is —$C_6H_4$-4-$CH_3$ and the substituent A—$R_7$ for a compound in each case corresponds to a line in Table A.

Table 41.14: Compounds of the general formula I.1, in which R is 2-naphtyl and the substituent A—$R_7$ for a compound in each case corresponds to a line in Table A.

Table 41.15: Compounds of the general formula I.1, in which R is —$CH_2$-2-naphtyl and the substituent A—$R_7$ for a compound in each case corresponds to a line in Table A.

Table 41.16: Compounds of the general formula I.1, in which R is —$C_6H_4$-4-O—$C_6H_5$ and the substituent A—$R_7$ for a compound in each case corresponds to a line in Table A.

Table 41.17: Compounds of the general formula I.1, in which R is —$C_6H_4$-4-O—CN and the substituent A—$R_7$ for a compound in each case corresponds to a line in Table A.

Table 41.18: Compounds of the general formula I.1, in which R is —$CH_2C_6H_4$-4-CN and the substituent A—$R_7$ for a compound in each case corresponds to a line in Table A.

Table 41.19: Compounds of the general formula I.1, in which R is —$C_6H_3$-3-Cl-4-$CF_3$ and the substituent A—$R_7$ for a compound in each case corresponds to a line in Table A.

Table 41.20: Compounds of the general formula I.1, in which R is —$C_6H_3$-2-Cl-4-$CF_3$ and the substituent A—$R_7$ for a compound in each case corresponds to a line in Table A.

TABLE A

| Compound No. | A—$R_7$ |
|---|---|
| A.1 | $C_2H_5$ |
| A.2 | n-$C_3H_7$ |
| A.3 | i-$C_3H_7$ |
| A.4 | n-$C_4H_9$ |
| A.5 | n-$C_6H_{13}$ |
| A.6 | $CH_2F$ |
| A.7 | $CHF_2$ |
| A.8 | $CH_2CF_3$ |
| A.9 | $CH_2CH=CH_2$ |
| A.10 | $CH_2CH=CHCH_3$ |
| A.11 | $CH_2CH=C(CH_3)_2$ |
| A.12 | $CH_2CH=CHCl$ |
| A.13 | $CH_2CH=CCl_2$ |
| A.14 | $CH_2C(CH_3)=CH_2$ |
| A.15 | $CH_2C\equiv CH$ |
| A.16 | $CH_2Si(CH_3)_3$ |
| A.17 | $CH_2$-c.propyl-2,2-$Cl_2$ |
| A.18 | $CH_2$-c.propyl |
| A.19 | $CH_2CN$ |
| A.20 | $CH_2COOCH_3$ |
| A.21 | $CH_2COOC_2H_5$ |
| A.22 | $CH_2COO$-i-$C_3H_7$ |
| A.23 | $CH(CH_3)COOC_2H_5$ |
| A.24 | $C(=O)OC_2H_5$ |
| A.25 | $C(=O)NHCH_3$ |
| A.26 | $C(=O)C(=O)OC_2H_5$ |
| A.27 | $CH_2C_6H_5$ |
| A.28 | $CH_2C_6H_4$-2-F |
| A.29 | $CH_2C_6H_4$-3-F |
| A.30 | $CH_2C_6H_4$-4-F |
| A.31 | $CH_2C_6H_4$-2-Cl |
| A.32 | $CH_2C_6H_4$-3-Cl |
| A.33 | $CH_2C_6H_4$-4-Cl |
| A.34 | $CH_2C_6H_4$-2-Br |
| A.35 | $CH_2C_6H_4$-3-Br |
| A.36 | $CH_2C_6H_4$-4-Br |
| A.37 | $CH_2C_6H_4$-2-$CF_3$ |
| A.38 | $CH_2C_6H_4$-3-$CF_3$ |
| A.39 | $CH_2C_6H_4$-4-$CF_3$ |

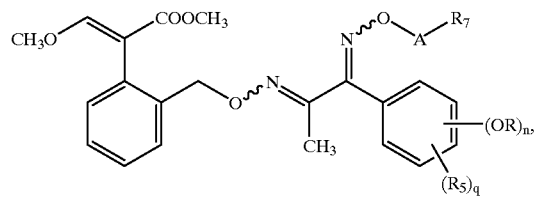

in which the combination of substituents $(R_5)_n$, $(OR)_q$ and A—$R_7$ for a compound in each case corresponds to a line in Table B. Their physical data are listed in the following Table. The compound numbers correspond to those of Table B.

| Compound No. | Physical Data | Compound No. | Physical data |
|---|---|---|---|
| 42.3 | Resin | 42.79 | Resin |
| 42.12 | Resin | 42.80 | Oil |
| 42.14 | Resin | 42.81 | Resin |
| 42.20 | Resin | 42.82 | Resin |
| 42.21 | Resin | | |

TABLE B

| Compound No. | $(R_5)_q$ | $(OR)_n$ | A—$R_7$ |
|---|---|---|---|
| B.1 | — | 2-$OCH_3$ | $CH_2CF_3$ |
| B.2 | — | 3-$OCH_3$ | $CH_2CF_3$ |
| B.3 | — | 4-$OCH_3$ | $CH_2CF_3$ |
| B.4 | — | 2-$OC_2H_5$ | $CH_2CF_3$ |
| B.5 | — | 3-$OC_2H_5$ | $CH_2CF_3$ |
| B.6 | — | 4-$OC_2H_5$ | $CH_2CF_3$ |
| B.7 | — | 4-O-n-$C_3H_7$ | $CH_2CF_3$ |
| B.8 | — | 4-O-i-$C_3H_7$ | $CH_2CF_3$ |
| B.9 | — | 4-O-n-$C_5H_{11}$ | $CH_2CF_3$ |
| B.10 | — | 4-O-$C_6H_{13}$ | $CH_2CF_3$ |
| B.11 | — | 4-O-t-Butyl | $CH_2CF_3$ |
| B.12 | 2-$CH_3$ | — | $CH_2CF_3$ |
| B.13 | 3-$CH_3$ | — | $CH_2CF_3$ |
| B.14 | 4-$CH_3$ | — | $CH_2CF_3$ |
| B.15 | 2-$C_2H_5$ | — | $CH_2CF_3$ |
| B.16 | 3-$C_2H_5$ | — | $CH_2CF_3$ |
| B.17 | 4-$C_2H_5$ | — | $CH_2CF_3$ |
| B.18 | 2-$CF_3$ | — | $CH_2CF_3$ |
| B.19 | 3-$CF_3$ | — | $CH_2CF_3$ |
| B.20 | 4-$CF_3$ | — | $CH_2CF_3$ |
| B.21 | 4-$SCH_3$ | — | $CH_2CF_3$ |
| B.22 | 2-Cl | — | $CH_2CF_3$ |
| B.23 | 3-Cl | — | $CH_2CF_3$ |
| B.24 | 4-Cl | — | $CH_2CF_3$ |
| B.25 | 2-Br | — | $CH_2CF_3$ |
| B.26 | 4-Br | — | $CH_2CF_3$ |
| B.27 | — | 2-$OCH_3$ | $CH_2F$ |
| B.28 | — | 3-$OCH_3$ | $CH_2F$ |
| B.29 | — | 4-$OCH_3$ | $CH_2F$ |
| B.30 | — | 2-$OC_2H_5$ | $CH_2F$ |
| B.31 | — | 3-$OC_2H_5$ | $CH_2F$ |
| B.32 | — | 4-$OC_2H_5$ | $CH_2F$ |
| B.33 | — | 4-O-n-$C_3H_7$ | $CH_2F$ |
| B.34 | — | 4-O-i-$C_3H_7$ | $CH_2F$ |
| B.35 | — | 4-O-n-$C_5H_{11}$ | $CH_2F$ |
| B.36 | — | 4-O-$C_6H_{13}$ | $CH_2F$ |
| B.37 | — | 4-O-t-butyl | $CH_2F$ |
| B.38 | 2-$CH_3$ | — | $CH_2F$ |
| B.39 | 3-$CH_3$ | — | $CH_2F$ |
| B.40 | 4-$CH_3$ | — | $CH_2F$ |
| B.41 | 2-$C_2H_5$ | — | $CH_2F$ |
| B.42 | 3-$C_2H_5$ | — | $CH_2F$ |
| B.43 | 4-$C_2H_5$ | — | $CH_2F$ |
| B.44 | 2-$CF_3$ | — | $CH_2F$ |
| B.45 | 3-$CF_3$ | — | $CH_2F$ |
| B.46 | 4-$CF_3$ | — | $CH_2F$ |
| B.47 | 4-$SCH_3$ | — | $CH_2F$ |
| B.48 | 2-Cl | — | $CH_2F$ |
| B.49 | 3-Cl | — | $CH_2F$ |
| B.50 | 4-Cl | — | $CH_2F$ |
| B.51 | 2-Br | — | $CH_2F$ |
| B.52 | 4-Br | — | $CH_2F$ |
| B.53 | — | 2-$OCH_3$ | $CHF_2$ |
| B.54 | — | 3-$OCH_3$ | $CHF_2$ |
| B.55 | — | 4-$OCH_3$ | $CHF_2$ |
| B.56 | — | 2-$OC_2H_5$ | $CHF_2$ |
| B.57 | — | 3-$OC_2H_5$ | $CHF_2$ |
| B.58 | — | 4-$OC_2H_5$ | $CHF_2$ |
| B.59 | — | 4-O-n-$C_3H_7$ | $CHF_2$ |
| B.60 | — | 4-O-i-$C_3H_7$ | $CHF_2$ |
| B.61 | — | 4-O-n-$C_5H_{11}$ | $CHF_2$ |
| B.62 | — | 4-O-$C_6H_{13}$ | $CHF_2$ |
| B.63 | — | 4-O-t-butyl | $CHF_2$ |
| B.64 | 2-$CH_3$ | — | $CHF_2$ |
| B.65 | 3-$CH_3$ | — | $CHF_2$ |
| B.66 | 4-$CH_3$ | — | $CHF_2$ |
| B.67 | 2-$C_2H_5$ | — | $CHF_2$ |
| B.68 | 3-$C_2H_5$ | — | $CHF_2$ |
| B.69 | 4-$C_2H_5$ | — | $CHF_2$ |
| B.70 | 2-$CF_3$ | — | $CHF_2$ |
| B.71 | 3-$CF_3$ | — | $CHF_2$ |
| B.72 | 4-$CF_3$ | — | $CHF_2$ |
| B.73 | 4-$SCH_3$ | — | $CHF_2$ |
| B.74 | 2-Cl | — | $CHF_2$ |
| B.75 | 3-Cl | — | $CHF_2$ |
| B.76 | 4-Cl | — | $CHF_2$ |
| B.77 | 2-Br | — | $CHF_2$ |

TABLE B-continued

| Compound No. | $(R_5)_q$ | $(OR)_n$ | A—$R_7$ |
|---|---|---|---|
| B.78 | 4-Br | — | $CHF_2$ |
| B.79 | 2,4-$F_2$ | | $C_2H_5$ |
| B.80 | 2,4-$F_2$ | | $CH_2$—CH=$CH_2$ |
| B.81 | 2,4-$F_2$ | | $CH_2C\equiv CH$ |
| B.82 | 2,4-$F_2$ | | H |

Table 43: Compounds of the general formula $$I.2$$

in which R is $CH_2Si(CH_3)_3$ and the substituent A—$R_7$, for a compound in each case corresponds to a line in Table A.

Table 44: Compounds of the general formula I.2, in which R is $CH_2C_6H_4$-2-$CF_3$ and the substituent A—$R_7$ for a compound in each case corresponds to a line in Table A.

Table 45: Compounds of the general formula I.2, in which R is $CH_2C_6H_4$-3-$CF_3$ and the substituent A—$R_7$ for a compound in each case corresponds to a line in Table A.

Table 46: Compounds of the general formula I.2, in which R is $CH_2C_6H_4$-4-$CF_3$ and the substituent A—$R_7$ for a compound in each case corresponds to a line in Table A.

Table 47: Compounds of the general formula I.2, in which R is $CH_2C_6H_4$-2-F and the substituent A—$R_7$ for a compound in each case corresponds to a line in Table A.

Table 48: Compounds of the general formula I.2, in which R is $CH_2C_6H_4$-3-F and the substituent A—$R_7$ for a compound in each case corresponds to a line in Table A.

Table 49: Compounds of the general formula I.2, in which R is $CH_2C_6H_4$-4-F and the substituent A—$R_7$ for a compound in each case corresponds to a line in Table A.

Table 50: Compounds of the general formula I.2, in which R is $CH_2C_6H_4$-2-Cl and the substituent A—$R_7$ for a compound in each case corresponds to a line in Table A.

Table 51: Compounds of the general formula I.2, in which R is $CH_2C_6H_4$-3-Cl and the substituent A—$R_7$ for a compound in each case corresponds to a line in Table A.

Table 52: Compounds of the general formula I.2, in which R is $CH_2C_6H_4$-4-Cl and the substituent A—$R_7$ for a compound in each case corresponds to a line in Table A.

Table 53: Compounds of the general formula I.2, in which R is $CH_2C_6H_4$-2-Br and the substituent A—$R_7$ for a compound in each case corresponds to a line in Table A.

Table 54: Compounds of the general formula I.2, in which R is $CH_2C_6H_4$-3-Br and the substituent A—$R_7$ for a compound in each case corresponds to a line in Table A.

Table 55: Compounds of the general formula I.2, in which R is $CH_2C_6H_4$-4-Br and the substituent A—$R_7$ for a compound in each case corresponds to a line in Table A.

Table 56: Compounds of the general formula I.2, in which R is $C_6H_4$-2-F and the substituent A—$R_7$ for a compound in each case corresponds to a line in Table A.

Table 57: Compounds of the general formula I.2, in which R is $C_6H_4$-3-F and the substituent A—$R_7$ for a compound in each case corresponds to a line in Table A.

Table 58: Compounds of the general formula I.2, in which R is $C_6H_4$-4-F and the substituent A—$R_7$ for a compound in each case corresponds to a line in Table A.

Table 59: Compounds of the general formula I.2, in which R is $C_6H_4$-2-Cl and the substituent A—$R_7$ for a compound in each case corresponds to a line in Table A.

Table 60: Compounds of the general formula I.2, in which R is $C_6H_4$-3-Cl and the substituent A—$R_7$ for a compound in each case corresponds to a line in Table A.

Table 61: Compounds of the general formula I.2, in which R is $C_6H_4$-4-Cl and the substituent A—$R_7$ for a compound in each case corresponds to a line in Table A.

Table 62: Compounds of the general formula I.2, in which R is $C_6H_4$-2-$CF_3$ and the substituent A—$R_7$ for a compound in each case corresponds to a line in Table A.

Table 63: Compounds of the general formula I.2, in which R is $C_6H_4$-3-$F_3$ and the substituent A—$R_7$ for a compound in each case corresponds to a line in Table A.

Table 64: Compounds of the general formula I.2, in which R is $C_6H_4$-4-$CF_3$ and the substituent A—$R_7$ for a compound in each case corresponds to a line in Table A.

Table 65: Compounds of the general formula I.2, in which R is $CH_2$-2,2-dichloro-1-cyclopropyl and the substituent A—$R_7$ for a compound in each case corresponds to a line in Table A.

Table 66: Compounds of the general formula I.2, in which R is $CH_2$-2,2-dibromo-1-cyclopropyl and the substituent A—$R_7$ for a compound in each case corresponds to a line in Table A.

Table 67: Compounds of the general formula I.2, in which R is $CH_2$-2,2-difluoro-1-cyclopropyl and the substituent A—$R_7$ for a compound in each case corresponds to a line in Table A.

Table 68: Compounds of the general formula I.2, in which R is $CH_2C\equiv CH$ and the substituent A—$R_7$ for a compound in each case corresponds to a line in Table A.

Table 69: Compounds of the general formula I.2, in which R is $CH_2CH=CH_2$ and the substituent A—$R_7$ for a compound in each case corresponds to a line in Table A.

Table 70: Compounds of the general formula I.2, in which R is $CH_2CH=CHCH_3$ and the substituent A—$R_7$ for a compound in each case corresponds to a line in Table A.

Table 71: Compounds of the general formula I.2, in which R is $CH_2CH=C(CH_3)_2$ and the substituent A—$R_7$ for a compound in each case corresponds to a line in Table A.

Table 72: Compounds of the general formula I.2, in which R is $CH_2CH=CCl_2$ and the substituent A—$R_7$ for a compound in each case corresponds to a line in Table A.

Table 73: Compounds of the general formula I.2, in which R is $CH(CH_3)CH=CH_2$ and the substituent A—$R_7$ for a compound in each case corresponds to a line in Table A.

Table 74: Compounds of the general formula I.2, in which R is $C_6H_4$-2-Br and the substituent A—$R_7$ for a compound in each case corresponds to a line in Table A.

Table 75: Compounds of the general formula I.2, in which R is $C_6H_4$-3-Br and the substituent A—$R_7$ for a compound in each case corresponds to a line in Table A.

Table 76: Compounds of the general formula I.2, in which R is $C_6H_4$-4-Br and the substituent A—$R_7$ for a compound in each case corresponds to a line in Table A.

Table 77: Compounds of the general formula I.2, in which R is $CH(CH_3)C_2H_5$ and the substituent A—$R_7$ for a compound in each case corresponds to a line in Table A.

Table 78: Compounds of the general formula I.2, in which R is $CH_2CH(CH_3)_2$ and the substituent A—$R_7$ for a compound in each case corresponds to a line in Table A.

Table 79.1: Compounds of the general formula I.2, in which R is n-$C_4H_9$ and the substituent A—$R_7$ for a compound in each case corresponds to a line in Table A.

Table 79.2: Compounds of the general formula I.2, in which R is $CH_2$—$C_6H_4$-4-t-butyl and the substituent A—$R_7$ for a compound in each case corresponds to a line in Table A.

Table 79.3: Compounds of the general formula I.2, in which R is $CH_2$—$C_5H_3$-3,4-$Cl_2$ and the substituent A—$R_7$ for a compound in each case corresponds to a line in Table A.

Table 79.4: Compounds of the general formula I.2, in which R is $CH_2$—$C_6H_3$-2,4-$Cl_2$ and the substituent A—$R_7$ for a compound in each case corresponds to a line in Table A.

Table 79.5: Compounds of the general formula I.2, in which R is $C_6H_3$-2,4-$Cl_2$ and the substituent A—$R_7$ for a compound in each case corresponds to a line in Table A.

Table 79.6: Compounds of the general formula I.2, in which R is $C_6H_3$-3,4-$Cl_2$ and the substituent A—$R_7$ for a compound in each case corresponds to a line in Table A.

Table 79.7: Compounds of the general formula I.2, in which R is $C_6H_3$-2-Cl,4-Br and the substituent A—$R_7$ for a compound in each case corresponds to a line in Table A.

Table 79.8: Compounds of the general formula I.2, in which R is $C_6H_3$-3,4-(—O—$CH_2$—O—) and the substituent A—$R_7$ for a compound in each case corresponds to a line in Table A.

Table 79.9: Compounds of the general formula I.2, in which R is $C_6H_4$-4-$SCH_3$ and the substituent A—$R_7$ for a compound in each case corresponds to a line in Table A.

Table 79.10: Compounds of the general formula I.2, in which R is $C_6H_4$-4-$OCF3$ and the substituent A—$R_7$ for a compound in each case corresponds to a line in Table A.

Table 79.11: Compounds of the general formula I.2, in which R is $C_6H_4$-4-t-butyl and the substituent A—$R_7$ for a compound in each case corresponds to a line in Table A.

Table 79.12: Compounds of the general formula I.2, in which R is $C_6H_4$-4-$OCH_3$ and the substituent A—$R_7$ for a compound in each case corresponds to a line in Table A.

Table 79.13: Compounds of the general formula I.2, in which R is $C_6H_4$-4-$CH_3$ and the substituent A—$R_7$ for a compound in each case corresponds to a line in Table A.

Table 79.14: Compounds of the general formula I.1, in which R is 2-naphtyl and the substituent A—$R_7$ for a compound in each case corresponds to a line in Table A.

Table 79.15: Compounds of the general formula I.1, in which R is —$CH_2$-2-naphtyl and the substituent A—$R_7$ for a compound in each case corresponds to a line in Table A.

Table 79.16: Compounds of the general formula I.1, in which R is —$C_6H_4$-4-O—$C_6H_5$ and the substituent A—$R_7$ for a compound in each case corresponds to a line in Table A.

Table 79.17: Compounds of the general formula I.1, in which R is —$C_6H_4$-4-CN and the substituent A—$R_7$ for a compound in each case corresponds to a line in Table A.

Table 79.18: Compounds of the general formula I.1, in which R is —$CH_2C_6H_4$-4-CN and the substituent A—$R_7$ for a compound in each case corresponds to a line in Table A.

Table 79.19: Compounds of the general formula I.2, in which R is —$C_6H_3$-3-Cl-4-$CF_3$ and the substituent A—$R_7$ for a compound in each case corresponds to a line in Table A.

Table 79.20: Compounds of the general formula I.2, in which R is —$C_6H_3$-2-Cl-4-$CF_3$ and the substituent A—$R_7$ for a compound in each case corresponds to a line in Table A.

Table 80: Compounds of the general formula in which the combination of substituents $R_5$, OR and A—$R_7$ for a compound in each case corresponds to a line in Table B.

| Compound No. | Physical data |
|---|---|
| 80.79 | Melting point 84–85° C. |
| 80.80 | Oil |
| 80.81 | Resin |

Table 81: Compounds of the general formula

I.3 in which R is $CH_2Si(CH_3)_3$ and the substituent A—$R_7$ for a compound in each case corresponds to a line in Table A.

Table 82: Compounds of the general formula I.3, in which R is $CH_2C_6H_4$-2-$CF_3$ and the substituent A—$R_7$ for a compound in each case corresponds to a line in Table A.

Table 83: Compounds of the general formula I.3, in which R is $CH_2C_6H_4$-3-$CF_3$ and the substituent A—$R_7$ for a compound in each case corresponds to a line in Table A.

Table 84: Compounds of the general formula I.3, in which R is $CH_2C_6H_4$-4-$CF_3$ and the substituent A—$R_7$ for a compound in each case corresponds to a line of Table A.

Table 85: Compounds of the general formula I.3, in which R is $CH_2C_6H_4$-2-F and the substituent A—$R_7$ for a compound in each case corresponds to a line of Table A.

Table 86: Compounds of the general formula I.3, in which R is $CH_2C_6H_4$-3-F and the substituent A—$R_7$ for a compound in each case corresponds to a line of Table A.

Table 87: Compounds of the general formula I.3, in which R is $CH_2C_6H_4$-4-F and the substituent A—$R_7$ for a compound in each case corresponds to a line of Table A.

Table 88: Compounds of the general formula I.3, in which R is $CH_2C_6H_4$-2-Cl and the substituent A—$R_7$ for a compound in each case corresponds to a line of Table A.

Table 89: Compounds of the general formula I.3, in which R is $CH_2C_6H_4$-3-Cl and the substituent A—$R_7$ for a compound in each case corresponds to a line of Table A.

Table 90: Compounds of the general formula I.3, in which R is $CH_2C_6H_4$-4-Cl and the substituent A—$R_7$ for a compound in each case corresponds to a line of Table A.

Table 91: Compounds of the general formula I.3, in which R is $CH_2C_6H_4$-2-Br and the substituent A—$R_7$ for a compound in each case corresponds to a line of Table A.

Table 92: Compounds of the general formula I.3, in which R is $CH_2C_6H_4$-3-Br and the substituent A—$R_7$ for a compound in each case corresponds to a line of Table A.

Table 93: Compounds of the general formula I.3, in which R is $CH_2C_6H_4$-4-Br and the substituent A—$R_7$ for a compound in each case corresponds to a line of Table A.

Table 94: Compounds of the general formula I.3, in which R is $C_6H_4$-2-F and the substituent A—$R_7$ for a compound in each case corresponds to a line of Table A.

Table 95: Compounds of the general formula I.3, in which R is $C_6H_4$-3-F and the substituent A—$R_7$ for a compound in each case corresponds to a line of Table A.

Table 96: Compounds of the general formula I.3, in which R is $C_6H_4$-4-F and the substituent A—$R_7$ for a compound in each case corresponds to a line of Table A.

Table 97: Compounds of the general formula I.3, in which R is $C_6H_4$-2-Cl and the substituent A—$R_7$ for a compound in each case corresponds to a line of Table A.

Table 98: Compounds of the general formula I.3, in which R is $C_6H_4$-3-Cl and the substituent A—$R_7$ for a compound in each case corresponds to a line of Table A.

Table 99: Compounds of the general formula I.3, in which R is $C_6H_4$-4-Cl and the substituent A—$R_7$ for a compound in each case corresponds to a line of Table A.

Table 100: Compounds of the general formula I.3, in which R is $C_6H_4$-2-$CF_3$ and the substituent A—$R_7$ for a compound in each case corresponds to a line of Table A.

Table 101: Compounds of the general formula I.3, in which R is $C_6H_4$-3-$CF_3$ and the substituent A—$R_7$ for a compound in each case corresponds to a line of Table A.

Table 102: Compounds of the general formula I.3, in which R is $C_6H_4$-4-$CF_3$ and the substituent A—$R_7$ for a compound in each case corresponds to a line of Table A.

Table 103: Compounds of the general formula I.3, in which R is $CH_2$-2,2-dichloro-1-cyclopropyl and the substituent A—$R_7$ for a compound in each case corresponds to a line of Table A.

Table 104: Compounds of the general formula I.3, in which R is $CH_2$-2,2-dibromo-1-cyclopropyl and the substituent A—$R_7$ for a compound in each case corresponds to a line of Table A.

Table 105: Compounds of the general formula I.3, in which R is $CH_2$-2,2-difluoro-1-cyclopropyl and the substituent A—$R_7$ for a compound in each case corresponds to a line of Table A.

Table 106: Compounds of the general formula I.3, in which R is $CH_2C{\equiv}CH$ and the substituent A—$R_7$ for a compound in each case corresponds to a line of Table A.

Table 107: Compounds of the general formula I.3, in which R is $CH_2CH{=}CH_2$ and the substituent A—$R_7$ for a compound in each case corresponds to a line of Table A.

Table 108: Compounds of the general formula I.3, in which R is $CH_2CH{=}CHCH_3$ and the substituent A—$R_7$ for a compound in each case corresponds to a line of Table A.

Table 109: Compounds of the general formula I.3, in which R is $CH_2CH{=}C(CH_3)_2$ and the substituent A—$R_7$ for a compound in each case corresponds to a line of Table A.

Table 110: Compounds of the general formula I.3, in which R is $CH_2CH{=}CCl_2$ and the substituent A—$R_7$ for a compound in each case corresponds to a line of Table A.

Table 111: Compounds of the general formula I.3, in which R is $CH(CH_3)CH{=}CH_2$ and the substituent A—$R_7$ for a compound in each case corresponds to a line of Table A.

Table 112: Compounds of the general formula I.3, in which R is $C_6H_4$-2-Br and the substituent A—$R_7$ for a compound in each case corresponds to a line of Table A.

Table 113: Compounds of the general formula I.3, in which R is $C_6H_4$-3-Br and the substituent A—$R_7$ for a compound in each case corresponds to a line of Table A.

Table 114: Compounds of the general formula I.3, in which R is $C_6H_4$-4-Br and the substituent A—$R_7$ for a compound in each case corresponds to a line of Table A.

Table 115: Compounds of the general formula I.3, in which R is $CH(CH_3)C_2H_5$ and the substituent A—$R_7$ for a compound in each case corresponds to a line of Table A.

Table 116: Compounds of the general formula I.3, in which R is $CH_2CH(CH_3)_2$ and the substituent A—$R_7$ for a compound in each case corresponds to a line of Table A.

Table 117.1: Compounds of the general formula I.3, in which R is n-$C_4H_9$ and the substituent A—$R_7$ for a compound in each case corresponds to a line of Table A.

Table 117.2: Compounds of the general formula I.3, in which R is —$CH_2$—$C_6H_4$-4-t-butyl and the substituent A—$R_7$ for a compound in each case corresponds to a line of Table A.

Table 117.3: Compounds of the general formula I.3, in which R is —$CH_2$—$C_6H_3$-3,4-$Cl_2$ and the substituent A—$R_7$ for a compound in each case corresponds to a line of Table A.

Table 117.4: Compounds of the general formula I.3, in which R is —$CH_2$—$C_6H_3$-2,4-$Cl_2$ and the substituent A—$R_7$ for a compound in each case corresponds to a line of Table A.

Table 117.5: Compounds of the general formula I.3, in which R is —$C_6H_3$-2,4-$Cl_2$ and the substituent A—$R_7$ for a compound in each case corresponds to a line of Table A.

Table 117.6: Compounds of the general formula I.3, in which R is —$C_6H_3$-3,4-$Cl_2$ and the substituent A—$R_7$ for a compound in each case corresponds to a line of Table A.

Table 117.7: Compounds of the general formula I.3, in which R is —$C_6H_3$-2-$Cl_4$-Br and the substituent A—$R_7$ for a compound in each case corresponds to a line of Table A.

Table 117.8: Compounds of the general formula I.3, in which R is —$C_6H_3$-3,4-(—O—$CH_2$—O —) and the substituent A—$R_7$ for a compound in each case corresponds to a line of Table A.

Table 117.9: Compounds of the general formula I.3, in which R is —$C_6H_4$-4-$SCH_3$ and the substituent A—$R_7$ for a compound in each case corresponds to a line of Table A.

Table 117.10: Compounds of the general formula I.3, in which R is —$C_6H_4$-4-OCF3 and the substituent A—$R_7$ for a compound in each case corresponds to a line of Table A.

Table 117.11: Compounds of the general formula I.3, in which R is —$C_6H_4$-4-t-butyl and the substituent A—$R_7$ for a compound in each case corresponds to a line of Table A.

Table 117.12: Compounds of the general formula I.3, in which R is —$C_6H_4$-4-$OCH_3$ and the substituent A—$R_7$ for a compound in each case corresponds to a line of Table A.

Table 117.13: Compounds of the general formula I.3, in which R is —$C_6H_4$-4-$CH_3$ and the substituent A—$R_7$ for a compound in each case corresponds to a line of Table A.

Table 117.14: Compounds of the general formula I.3, in which R is 2-naphtyl and the substituent A—$R_7$ for a compound in each case corresponds to a line of Table A.

Table 117.15: Compounds of the general formula I.3, in which R is —$CH_2$-2-naphtyl and the substituent A—$R_7$ for a compound in each case corresponds to a line of Table A.

Table 117.16: Compounds of the general formula I.3, in which R is —$C_6H_4$-4-O—$C_6H_5$ and the substituent A—$R_7$ for a compound in each case corresponds to a line of Table A.

Table 117.17: Compounds of the general formula I.3, in which R is —$C_6H_4$-4-CN and the substituent A—$R_7$ for a compound in each case corresponds to a line of Table A.

Table 117.18: Compounds of the general formula I.3, in which R is —CH$_2$C$_6$H$_4$-4-CN and the substituent A—R$_7$ for a compound in each case corresponds to a line of Table A.

Table 117.19: Compounds of the general formula I.3, in which R is —C$_6$H$_3$-3-Cl-4-CF$_3$ and the substituent A—R$_7$ for a compound in each case corresponds to a line in Table A.

Table 117.20: Compounds of the general formula I.3, in which R is —C$_6$H$_3$-2-Cl-4-CF$_3$ and the substituent A—R$_7$ for a compound in each case corresponds to a line in Table A.

Table 118: Compounds of the general formula

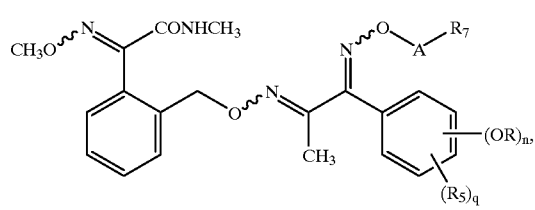

in which the combination of substituents R$_5$, OR and A—R$_7$ for a compound in each case corresponds to a line of Table B. Their physical data are listed in the following Table. The compound numbers correspond to those of Table B.

| Compound No. | Melting point |
|---|---|
| 118.79 | 121° C. |
| 118.80 | 95–96° C. |
| 118.81 | 106° C. |

Table 119: Compounds of the general formula

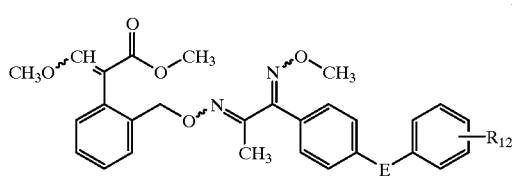

I.4 in which E is —CH$_2$— and the substituent R$_{12}$ in each case corresponds to a line in Table C.

| Compound | Isomer | Melting point |
|---|---|---|
| 119.2–1 | A | 122–124° C. |
| 119.2–2 | B | 99–102° C. |
| 119.3 | A | 101–103° C. |
| 119.4 | A | 98–101° C. |
| 119.5 | A | 149–151° C. |

Table 120: Compounds of the general formula

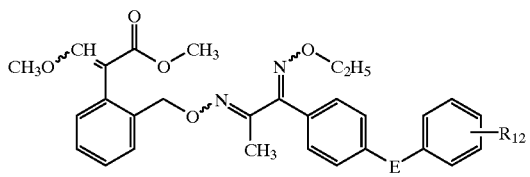

I.5 in which E is —CH$_2$— and R$_{12}$ in each case corresponds to a line in Table C. Their physical data are listed in the following Table. The compound numbers correspond to those in Table C.

| Compound | Isomer | Melting point |
|---|---|---|
| 120.2 | A | 125–126° C. |
| 120.3 | A | 90–92° C. |
| 120.4 | A | 100–101° C. |
| 120.5 | A | 110–112° C. |
| 120.6 | A | Harz |

Table 121: Compounds of the general formula

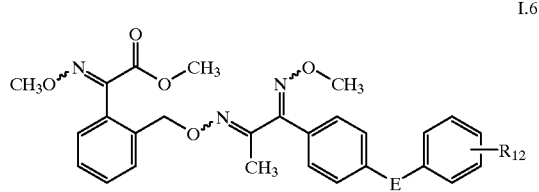

I.6 in which E is —CH$_2$— and R$_{12}$ in each case corresponds to a line in Table C. Their physical data are listed in the following Table. The compound numbers correspond to those in Table C.

| Compound | Isomer | Melting point |
|---|---|---|
| 121.2–1 | A | 103–104° C. |
| 121.2–2 | B | 111–113° C. |
| 121.3 | A | 104–106° C. |
| 121.4 | A | 91–92° C. |
| 121.5 | A | 98–100° C. |

Table 122: Compounds of the general formula

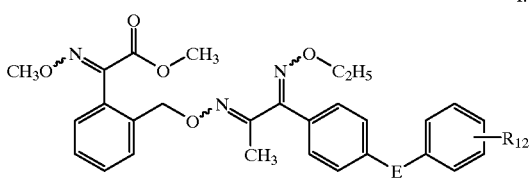

I.7 in which E is —CH$_2$— and R$_{12}$ in each case corresponds to a line in Table C. Their physical data are listed in the following Table. The compound numbers correspond to those in Table C.

| Compound | Isomer | Melting point |
|---|---|---|
| 122.2 | A | 86–88° C. |
| 122.3 | A | 80–83° C. |
| 122.4 | B | 86–88° C. |
| 122.5 | A | Harz |
| 122.6 | A | Harz |

Table 123: Compounds of the general formula

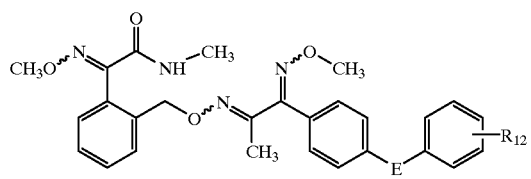
I.8 in which E is —$CH_2$— and $R_{12}$ in each case corresponds to a line in Table C.

| Compound | Isomer | Melting point |
|---|---|---|
| 123.2–1 | A | 163–165° C. |
| 123.2–2 | B | 98–102° C. |
| 123.3 | A | 159–161° C. |
| 123.4 | A | 146–148° C. |
| 123.5 | A | 172–173° C. |

Table 124: Compounds of the general formula

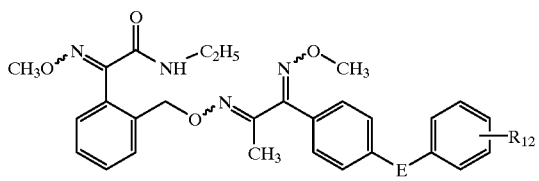
I.9 in which E is —$CH_2$— and $R_{12}$ in each case corresponds to a line in Table C.

Table 125: Compounds of the general formula

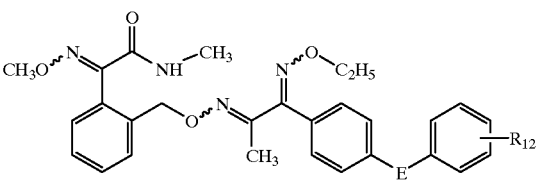
I.10 in which E is —$CH_2$— and $R_{12}$ in each case corresponds to a line in Table C.

| Compound | Isomer | Melting point |
|---|---|---|
| 125.2 | A | 156–158° C. |
| 125.3 | A | 132–134° C. |
| 125.4 | A | 146–147° C. |
| 125.5 | A | 142–143° C. |
| 125.6 | A | 131.132° C. |

Table 126: Compounds of the general formula

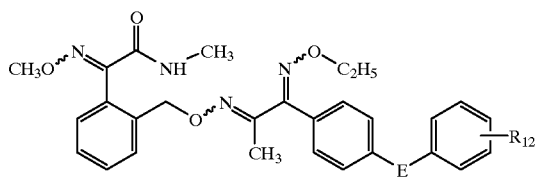
I.11 in which E is —$CH_2$— and $R_{12}$ in each case corresponds to a line in Table C.

Table 127: Compounds of the general formula

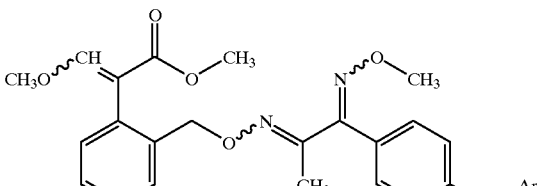
I.12 in which E is —$CH_2$— and the substituent Ar in each case corresponds to a line in Table D.

Table 128: Compounds of the general formula

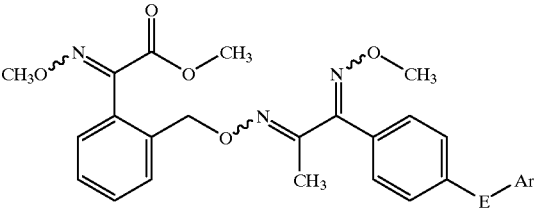
I.13 in which E is —$CH_2$— and Ar in each case corresponds to a line in Table D.

Table 129: Compounds of the general formula

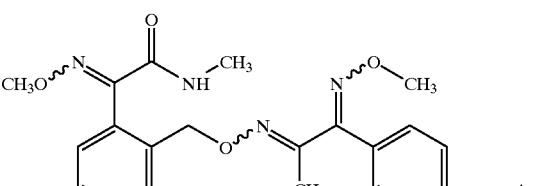
I.14 in which E is —$CH_2$— and Ar in each case corresponds to a line in Table D.

Table 130: Compounds of the general formula

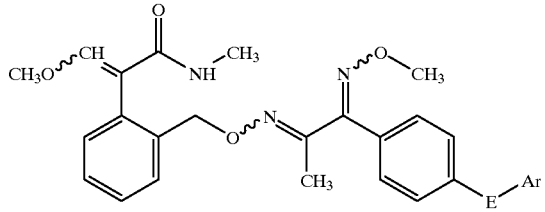

I.15 in which E is —CH₂— and Ar in each case corresponds to a line in Table D.

Example H3 a) Methyl 2-[[[(1-methyl-2-(4-(2-{2,4-dichlorophenyl}ethyl)-phenyl)-2-E-[methoxyimino]ethylidene)amino]oxy]methyl]-α-(methoxymethylene)-phenylacetate

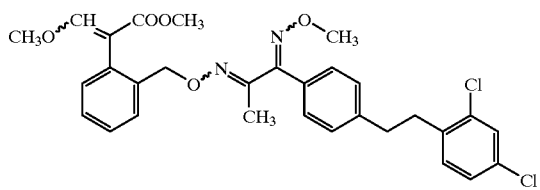

4 g of Pd (10% on active charcoal) are added to a solution of 4 g of methyl 2-[[[(1-methyl-2-(4-(2-{2,4-dichlorophenyl}ethynyl)-phenyl)-2-E-[methoxyimino]ethylidene)amino]oxy]-methyl]-α-(methoxymethylene)-phenylacetate in 80 ml of tetrahydrofuran, and 325.17 ml of hydrogen are passed in at 20° under normal pressure. The mixture is now filtered over SiO₂ (Celite) and the filtrate is evaporated. The residue is stirred in diisopropyl ether/petroleum ether 1:2 and the resulting solid is filtered off. The title compound with a melting point of 112–114° C. is obtained.

b) Methyl 2-[[[(1-methyl-2-(4-{2-pyrazinyl}ethenyl)-phenyl)-2-E-[methoxyimino]ethylidene)amino]oxy]methyl]-α-(methoxymethylene)-phenylacetate

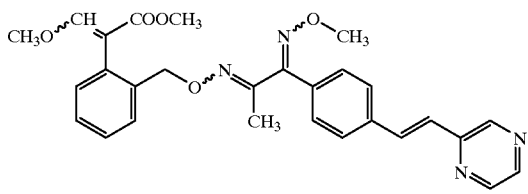

660 mg of Lindlar catalyst are added to a solution of 2.2 g of methyl 2-[[[(1-methyl-2-(4-{2-pyrazinyl}ethynyl)-phenyl)-2-E-[methoxyimino]ethylidene)amino]oxy]methyl]-α-(methoxymethylene)-phenylacetate in 80 ml of tetrahydrofuran, and 98.6 ml of hydrogen are passed in under normal pressure at 20°. The mixture is filtered under SiO₂ and the filtrate is evaporated. The residue is chromatographed over silica gel (eluent ethyl acetate/hexane 1:1). The title compound is obtained as a colourless resin.

c) Methyl 2-[[[(1-methyl-2-(4-{2-(3-chlorobenzoyl}ethyl)-phenyl)-2-E-[methoxyimino]-ethylidene)amino]oxy]methyl]-α-(methoxyimino)-phenylacetate

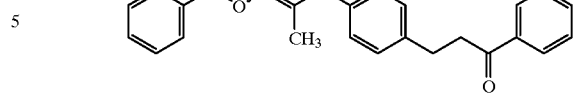

880 mg of Raney nickel are acided to a solution of 2.8 g of methyl 2-[[[(1-methyl-2-(4-{2-(3-chlorobenzoyl}ethynyl)-phenyl)-2-E-[methoxyimino]ethylidene)amino]oxy]-methyl]-α-(methoxyimino)-phenylacetate in 80 ml of tetrahydrofuran and 120 ml of ethyl acetate. 219.37 ml of hydrogen are passed in under normal pressure at 20° C. The mixture is filtered over SiO₂ and the filtrate is evaporated. The residue is chromatographed over silica gel (eluent diisopropyl ether/ether 1:1). The title compound with a melting point of 128–130° is obtained.

Example H4

The other compounds listed in Tables 131 to 154 can also be prepared in a manner analogous to that described in Examples H3 a) to c).

Table 131: Compounds of the general formula I.4, in which E is —CH₂—CH₂— and the substituent $R_{12}$ in each case corresponds to a line in Table C.

Table 132: Compounds of the general formula I.5, in which E is —CH₂—CH₂— and $R_{12}$ in each case corresponds to a line in Table C.

Table 133: Compounds of the general formula I.6, in which E is —CH₂—CH₂— and $R_{12}$ in each case corresponds to a line in Table C.

Table 134: Compounds of the general formula I.7, in which E is —CH₂—CH₂— and $R_{12}$ in each case corresponds to a line in Table C.

Table 135: Compounds of the general formula I.8, in which E is —CH₂—CH₂— and $R_{12}$ in each case corresponds to a line in Table C.

Table 136: Compounds of the general formula I.9, in which E is —CH₂—CH₂— and $R_{12}$ in each case corresponds to a line in Table C.

Table 137: Compounds of the general formula I.10, in which E is —CH₂—CH₂— and $R_{12}$ in each case corresponds to a line in Table C.

Table 138: Compounds of the general formula I.11, in which E is —CH₂—CH₂— and $R_{12}$ in each case corresponds to a line in Table C.

Table 139: Compounds of the general formula I.4, in which E is —CH=CH— and the substituent $R_{12}$ in each case corresponds to a line in Table C.

Table 140: Compounds of the general formula I.5, in which E is —CH=CH— and $R_{12}$ in each case corresponds to a line in Table C.

Table 141: Compounds of the general formula I.6, in which E is —CH=CH— and $R_{12}$ in each case corresponds to a line in Table C.

Table 142: Compounds of the general formula I.7, in which E is —CH=CH— and $R_{12}$ in each case corresponds to a line in Table C.

Table 143: Compounds of the general formula I.8, in which E is —CH=CH— and $R_{12}$ in each case corresponds to a line in Table C.

Table 144: Compounds of the general formula I.9, in which E is —CH=CH— and $R_{12}$ in each case corresponds to a line in Table C.

Table 145: Compounds of the general formula I.10, in which E is —CH=CH— and $R_{12}$ in each case corresponds to a line in Table C.

Table 146: Compounds of the general formula I.11, in which E is —CH=CH— and $R_{12}$ in each case corresponds to a line in Table C.

TABLE C

| Compound No. | $R_{12}$ |
|---|---|
| C.1 | H |
| C.2 | 4-Cl |
| C.3 | 3-Cl |
| C.4 | 3,4-$Cl_2$ |
| C.5 | 4-F |
| C.6 | 3-F |
| C.7 | $F_5$ |
| C.8 | 3,4-$F_2$ |
| C.9 | 4-O-$CF_3$ |
| C.10 | 3-O-$CF_3$ |
| C.11 | 4-$CF_3$ |
| C.12 | 3-$CF_3$ |
| C.13 | 3,5-$F_2$ |
| C.14 | 3,4,5-$F_3$ |
| C.15 | 3,4-CH=CH—CH=CH— |
| C.16 | 2,4-$Cl_2$ |
| C.17 | 4-$OCH_3$ |
| C.18 | 3,5-$CF_3$ |
| C.19 | 3,4-$Cl_2$ |
| C.20 | 2,4,6-$Cl_3$ |
| C.21 | 4-Br |
| C.22 | 3,4,5-$OCH_3$ |
| C.23 | 3,5-$(CH_3)_2$ |
| C.24 | 2,4-$Cl_2$ |
| C.25 | 4-$OCH_3$ |
| C.26 | 4-$CF_3$ |
| C.27 | 4-Br |
| C.28 | 3,4,5-$(OCH_3)_3$ |
| C.29 | 3,5-$(CH_3)_2$ |
| C.30 | 2-Cl |
| C.31 | 2,4-$F_2$ |
| C.32 | 2-F |

Table 147: Compounds of the general formula I.12, in which E is —$CH_2$—$CH_2$— and the substituent Ar in each case corresponds to a line in Table D.
Table 148: Compounds of the general formula I.12, in which E is —CH=CH— and the substituent Ar in each case corresponds to a line in Table D.
Table 149: Compounds of the general formula I.13, in which E is —$CH_2$—$CH_2$— and the substituent Ar in each case corresponds to a line in Table D.
Table 150: Compounds of the general formula I.13, in which E is —CH=CH— and the substituent Ar in each case corresponds to a line in Table D.
Table 151: Compounds of the general formula I.14, in which E is —$CH_2$—$CH_2$— and the substituent Ar in each case corresponds to a line in Table D.
Table 152: Compounds of the general formula I.14, in which E is —CH=CH— and the substituent Ar in each case corresponds to a line in Table D.
Table 153: Compounds of the general formula I.15, in which E is —$CH_2$—$CH_2$— and the substituent Ar in each case corresponds to a line in Table D.
Table 154 Compounds of the general formula I.15, in which E is —CH=CH— and the substituent Ar in each case corresponds to a line in Table D.

TABLE D

| Compound No. | Ar |
|---|---|
| D.1 | -Pyrazinyl |
| D.2 | -Pyrid-3'-yl |
| D.3 | -Pyrid-2'-yl |
| D.4 | -Pyrid-4'-yl |

TABLE D-continued

| Compound No. | Ar |
|---|---|
| D.5 | -Pyrimidin-2'-yl |
| D.6 | -Pyrimidin-4'-yl |
| D.7 | -Pyrimidin-5'-yl |
| D.8 | -Thiazol-2'-yl |
| D.9 | -Oxazol-2'-yl |
| D.10 | -Thien-2'-yl |
| D.11 | -Thien-3'-yl |
| D.12 | -Thiazol-2'-yl |
| D.13 | —CO—$C_6H_4$-3-$CF_3$ |
| D.14 | —CO—$C_6H_4$-4-F |
| D.15 | —CO—$C_6H_5$ |
| D.16 | —CO—$C_6H_4$-3-Cl |
| D.17 | —CO—$C_6H_4$-2-$CF_3$ |
| D.18 | —CO-Pyrid-3'-yl |
| D.19 | —CO—$C_6H_4$-4-Cl |
| D.20 | —CO—$C_6H_4$-4-$CH_3$ |
| D.21 | —CO—$C_6H_4$-4-$CF_3$ |
| D.22 | —CO—$C_6H_4$-3-$OCF_3$ |
| D.23 | —CO—$C_6H_4$-3-$OCH_3$ |
| D.24 | —CH(OH)—$C_6H_4$-3-$CF_3$ |
| D.25 | —CH(OH)—$C_6H_5$ |
| D.26 | —CH(OH)—$C_6H_4$-4-Cl |

TABLE 155

Compounds of the general formula

I.16

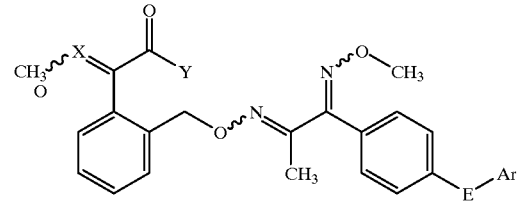

| Compound | X | Y | E-Ar | Physical data |
|---|---|---|---|---|
| 155.1 | CH | $OCH_3$ | —CH=CH-Pyrazinyl | 164–166 |
| 155.2 | CH | $OCH_3$ | —CH=CH-Pyrid-3-yl | Resin |
| 155.3 | CH | $OCH_3$ | —$(CH_2)_2$—$C_6H_3$-2,4-$Cl_2$ | 112–114 |
| 155.4 | CH | $OCH_3$ | —$(CH_2)_2$—$C_6H_5$ | Resin |
| 155.5 | CH | $OCH_3$ | —$(CH_2)_2$—$C_6H_4$-4-$OCH_3$ | 84–87 |
| 155.6 | CH | $OCH_3$ | —$(CH_2)_2$—$C_6H_3$-3,5-$CF_3$ | 99–101 |
| 155.7 | CH | $OCH_3$ | —$CH_2$—$CH_2$—$C_6H_4$-3-$CF_3$ | 174–177 |
| 155.8 | CH | $OCH_3$ | —$(CH_2)_2$-Pyrazinyl | 87–89 |
| 155.9 | CH | $OCH_3$ | —$(CH_2)_2$-Pyrid-3-yl | 88–90 |
| 155.10 | CH | $OCH_3$ | —$(CH_2)_2CH(OH)C_6H_3$-3-Cl | Resin |
| 155.11 | N | $OCH_3$ | —$(CH_2)_2$—$C_6H_4$-3-$CF_3$ | 99–101 |
| 155.12 | N | $OCH_3$ | —$(CH_2)_2$—$COC_6H_3$-3-$CF_3$ | 143–145 |
| 155.13 | N | $OCH_3$ | —$(CH_2)_2$—$COC_6H_3$-3-Cl | 128–130 |
| 155.14 | N | $OCH_3$ | —$(CH_2)_2$-Pyrazinyl | 101–103 |
| 155.15 | N | $OCH_3$ | —$(CH_2)_2$-Pyrid-3-yl | 98–100 |
| 155.16 | CH | $OCH_3$ | —$(CH_2)_2CH(OH)C_6H_3$-3-$CF_3$ | Resin |
| 155.17 | CH | $OCH_3$ | —CH=CH—$COC_6H_4$-3-Cl | |
| 155.18 | CH | $OCH_3$ | —$(CH_2)_2$—$COC_6H_4$-3-Cl | Resin |
| 155.19 | CH | $OCH_3$ | —$(CH_2)_2$-Thien-2-yl | 94–97 |
| 155.20 | CH | $OCH_3$ | —$(CH_2)_2$-Thien-3-yl | 75–78 |
| 155.21 | CH | $OCH_3$ | —$(CH_2)_2$—$C_6H_4$-3-$CH_3$ | 103–104 |
| 155.22 | CH | $OCH_3$ | —$(CH_2)_2$—$C_6H_4$-4-$CH_3$ | 77–80 |
| 155.23 | CH | $OCH_3$ | —$(CH_2)_2$-Pyrid-2-yl | 98–103 |
| 155.24 | CH | $OCH_3$ | —$(CH_2)_2$—$C_6H_4$-4-$OCOCH_3$ | 112–114 |
| 155.25 | CH | $OCH_3$ | —$(CH_2)_2$—$C_6H_4$-2-$CH_3$ | 86–88 |
| 155.26 | CH | $OCH_3$ | —$(CH_2)_2$-Pyrimidin-5-yl | |

TABLE 155-continued

Compounds of the general formula I.16

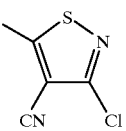

| Compound | X | Y | E-Ar | Physical data |
|---|---|---|---|---|
| 155.27 | CH | OCH$_3$ | —(CH$_2$)$_2$-(4-CN-3-Cl-isothiazol-5-yl) | |
| 155.28 | | | —(CH$_2$)$_2$—C$_6$H$_4$-4-COOCH$_3$ | 107–120 |
| 155.29 | | | —(CH$_2$)$_2$—C$_6$H$_4$-4-COOC$_2$H$_5$ | |
| 155.30 | | | —(CH$_2$)$_2$—C$_6$H$_3$-2,5-CH$_3$)$_2$ | |
| 155.31 | | | —(CH$_2$)$_2$—C$_6$H$_4$-4-NH$_2$ | |
| 155.32 | | | —(CH$_2$)$_2$—C$_6$H$_4$-3-NH$_2$ | |
| 155.33 | | | —(CH$_2$)$_2$—C$_6$H$_3$-3-Cl-4-OCOCH$_3$ | |
| 155.34 | | | —(CH$_2$)$_2$-naphtyl(1) | |
| 155.35 | | | —(CH$_2$)$_2$—C$_6$H$_4$-4-OH | |
| 155.36 | | | —(CH$_2$)$_2$-naphtyl(2) | |
| 155.37 | | | —(CH$_2$)$_2$-chinolinyl(3) | |
| 155.38 | | | —(CH$_2$)$_2$-pyrimidinyl(5) | 120–123 |

TABLE 156

Compounds of the general formula

| Compound | X | Y | Ar | R$_5$ | Physical data |
|---|---|---|---|---|---|
| 156.1 | CH | OCH$_3$ | —C$_6$H$_4$-4-Cl | 3-F | 88–90 |
| 156.2 | N | OCH$_3$ | —C$_6$H$_4$-4-Cl | 3-F | 91–93 |
| 156.3 | N | NHCH$_3$ | —C$_6$H$_4$-4-Cl | 3-F | 110–112 |
| 156.4 | CH | OCH$_3$ | —CH$_2$—C$_6$H$_4$-4-CF$_3$ | 2-F | 109–111 |
| 156.5 | N | OCH$_3$ | —CH$_2$—C$_6$H$_4$-4-CF$_3$ | 2-F | 108–109 |
| 156.6 | N | NHCH$_3$ | —CH$_2$—C$_6$H$_4$-4-CF$_3$ | 2-F | 149–151 |
| 156.7 | CH | OCH$_3$ | —CH$_2$—C$_6$H$_4$-4-F | 2-F | 94–96 |
| 156.8 | N | OCH$_3$ | —CH$_2$—C$_6$H$_4$-4-F | 2-F | 105–107 |
| 156.9 | N | NHCH$_3$ | —CH$_2$—C$_6$H$_4$-4-F | 2-F | 143–145 |
| 156.10 | N | OCH$_3$ | —C$_6$H$_4$-4-Cl | 2-OCH$_3$ | 89–91 |
| 156.11 | CH | OCH$_3$ | —C$_6$H$_4$-4-Cl | 2-OCH$_3$ | 100–102 |
| 156.12 | N | NHCH$_3$ | —C$_6$H$_4$-4-Cl | 2-OCH$_3$ | |

TABLE 157

Compounds of the general formula

| Compound | X | Y | Hal | AR$_7$ | Physical data |
|---|---|---|---|---|---|
| 157.1 | CH | OCH$_3$ | F | CH$_3$ | 112–114 |
| 157.2 | N | OCH$_3$ | F | CH$_3$ | 67–69 |
| 157.3 | N | NHCH$_3$ | F | CH$_3$ | 151–153 |
| 157.4 | CH | OCH$_3$ | Cl | CH$_3$ | 111–114 |
| 157.5 | N | OCH$_3$ | Cl | CH$_3$ | 101–104 |
| 157.6 | N | NHCH$_3$ | Cl | CH$_3$ | 149–151 |
| 157.7 | CH | OCH$_3$ | Br | CH$_3$ | 120–122 |
| 157.8 | N | OCH$_3$ | Br | CH$_3$ | 106–108 |
| 157.9 | N | NHCH$_3$ | Br | CH$_3$ | 135–137 |
| 157.10 | CH | OCH$_3$ | F | C$_2$H$_5$ | 87–91 |
| 157.11 | N | OCH$_3$ | F | C$_2$H$_5$ | 99–102 |
| 157.12 | N | NHCH$_3$ | F | C$_2$H$_5$ | 137–140 |
| 157.13 | CH | OCH$_3$ | Cl | C$_2$H$_5$ | 95–97 |

TABLE 157-continued

Compounds of the general formula

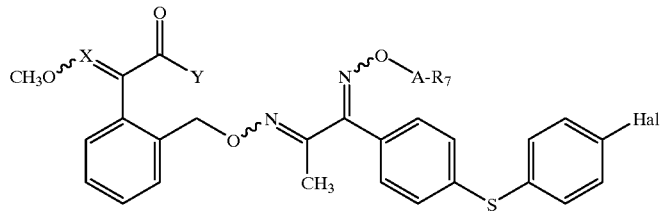

| Compound | X | Y | Hal | AR$_7$ | Physical data |
|---|---|---|---|---|---|
| 157.14 | N | OCH$_3$ | Cl | C$_2$H$_5$ | 112–114 |
| 157.15 | N | NHCH$_3$ | Cl | C$_2$H$_5$ | 153–155 |
| 157.16 | CH | OCH$_3$ | Br | C$_2$H$_5$ | 96–99 |
| 157.17 | N | OCH$_3$ | Br | C$_2$H$_5$ | 107–110 |
| 157.18 | N | NHCH$_3$ | Br | C$_2$H$_5$ | 147–150 |

TABLE 158

Compounds of the general formula

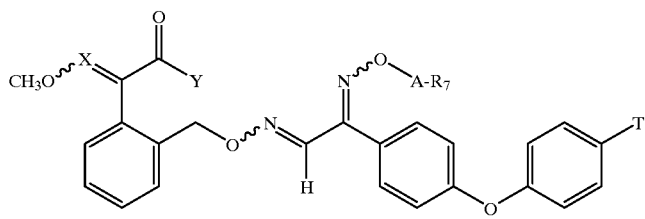

| Compound | X | Y | T | AR$_7$ | Physical data |
|---|---|---|---|---|---|
| 158.1 | CH | OCH$_3$ | 4-Br | C$_2$H$_5$ | n$_D^{22}$: 1.595 |
| 158.2 | N | OCH$_3$ | 4-Br | C$_2$H$_5$ | resin |
| 158.3 | N | NHCH$_3$ | 4-Br | C$_2$H$_5$ | resin |
| 158.4 | CH | OCH$_3$ | 4-Br | CH$_3$ | resin |
| 158.5 | N | OCH$_3$ | 4-Br | CH$_3$ | resin |
| 158.6 | N | NHCH$_3$ | 4-Br | CH$_3$ | resin |
| 158.7 | CH | OCH$_3$ | 4-O—CH$_3$ | C$_2$H$_5$ | |
| 158.8 | N | OCH$_3$ | 4-O—CH$_3$ | C$_2$H$_5$ | resin |
| 158.9 | N | NHCH$_3$ | 4-O—CH$_3$ | C$_2$H$_5$ | |
| 158.10 | CH | OCH$_3$ | 4-t-Butyl | C$_2$H$_5$ | |
| 158.11 | N | OCH$_3$ | 4-t-Butyl | C$_2$H$_5$ | |
| 158.12 | N | NHCH$_3$ | 4-t-Butyl | C$_2$H$_5$ | |
| 158.13 | CH | OCH$_3$ | 4-CF$_3$ | C$_2$H$_5$ | |
| 158.14 | N | OCH$_3$ | 4-CF$_3$ | C$_2$H$_5$ | |
| 158.15 | N | NHCH$_3$ | 4-CF$_3$ | C$_2$H$_5$ | |

Formulation Examples (% = per cent by weight)

| Example F1: Emulsion concentrates | a) | b) | c) |
|---|---|---|---|
| Active compound | 25% | 40% | 50% |
| Calcium dodecylbenzenesulfonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing the finely ground active compound and additives results in an emulsion concentrate which gives emulsions of the desired concentration by dilution with water.

Formulation Examples (% = per cent by weight)

| Example F2: Solutions | a) | b) | c | d) |
|---|---|---|---|---|
| Active compound | 80% | 10% | 5% | 95% |
| Ethylene glycol monomethyl ether | 20% | — | — | — |
| Polyethylene glycol (MW 400) | — | 70% | — | — |
| N-Methylpyrrolid-2-one | — | 20% | — | — |
| Epoxidized coconut oil | — | — | 1% | 5% |
| Benzine (boiling limits: 160–190) | — | — | 94% | — |

Mixing of the finely ground active compound and the additives results in a solution which is suitable for application in the form of tiny drops.

| Example F3: Granules | a) | b) | c) | d) |
|---|---|---|---|---|
| Active compound | 5% | 10% | 8% | 21% |
| Kaolin | 94% | — | 79% | 54% |

| Formulation Examples (% = per cent by weight) | | | |
|---|---|---|---|
| Highly disperse silicic acid | 1% | — 13% | 7% |
| Attapulgite | — | 90% — | 18% |
| The active compound is dissolved in methylene chloride, the solution is sprayed onto the carrier mixture and the solvent is evaporated off in vacuo. | | | |

| Example F4: Dusts | a) | b) |
|---|---|---|
| Active compound | 2% | 5% |
| Highly disperse silicic acid | 1% | 5% |
| Talc | 97% | — |
| Kaolin | — | 90% |
| Mixing of the active compound and carriers results in ready-to-use dusts. | | |

| Example F5: Wettable powders | a) | b) | c) |
|---|---|---|---|
| Active compound | 25% | 50% | 75% |
| Sodium lignin-sulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7–8 mol of EO) | — | 2% | — |
| Highly disperse silicic acid | 5% | 10% | 10% |
| Kaolin | 62% | 27% | — |
| The active compound and additives are mixed and the mixture is ground in a suitable mill. Wettable powders which can be diluted with water to give suspensions of the desired concentration are obtained. | | | |

| Example F6: Emulsion concentrate | |
|---|---|
| Active compound | 10% |
| Octylphenol polyethylene glycol ether (4–5 mol of EO) | 3% |
| Calcium dodecylbenzenesulfonate | 3% |
| Castor oil polyethylene glycol ether (36 mol of EO) | 4% |
| Cyclohexanone | 30% |
| Xylene mixture | 50% |
| Mixing of the finely ground active compound and the additives results in an emulsion concentrate which gives emulsions of the desired concentration by dilution with water. | |

| Example F7: Dusts | a) | b) |
|---|---|---|
| Active compound | 5% | 8% |
| Talc | 95% | — |
| Kaolin | — | 92% |
| Ready-to-use dusts are obtained by mixing the active compound and carrier and grinding the mixture in a suitable mill. | | |

| Example F8: Extruded granules | |
|---|---|
| Active compound | 10% |
| Sodium lignin-sulfonate | 2% |
| Carboxymethylcellulose | 1% |
| Kaolin | 87% |
| The active compound and additives are mixed, the mixture is ground, moistened with water, extruded and granulated and the granules are dried in a stream of air. | |

| Example F9: Coated granules | |
|---|---|
| Active compound | 3% |
| Polyethylene glycol (MW 200) | 3% |
| Kaolin | 94% |
| Uniform application of the finely ground active compound to the kaolin moistened with polyethylene glycol in a mixer results in dust-free coated granules. | |

| Example F10: Suspension concentrate | |
|---|---|
| Active compound | 40% |
| Ethylene glycol | 10% |
| Nonylphenol polyethylene glycol ether (15 mol of EO) | 6% |
| Sodium ligninsulfonate | 10% |
| Carboxymethylcellulose | 1% |
| Aqueous formaldehyde solution (37%) | 0.2% |

| Formulation Examples (% = per cent by weight) | |
|---|---|
| Aqueous silicone oil emulsion (75%) | 0.8% |
| Water | 32% |
| Mixing of the finely ground active compound and the additives results in a suspension concentrate which gives suspensions of the desired concentration by dilution with water. | |

Biological Examples
A) Microbicidal Action

Example B1: Action Against *Phytophthora infestans* on Tomatoes a) Curative Action After being grown for three weeks, tomato plants of the "Roter Gnom" variety are sprayed with a zoospore suspension of the fungus and incubated in a booth at 18 to 20° and saturated atmospheric humidity. Interruption of the humidification after 24 hours. After the plants have dried off, they are sprayed with a liquor which comprises the active substance, formulated as a wettable powder, in a concentration of 200 ppm. After the spray coating has dried on, the plants are placed in the humidity booth again for 4 days. The number and size of the typical leaf spots which have occurred after this time are the standard for evaluation of the activity of the substances tested.

b) Preventive Systemic Action

The active substance, formulated as a wettable powder, is introduced in a concentration of 60 ppm (based on the soil volume) onto the soil surface of potted tomato plants of the "Roter Gnom" variety three weeks old. After a waiting time of three days, the underside of the leaves of the plants is sprayed with a zoospore suspension of *Phytophthora infestans*. The plants are then kept In a spray booth at 18 to 20° C. and saturated atmospheric humidity for 5 days. After this time, typical leaf spots form, the number and size of which are used to evaluate the activity of the substances tested.

While untreated but infected control plants show an infestation of 100%, in both tests the infestation is suppressed to 20% or less with the active compounds of Tables 1 to 118. In particular, the infestation is even completely suppressed at a concentration of 20 ppm of the active substance with the compounds 1.3, 1.4, 1.13, 1.19, 1.20, 1.30, 1.31, 1.33, 1.48 to 1.57, 1.62 to 1.72, 1.75A, 1.78 to 1.80, 2.21 to 2.25, 2.27, 2.32, 2.35 to 2.52, 2.55, 2.58, 2.59 to 3.26, 3.33 to 3.39, 3.43 to 3.54, 3.56, 3.60, 4.3, 4.57 and 4.60.

Example B2: Action Against *Plasmopara viticola* (Bert. etCurt.) (Berl. et DeToni) on Vines a) Residual Preventive Action Vine cuttings of the "Chasselas" variety are grown on in a greenhouse. At the 10-leaf stage, 3 plants are sprayed with a liquor (200 ppm of active compound). After the spray coating has dried on, the plants are infected uniformly with the spore suspension of the fungus on the underside of the leaves. The plants are then kept in a humidity chamber for 8 days. After this time, clear symptoms of disease are found on the control plants. The number and size of the infection sites on the treated plants are used as a standard for evaluating the activity of the substances tested.

b) Curative Action

Vine cuttings of the "Chasselas" variety are grown on in a greenhouse and, at the 10-leaf stage, are infected with a spore suspension of *Plasmopara viticola* on the underside of the leaves. After remaining in a humidity chamber for 24 hours, the plants are sprayed with an active compound liquor (200 ppm, 60 ppm, 20 ppm of active compound). The plants are then kept in the humidity booth for a further 7 days. After this time, symptoms of disease are found on the control plants. The number and size of the infection sites on the plants treated are used as a standard for evaluating the activity of the substances tested.

Compared with the control plant, the plants treated with active compounds of Tables 1 to 118 show an infestation of 20% or less. In particular, even at a concentration of 20 ppm of the active substance, a complete curative action is still achieved with the compounds 1.3, 1.4, 1.13, 1.29, 1.30, 1.31, 1.33, 1.52, 1.63B, 1.71A, 1.71B, 1.73A, 1.73B, 1.78, 221, 2.22, 2.25, 2.27, 2.33, 2.45, 2.49, 2.55, 2.58, 3.21, 3.43, 3.46, 3.56, 4.3, 4.57, 4.58, 4.60 and 4.65.

Example B3: Action Against *Pythium debaryanum* on sugar beet (*Beta vulgaris*)

a) Action after Soil Application

The fungus is cultured on sterile oat grains and added to an earth-sand mixture. The earth thus infected is introduced into flower pots and sown with sugar beet seeds. Directly after sowing, the test preparations, formulated as wettable powders, are poured over the earth as an aqueous suspension (20 ppm of active compound, based on the volume of earth). The pots are then placed in a greenhouse at 20–24° C. for 2–3 weeks. The earth is constantly kept uniformly moist by gentle spraying with water. In the evaluation of the tests, the emergence of the sugar beet plants and the proportion of healthy and sick plants are determined.

b) Action after Dressing Application

The fungus is cultured on sterile oat grains and added to an earth-sand mixture. The earth thus infected is introduced into flower pots and sown with sugar beet seeds which have been dressed with the test preparations, formulated as dressing powders (1000 ppm of active compound, based on the seed weight). The sown pots are placed in a greenhouse at 20–24° C. for 2–3 weeks. During this period, the soil is kept uniformly moist by gentle spraying with water.

In the evaluation, the emergence of the sugar beet plants and the proportion of healthy and sick plants is determined.

After the treatment with active compounds of Tables 1 to 118, more than 80% of the plants emerge and have a healthy appearance. In the control pots, only isolated emerged plants with a sickly appearance are observed.

Example B4: Residual Protective Action Against *Cercospora arachidicola* on Groundnuts Groundnut plants 10 to 15 cm high are sprayed with an aqueous spray liquor (0.02% of active substance) until dripping wet, and 48 hours later are infected with a conidia suspension of the fungus. The plants are incubated at 21° C. and high atmospheric humidity for 72 hours and then placed in a greenhouse until the typical leaf spots occur. The action of the active substance is evaluated 12 days after infection on the basis of the number and size of the leaf spots.

The active compounds of Tables 1 to 118 cause a reduction in the leaf spots to less than about 10% of the leaf surface. In particular, the diseases is suppressed completely (0–5% infestation) with compounds 1.49 to 1.72, 1.79, 2.20 to 2.24, 2.35 to 2.39, 2.44 to 2.52, 2.59, 3.22 to 3.24, 3.34 to 3.39, 3.45 to 3.60 and 3.62.

Example B5: Action Against *Puccinia graminis* on Wheat a) Residual Protective Action 6 Days after sowing, wheat plants are sprayed with an aqueous spray liquor (0.02% of active substance) until dripping wet, and 24 hours later are infected with a uredo spore suspension of the fungus. After an incubation time of 48 hours (conditions: 95 to 100% relative atmospheric humidity at 20° C.), the plants are placed in a greenhouse at 22° C. The development of rust pustules is evaluated 12 days after infection.

b) Systemic Action

5 Days after sowing, wheat plants are watered with an aqueous spray liquor (0.006% of active substance, based on the soil volume). It is ensured here that the spray liquor does not come into contact with the above-ground parts of the plants. 48 hours later, the plants are infected with a uredo spore suspension of the fungus. After an incubation time of 48 hours (conditions: 95 to 100 per cent relative atmospheric humidity at 20° C.), the plants are placed in a greenhouse at 22° C. The development of rust pustules is evaluated 12 days after infection.

The compounds of Tables 1 to 118 cause a significant reduction in the fungus infestation, sometimes to 10–0%. In particular, the disease is suppressed completely (0–5% infestation) with compounds 1.51, 1.57, 1.62 to 1.64, 1.79, 2.22, 2.23, 2.35, 2.39, 2.44, 2.45, 2.49, 2.52, 2.59, 3.22 to 3.24, 3.35, 3.39, 3.45 to 3.67, 3.50, 3.53 and 3.60.

Example B6: Action Against *Pyricularia oryzae* on Rice a) Residual Protective Action After being grown for two weeks, rice plants are sprayed with an aqueous spray liquor (0.02% of active substance) until dripping wet, and 48 hours later are infected with a conidia suspension of the fungus. The fungus infestation is evaluated 5 days after infection, during which 95 to 100% relative atmospheric humidity and a temperature of 22° C. are maintained.

b) Systemic Action

Rice plants 2 weeks old are watered with an aqueous spray liquor (0.006% of active substance, based on the soil volume). It is ensured here that the spray liquor does not come into contact with above-ground parts of the plants. The pots are then filled with water such that the lowest parts of the stems of the rice plants are standing in the water. After 96 hours, the plants are infected with a conidia suspension of the fungus and kept at 95 to 100% relative atmospheric humidity and a temperature of 24° C. for 5 days.

The compounds of Tables 1 to 118 for the most part prevent the outbreak of the disease on the infected plants. In particular, the disease is suppressed completely (0–5% infestation) with the compounds 1.51, 1.57, 1.62 to 1.64, 1.79, 2.22, 2.23, 2.35, 2.39, 2.44, 2.45, 2.49, 2.52, 2.59, 3.22 to 3.24, 3.35, 3.39, 3.45 to 3.67, 3.50, 3.53 and 3.60.

Example B7: Residual Protective Action Against *Venturia inaequalis* on Apples Apple seedlings with fresh shoots 10 to 20 cm long are sprayed with a spray liquor (0.02% of active substance) until dripping wet, and 24 hours later are infected with a conidia suspension of the fungus. The plants are incubated at 90 to 100% relative atmospheric humidity for 5 days and placed in a greenhouse at 20° to 24° C. for a further 10 days. The scab infestation is evaluated 15 days after infection.

The compounds of Tables 1 to 118 predominantly display a lasting action against scab diseases.

Example B8: Action Against *Erysiphe Graminis* on Barley a) Residual Protective Action Barley plants approximately 8 cm high are sprayed with an aqueous spray liquor (0.02% of active substance) until dripping wet, and 3 to 4 hours later are dusted with conidia of the fungus. The infected plants are placed in a greenhouse at 22° C. The fungus infestation is evaluated 10 days after infection.

b) Systemic Action

Barley plants approximately 8 cm high are watered with an aqueous spray liquor (0.002% of active substance, based on the soil volume). It is ensured here that the spray liquor does not come into contact with the above-ground parts of the plants. 48 hours later, the plants are dusted with conidia of the fungus. The infected plants are placed in a greenhouse at 22° C. The fungus infestation is evaluated 10 days after infection.

The compounds of Tables 1 to 118 are capable generally of suppressing the disease infestation to less than 20%, and in some cases even completely.

Example B9: Action Against *Podosphaera leucotricha* on Apple Shoots

Residual Protective Action

Apple seedlings with fresh shoots about 15 cm long are sprayed with a spray liquor (0.06% of active substance). After 24 hours, the treated plants are infected with a conidia suspension of the fungus and placed in a climatically controlled chamber at 70% relative atmospheric humidity and 20° C. The fungus infestation is evaluated 12 days after infection.

The disease infestation is prevented to below 20% with active compounds of Tables 1 to 118. Control plants are infested to the extent of 100%.

Example B10: Action Against *Botrytis cinerea* on Apple Fruit. Residual Protective Action Artificially damaged apples are treated by dripping a spray liquor (0.02% of active substance) onto the damaged areas. The treated fruits are then inoculated with a spore suspension of the fungus and incubated at high atmospheric humidity and about 20° C. for 1 week. The fungicidal action of the test substance is deduced from the number of damaged areas which have started to rot.

Active compounds of Tables 1 to 118 are capable of preventing the spread of the rot, in some cases completely.

Example B11: Action Against *Helminthosporium gramineum*

Wheat grains are contaminated with a spore suspension of the fungus and left to dry. The contaminated grains are dressed with a suspension of the test substance (600 ppm of active compound, based on the weight of the seed). After 2 days, the grains are laid out on suitable agar dishes, and after a further 4 days the development of the fungus colonies around the grains is evaluated. The number and size of the fungus colonies are used to evaluate the test substance.

Compounds of Tables 1 to 118 in some cases show a good action, i.e. inhibition of the fungus colonies. In particular, the disease is suppressed completely (0–5% infestation) with compounds 1.51, 1.62 to 1.64, 2.22, 2.23, 2.39, 2.44, 2.49, 2.52, 3.22 to 3.24, 3.35, 3.45 to 3.67, 3.53 and 3.60.

Example B12: Action Against *Colletotrichum lagenarium* on Cucumbers

After being grown for 2 weeks, cucumber plants are sprayed with a spray liquor (concentration 0.002%). After 2 days, the plants are infected with a spore suspension (1.5× $10^5$ spores/ml) of the fungus and incubated at 23° C. and high atmospheric humidity for 36 hours. The incubation is then continued under normal atmospheric humidity at about 22–23° C. The fungus infestation which has occurred is evaluated 8 days after infection. Untreated but infected control plants show a fungus infestation of 100%.

The compounds of Tables 1 to 118 cause in some cases an almost complete inhibition of the disease infestation.

Example B13: Action Against *Fusarium nivale* on Rye

Rye of the Tetrahell variety naturally infected with *Fusarium nivale* is dressed on a mixing roll with the fungicide to be tested, the following concentrations being applied: 20 or 6 ppm of active substance (based on the weight of the seed).

The infected and treated rye is sown in October in the open with a sowing machine on plots of 3 m length and 6 seed rows, 3 repeats per concentration.

Until the infestation is evaluated, the test crop is cultured under normal field conditions (preferably in a region with blanket snow cover during the winter months).

To evaluate the phytotoxicity, the seed emergence is rated in Autumn and the crop densities/stocking is rated in Spring.

To determine the activity of the active compound, the percentage proportion of Fusarium-infested plants is counted in the Spring, immediately after melting of the snow. The number of infested plants was less than 5% in the present case. The plants which had emerged had a healthy appearance. In particular, the disease is suppressed completely (0–5% infestation) with compounds 1.57, 1.62 to 1.64, 1.79, 2.23, 2.35, 2.39, 2.44, 2.49, 2.52, 2.59, 3.22 to 3.24, 3.39, 3.45 to 3.67, 3.53 and 3.60.

Example B14: Action Against *Septoria nodorum* on Wheat

Wheat plants are sprayed in the 3-leaf stage with a spray liquor (60 ppm of active substance) prepared from a wettable powder of the active substances (2.8:1).

After 24 hours, the treated plants are infected with a conidia suspension of the fungus. The plants are then incubated at 90–100% relative atmospheric humidity for 2 days and placed in a greenhouse at 20–24° C. for a further 10 days. 13 days after infection, the fungus infestation is evaluated. Less than 1% of the wheat plants show an infestation.

Example B15: Action Against *Rhizoctonia solani* on Rice

Protective Local Soil Application

Rice plants 10 days old are watered thoroughly with a suspension (spray liquor) prepared from the formulated test substance, without contaminating the above-ground parts of the plants. The plants are infected three days later by placing a barley straw infected with Rhizoctonia solani between the rice plants in each pot. After incubation in a climatically controlled chamber at a daytime temperature of 29° C. and night time temperature of 26° C. and 95% relative atmospheric humidity for 6 days, the fungus infestation is evaluated. Less than 5% of the rice plants showed an infestation. The plants had a healthy appearance.

Protective Local Leaf Application

Rice plants 12 days old are sprayed with a suspension prepared from the formulated test substances. The plants are infected one day later by placing a barley straw infected with *Rhizoctonia solani* between the rice plants in each pot. After incubation in a climatically controlled chamber at a daytime temperature of 29° C. and night time temperature of 26° C. and 95% relative atmospheric humidity for 6 days, the test plants are rated. Untreated but infected control plants show a fungus infestation of 100%. The compounds of Tables 1 to 118 in some cases cause complete inhibition of the disease infestation.

B. Insecticidal Action

Example B16: Action Against *Aphis craccivora*

Pea seedlings are infected with *Aphis craccivora*, subsequently sprayed with a spray liquor comprising 100 ppm of active compound and then incubated at 20° C. 3 and 6 days later, the percentage reduction in population (% action) is determined by comparing the number of dead aphids on the treated and untreated plants.

The compounds of Tables 1 to 118 in most cases show a good action in this test. In particular, compounds 1.9, 4.5, 4.16, 4.17, 4.20, 4.25 to 4.32, 4.47 and 4.141 to 4.146 show an action of more than 80% in this test

Example B17: Action Against *Diabrotica balteata*

Maize seedlings are sprayed with an aqueous emulsion spray liquor comprising 100 ppm of active compound and, after the spray coating has dried on, are populated with 10 larvae of the second stage of *Diabrotica balteata* and then placed in a plastic container. 6 days later, the percentage reduction in population (% action) is determined by comparing the number of dead larvae between the treated and untreated plants.

The compounds of Tables 1 to 118 show a good action in this test. In particular, compounds 1.9, 2.31, 4.4, 4.5 4.6, 4.16, 4.17, 4.20, 4.25, 4.34, 4.39, 4.40 to 4.47, 4.141, 4.144 and 4.146 show an action of more than 80% in this test.

Example B18: Action Against *Heliothis virescens*

Young soya plants are sprayed with an aqueous emulsion spray liquor comprising 100 ppm of active compound and, after the spray coating has dried on, are populated with 10 caterpillars of the first stage of *Heliothis virescens* and then placed in a plastic container. 6 days later, the percentage reduction in population and the feeding damage (% action) are determined by comparing the number of dead caterpillars and the feeding damage between the treated and untreated plants.

Most of the compounds of Tables 1 to 118 show a good action in this test. In particular, compounds 1.9, 2.31, 4.5, 4.20, 4.29, 4.33, 4.39, 4.40 to 4.47, 4.141, 4.144 and 4.146 show an action of more than 80% in this test.

Example B19: Action Against *Spodoptera littoralis*

Young soya plans are sprayed with an aqueous emulsion spray liquor comprising 100 ppm of active compound and, after the spray coating has dried on, are populated with 10 caterpillars of the third stage of *Spodoptera littoralis* and then placed in a plastic container. 3 days later, the percentage reduction in population and the percentage reduction in feeding damage (% action) are determined by comparing the number of dead caterpillars and the feeding damage between the treated and untreated plants.

The compounds of Tables 1 to 118 show a good action in this test. In particular, compounds 1.9, 4.5, 4.16, 4.17, 4.20, 4.25 to 4.32, 4.47 and 4.141 to 4.146 show an action of more than 80% in this test.

C. Acaricidal action

Example B20: Action Against *Tetranychus urticae*

Young bean plants are populated with a mixed population of *Tetranychus urticae*, and 1 day later are sprayed with an aqueous emulsion spray liquor comprising 100 ppm of active compound, incubated at 25° C. for 6 days and then evaluated. The percentage reduction in population (% action) is determined by comparing the number of dead eggs, larvae and adults on the treated and untreated plants.

The compounds of Tables 1 to 118 in most cases show a good action in this test. In particular, compounds 1.9, 2.31, 4.5, 4.20, 4.29, 4.33, 4.39, 4.40 to 4.46 and 4.141 to 4.146 show an action of more than 80% In this test.

What is claimed is:

1. A compound of the formula $$R_9O\diagdown X \diagup Z \diagdown Y \diagdown O \diagdown N \diagup O \diagdown A \diagdown R_7$$

(with $R_3$, $R_4$ on left aryl ring and $R_2$, $(GR)_n$, $(R_5)_q$ on right aryl ring) (I)

in which either

Y is $OR_1$ and

Z is O; or

Y is $NHR_8$ and

Z is O, S or S(=O); and in which either

A is a direct bond, $C_1$–$C_{10}$alkylene, —C(=O)—, —C(=S)— or halogeno-$C_1$–$C_{10}$alkylene and $R_7$ is a radical $R_{10}$; or A is $C_1$–$C_{10}$alkylene, —C(=O)—, —C(=S)— or halogeno-$C_1$–$C_{10}$alkylene and $R_7$ is —CN, $OR_{10}$, $N(R_{10})_2$, where the radicals $R_{10}$ can be identical or different, or —S(=O)$_p R_{10}$; and in which G is O;

R is a substituted aryl- or benzyl-group, where the substituents are selected from the group consisting of halogen, $C_1$–$C_4$alkyl, halogeno-$C_1$–$C_4$alkyl, $C_3$–$C_6$cycloalkyl and halogeno-$C_3$–$C_8$cycloalkyl; or $CH_2Si(CH_3)_3$;

n is 1;

$R_1$ is $C_1$–$C_4$alkyl;

$R_2$ is H, $C_1$–$C_4$alkyl, halogeno-$C_1$–$C_4$alkyl, $C_3$–$C_6$cycloalkyl, $C_1$–$C_4$alkoxymethyl, $C_1$–$C_4$alkoxy, halogeno-$C_1$–$C_4$alkoxy, $C_1$–$C_4$alkylthio, halogeno-$C_1$–$C_4$alkylthio or CN;

$R_3$ and $R_4$ independently of one another are H, $C_1$–$C_4$alkyl, $C_1$–$C_4$alkoxy, OH, CN, $NO_2$, a $(C_1$–$C_4$alkyl)$_3$-Si group, where the alkyl groups can be identical or different, halogen, $(C_1$–$C_4$alkyl)$S(=O)_m$, (halogeno-$C_1$–$C_4$alkyl)$S(=O)_m$, halogeno-$C_1$–$C_4$alkyl or halogeno-$C_1$–$C_4$alkoxy;

m is 0, 1 or 2;

$R_8$ is H or $C_1$–$C_4$alkyl;

$R_9$ is methyl, fluoromethyl or difluoromethyl;

$R_{10}$ is H, $C_1$–$C_6$alkyl, $C_2$–$C_8$alkenyl, $C_2$–$C_8$alkynyl, $C_3$–$C_6$cycloalkyl; or $C_1$–$C_6$alkyl, $C_2$–$C_8$alkenyl, $C_2$–$C_8$alkynyl or $C_3$–$C_6$cycloalkyl-, which are mono- or polysubstituted by substituents from the group consisting of halogen; —Si($C_1$–$C_4$alkyl)$_3$, where the alkyl groups can be identical or different; $C_1$–$C_6$alkoxycarbonyl, or an aryl or heterocyclyl group which are unsubstituted or mono- or polysubstituted by substituents from the group consisting of halogen, $C_1$–$C_4$alkyl and halogeno-$C_1$–$C_4$alkyl; and with the proviso that R is not phenyl which is substituted by fluorine or chlorine in the 4-position or benzyl which is substituted by methyl or methoxy in the 4-position or monosubstituted by fluorine, chlorine, bromine or $CF_3$ in the 2-, 3- or 4-position if OR is in the p-position, $AR_7$ is $CH_3$, $R_2$ is $CH_3$ and $R_3$ and $R_4$ are H.

2. A compound according to claim 1 of the formula (I), in which Y is $OR_1$.

3. A compound according to claim 1 of the formula (I), In which Z is O.

4. A compound according to claim 2 of the formula (I), in which $R_1$ is $C_1$–$C_2$alkyl.

5. A compound according to claim 1 of the formula (I), in which $R_2$ is H, $C_1$–$C_4$alkyl, halogeno-$C_1$–$C_4$alkyl or $C_3$–$C_6$cycloalkyl.

6. A compound according to claim 1 of the formula (I), in which $R_3$ and $R_4$ independently of one another are H, $C_1$–$C_4$alkyl, $C_1$–$C_4$alkoxy, OH, CN, $NO_2$, halogen, halogeno-$C_1$–$C_4$alkyl or halogeno-$C_1$–$C_4$-alkoxy.

7. A compound according to claim 1 of the formula (I), in which $R_8$ is H or $C_1$–$C_2$alkyl.

8. A compound according to claim 1 of the formula (I), in which $R_9$ is methyl or fluoromethyl.

9. A compound according to claim 1 of the formula (I), in which m is 0 or 2.

10. A compound according to claim 1 of the formula (I), in which $AR_7$ is methyl or ethyl.

11. A compound according to claim 1 of the formula (I), in which A—$R_7$ is $C_2H_5$.

12. A process for the preparation of a compound according to claim 1 of the formula (I) or, where appropriate, one of its E/Z isomers or tautomers, in each case in the free form or in salt form, which comprises, for example, a1) either reacting a compound of the formula

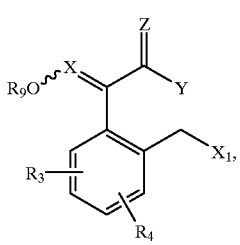

(II)

in which

X, Y, Z, $R_3$, $R_4$ and $R_9$ are as defined for formula (I) and $X_1$ is a leaving group, and in which the provisos mentioned in claim 1 for the compound of the formula (I) apply, preferably in the presence of a base, with a compound of the formula

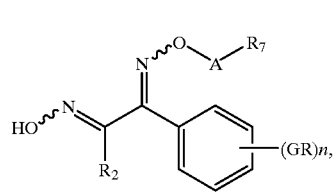

(III)

in which n, A, G, R, $R_2$, and $R_7$ are as defined for formula (I), and in which the provisos mentioned in claim 1 for the compound of the formula (I) apply, or a2) reacting a compound of the formula

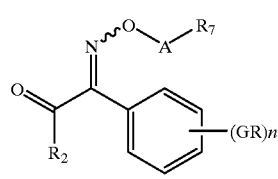

(IV)

in which n, R, A, G, $R_2$, and $R_7$ are as defined for formula (I), and in which the provisos mentioned in claim 1 for the compound of the formula (I) apply, if appropriate in the presence of a base, with a compound of the formula

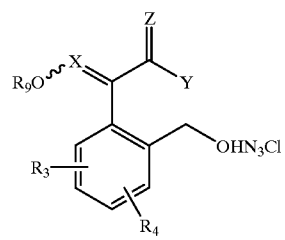

(V)

which is known or can be prepared by methods known per se, and in which X, Y, Z, $R_3$, $R_4$ and $R_9$ are as defined for formula (I), or b) for the preparation of a compound of the formula (I) in which Y is $NHR_8$ and Z is O, reacting a compound of the formula (I) in which Y is $OR_1$ with a compound of the formula $R_8NH_2$, which is known or can be prepared by methods known per se and in which $R_8$ is as defined for formula (I), or c) for the preparation of a compound of the formula (I) in which Y is $NHR_8$ and Z is S, reacting a compound of the formula (I) in which Y is $R_8NH_2$ and Z is O with $P_4S_{10}$ or Lawesson's reagent, or d) for the preparation of a compound of the formula (I) in which Z is SO, reacting a compound of the formula (I) in which Z is S with an oxidizing agent, or reacting a compound of the formula

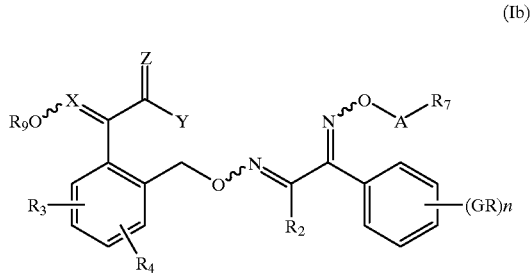
(Ib)

in which
X, Y, Z, R$_3$, R$_4$, R$_9$ n, R, A, G, R$_2$ and R$_7$ are as defined for formula (I);

in which the provisos mentioned in claim 1 for the compound of the formula (I) apply; and which is known or can be prepared by processes known per se, with hydrogen in the presence of a hydrogenation catalyst, and in each case, if desired, converting a compound of the formula (I) obtainable according to the process or in another manner or an E/Z isomer or tautomer thereof, in each case in the free form or in salt form, into another compound of the formula (I) or an E/Z isomer or tautomer thereof, in each case in the free form or in salt form, separating a mixture of E/Z isomers obtainable according to the process and isolating the desired isomer, and/or converting a free compound of the formula (I) obtainable according to the process or in another manner or an E/Z isomer or tautomer thereof into a salt or converting a salt, obtainable according to the process or in another manner, of a compound of the formula (I) or of an or E/Z isomer or tautomer thereof into the free compound of the formula (I) or an E/Z isomer or tautomer thereof or into another salt.

13. A compound of the formula

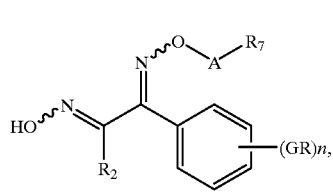
(III)

in which n, A, G, R, R$_2$, and R$_7$ are as defined for formula (I) in claim 1 and in which the provisos mentioned in claim 1 for the compounds of the formula (I) apply, or, where appropriate, a possible E/Z isomer, E/Z isomer mixture and/or tautomer thereof, in the free form or in salt form.

14. A process for the preparation of a compound as defined in claim 13 of the formula (III), in each case in the free form or in salt form, which comprises, for example, f) reacting a compound of type formula (IV) in which n, A, G, R, R$_2$, and R$_7$ are as defined for formula (I) in claim 1 and in which the provisos mentioned in claim 1 for the compound of the formula (I) apply, if appropriate in the presence of a base, with H$_2$NOH or a salt thereof, or g) reacting a compound of the formula

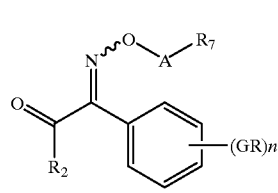
(IV)

in which n, G, R, and R$_2$ are as defined for formula (I) in claim 1 and in which the provisos mentioned in claim 1 for the compound of the formula (I) apply, if appropriate in the presence of a base, with a compound of the formula

R$_7$ANH$_2$ (VII), which is known or can be prepared by methods known per se and in which A and R$_7$ are as defined for formula (I) in claim 1, and in each case, if desired, converting a compound of the formula (III) obtainable according to the process or in another manner or an E/Z isomer or tautomer thereof, in each case in the free form or in salt form, into another compound of the formula (III) or an E/Z isomer or tautomer thereof, in each case in the free form or in salt form, separating a mixture of E/Z isomers obtainable according to the process and isolating the desired isomers, and/or converting a free compound of the formula (III) obtainable according to the process or in another manner or an E/Z isomer or tautomer thereof into a salt, or converting a salt, obtainable according to the process or in another manner, of a compound of the formula (III) or of an E/Z isomer or tautomer thereof into the free compound of the formula (III) or an E/Z isomer or tautomer thereof or into another salt.

15. A pesticide, which comprises at least one compound according to claim 1 of the formula (I) or, where appropriate, an E/Z isomer or tautomer thereof, in the free form or in an agro-chemically usable salt form, as the active compound in an effective action concentration and at least one auxiliary.

16. A process for the preparation of a composition as defined in claim 14, which comprises intimately mixing and/or grinding the active compound with the auxiliary or auxiliaries.

17. A method of controlling pests, which comprises applying a compound of the formula (I) or a composition as defined in claim 15 to the pests or their environment.

18. A process according to claim 17 for protecting plant propagation material, which comprises treating the propagation material or the site of planting out of the propagation material.

19. Plant propagation material treated by the process defined in claim 18.

20. A compound of the formula

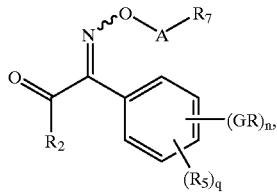
(IV)

in which n, q, R, A, G, $R_2$, $R_5$ and $R_7$ are as defined for formula (I), claim 1, and in which the provisos mentioned in claim 1 for the compound of the formula (I) apply, or, where appropriate, a possible E/Z isomer, E/Z isomer mixture and/or tautomer thereof, in the free form or in salt form.

21. A compound of the formula

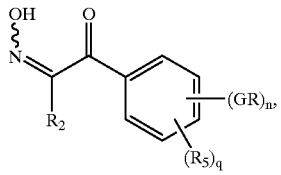
(VI)

in which n, q, G, R, $R_2$ and $R_5$ are as defined for formula (I), claim 1, and in which the provisos mentioned in claim 1 for the compound of the formula (I) apply, or, where appropriate, a possible E/Z isomer, E/Z isomer mixture and/or tautomer thereof, in the free form or in salt form.

22. A compound according to claim 2 of the formula (I), in which $R_2$ is H, $C_1$–$C_4$alkyl, halogeno-$C_1$–$C_4$alkyl or $C_3$–$C_6$cycloalkyl.

23. A compound according to claim 2 of the formula (I), in which $R_3$ and $R_4$ independently of one another are H, $C_1$–$C_4$alkyl, $C_1$–$C_4$alkoxy, OH, CN, $NO_2$, halogen, halogeno-$C_1$–$C_4$alkyl or halogeno-$C_1$–$C_4$-alkoxy.

24. A compound according to claim 6 of the formula (I), in which m is 1 or 2.

25. A compound according to claim 2 of the formula (I), in which A—$R_7$ is $C_2H_5$.

26. A compound according to claim 2 of the formula (I), in which A—$R_7$ is $CH_3$.

* * * * *